US012065516B2

(12) United States Patent
Song et al.

(10) Patent No.: US 12,065,516 B2
(45) Date of Patent: Aug. 20, 2024

(54) POLYMERIC SOLID SUPPORT FOR OLIGONUCLEOTIDE SYNTHESIS

(71) Applicant: Hongene Biotech Corporation, Union City, CA (US)

(72) Inventors: Jingshe Song, Union City, CA (US); John Michael Cue, Union City, CA (US); Yun-Chiao Yao, Union City, CA (US); David Yu, Union City, CA (US); Aldrich N. K. Lau, Palo Alto, CA (US)

(73) Assignee: Hongene Biotech Corporation, Union City, CA (US)

( * ) Notice: Subject to any disclaimer, the term of this patent is extended or adjusted under 35 U.S.C. 154(b) by 0 days.

(21) Appl. No.: 18/483,423

(22) Filed: Oct. 9, 2023

(65) Prior Publication Data

US 2024/0052071 A1 Feb. 15, 2024

Related U.S. Application Data

(62) Division of application No. 18/048,350, filed on Oct. 20, 2022, now Pat. No. 11,814,450.

(60) Provisional application No. 63/271,017, filed on Oct. 22, 2021.

(51) Int. Cl.
*C08F 12/32* (2006.01)
*C08F 2/08* (2006.01)
*C08F 12/22* (2006.01)

(52) U.S. Cl.
CPC ............... *C08F 12/32* (2013.01); *C08F 2/08* (2013.01); *C08F 12/22* (2013.01)

(58) Field of Classification Search
CPC ..... C08K 5/20; C07K 5/06026; C08F 236/14; C08F 2810/20; C08F 8/30; C08F 12/32; C08F 12/22; C08F 2/08; C08G 77/388
See application file for complete search history.

(56) References Cited

U.S. PATENT DOCUMENTS

| | | |
|---|---|---|
| 3,743,628 A | 7/1973 | Bodanszky et al. |
| 7,115,672 B2 | 10/2006 | Mori et al. |
| 7,153,890 B2 | 12/2006 | Mori et al. |
| 7,348,391 B2 | 3/2008 | Ravikumar et al. |
| 7,700,706 B2 | 4/2010 | Ravikumar et al. |
| 7,872,084 B2 | 1/2011 | Konishi et al. |
| 8,076,383 B2 | 12/2011 | Konishi et al. |
| 8,582,542 B2 | 11/2013 | Kütt et al. |
| 8,653,152 B2 | 2/2014 | Mori et al. |
| 8,669,356 B2 | 3/2014 | Hayakawa et al. |
| 8,802,745 B2 | 8/2014 | Mori et al. |
| 8,835,656 B2 | 9/2014 | Tsukamoto et al. |
| 9,045,573 B2 | 6/2015 | Maeta et al. |
| 10,253,153 B2 | 4/2019 | Maeta et al. |
| 11,814,450 B2 | 11/2023 | Song et al. |
| 2012/0010396 A1* | 1/2012 | Mori ............ C08F 220/20 536/25.31 |
| 2015/0152234 A1 | 6/2015 | Maeta et al. |
| 2017/0136450 A1 | 5/2017 | Hong et al. |

FOREIGN PATENT DOCUMENTS

| | | |
|---|---|---|
| EP | 1 433 795 B1 | 6/2010 |
| JP | 2010-248084 | 11/2010 |
| WO | WO 00/56790 | 9/2000 |
| WO | WO 22/110559 | 6/2022 |

OTHER PUBLICATIONS

Beihoffer et al., 1988, The introduction of hydroxyl functionality into polymers: the synthesis, polymerization, and hydrolysis of vinylbenzyl acetate, J. Polym. Sci., Part A: Polym. Chem., 26:343-353.
Frechet et al., 1991, Chemically amplified imaging materials based on electrophilic aromatic substitution, Macromolecules, 24:1746-1754.
Gage et al., 2020, Semicontinuous process for GMP manufacture of a carbapenem intermediate via carbene insertion using an immobilized rhodium catalyst, Org. Process. Res. Dev., 24:2025-2033.
Hubbard et al., 1998, Polymers with pendant vinyl groups, including poly(divinylbenzene-co-ethylvinylbenzene), Reactive & Functional Polymers, 36:1-16.
Kanaoka et al., 1996, Living Cationic polymerization of p-chlorostyrene and related para-substituted styrene derivatives at room temperature, Macromolecules, 29:1778-1783.
Kotani et al., 2000, Living radical polymerization of para-substituted styrene and synthesis of styrene-based copolymers with Rhenium and iron complex catalysts, Macromolecules, 33:6746-6751.
Lime et al., 2009, Hydrobromination of residual vinyl groups on divinylbenzene polymer particles followed by atom transfer radical surface graft polymerization, J. Polym. Sci.: Part A: Polym. Chem., 47:1259-1265.
Nukaga et al., Stereocontrolled solid-phase synthesis of phosphate/ phosphorothioate (PO/PS) chimeric oligodeoxyribonculeotides on an automated synthesizer using an oxaphospholidine-phosphoramidite method, J. Org. Chem, 81:2753-2762.
Okay et al., 1995, Cyclization and reduced pendant vinyl group reactivity during the free-radical cross-linking polymerization of 1,4-divinylbenzene, Macromolecules, 28:2728-2737.
Rajan et al., 2005, Diblock and triblock copolymers of styrene and acetoxymethylstyrene by one-pot ATRP, J. Polym. Sci.: Part A: Polym. Chem. 43:575-583.

(Continued)

*Primary Examiner* — Robert D Harlan
(74) *Attorney, Agent, or Firm* — Knobbe, Martens, Olson & Bear, LLP

(57) ABSTRACT

Embodiments of the present application relate to porous polymeric beads solid support for use in oligonucleotide synthesis and the method of producing and using the same. Further embodiments relate to porous polymeric beads and method for preparing and using the same.

20 Claims, 8 Drawing Sheets

(56) References Cited

OTHER PUBLICATIONS

Satheeshkumar et al., 2018, Creation of micropores by RAFT copolymerization of conjugated multi-vinyl cross-linkers, Polym. Chem., 9:5680-5689.
Wilson et al., 1997, Enhanced site isolation in cross-link-functionalized polystyrene networks: mobility studies using steady-state fluorescence and ESR techniques, Macromolecules, 30:3340-3340.
Wilson et al., 1998 Solvent and reagent accessibility within oligo(ethylene glycol) ether [PEG} cross-linked polystyrene beads, J. Org. Chem., 63:5094-5099.
International Search Report and Written Opinion dated Feb. 3, 2023 in international application No. PCT/US2022/047251.

\* cited by examiner

POLYMERIC SOLID SUPPORT FOR OLIGONUCLEOTIDE SYNTHESIS

FIELD

The present application relates to polymeric solid support for use in oligonucleotide synthesis and the method of producing and using the same.

BACKGROUND

Synthetic oligonucleotides have been widely used in various biological and pharmaceutical applications in the past few decades. The most common way to produce synthetic oligonucleotides the solid-phase oligo synthesis, in particular those utilizing phosphoramidite triester intermediates. The general process for manufacture of an oligonucleotide by the Köster method include the following steps: First, a synthesis support is prepared by covalently linking a suitable nucleoside to a solid support SS through a linker, usually a difunctional linker, forming a 3' nucleoside attached solid support. Then synthesis is carried out from 3'- to 5'-end of the oligonucleotide. In each cycle, the following steps are carried out: (1) removal of the 5' protecting group; (2) coupling; (3) oxidation; and (4) capping of unreacted nucleoside with free 5' hydroxy group. The solid support for the oligo synthesis is packed in a reaction column, and the solution containing the reactants is quickly flowed through the reaction column under a certain pressure to complete reaction. Each of the steps (1)-(4) may be followed by one or more wash steps, whereby a clean solvent is introduced to the column to wash soluble materials from the column, push reagents and/or activators through the column, or both.

Solid supports for oligo synthesis generally have the following features: first, a solid support should have reactive sites for the initial nucleoside to be immobilized to the support. The reactive sites should be evenly distributed on the surface of the solid support to reduce the interference between nucleic acid molecular chains. Second, the reactive site can be cleaved after the oligo synthesis is complete. Third, the solid support must maintain physical and chemical stability during the synthesis process. Four, the solid support should have a large enough pore size and ideal pore size distribution. Finally, the solid support should exhibit a certain degree of hydrophobicity, because the phosphoramidite monomer used in oligonucleotide synthesis is sensitive to moisture, and the presence of moisture may reduce the reaction efficiency.

Porous crosslinked phenolic polystyrene copolymer beads are utilized as solid supports for oligonucleotide synthesis. Phenolic beads are prepared by emulsion copolymerization of styrene, divinylbenzene (DVB), and acetoxystyrene in the presence of a porogen. See, e.g., U.S. Pat. Nos. 7,115,672, 7,153,890, 7,348,391 and 7,700,706. One undesirable characteristic of the phenolic beads is its susceptibility to oxidation by air.

In addition, commercial DVB also has a fundamental drawback because it typically consists of a mixture of 1,4-DVB, 1,3-DVB, 1-ethyl-4-vinylbenzene and 1-ethyl-3-vinylbenzene. Further, free radical cross-linking copolymerization is accompanied by cyclization and the generation of pendant vinyl groups, the remaining vinyl group after the free radical polymerization of the first vinyl groups. These pendant vinyl groups exhibit drastically reduced reactivity. See Okay, et al., *Macromolecules* 1995, 28, 2728-2737. Pendant vinyl groups can undergo hydrobromination and the resulting crosslinked polystyrene to be used for subsequent atom transfer radical surface grafting polymerization. Lime, et al., *J. Polym. Sci.: Part A: Polym. Chem.* 2009, 47, 1259-1265. The left-over pendant vinyl groups may have detrimental effects on the physical/mechanical properties of DVB-crosslinked polystyrene beads. Pendant vinyl groups on the surface of porous, crosslinked polystyrene beads may also participate in undesirable side reactions during oligonucleotide synthesis. Under certain cross-linking conditions, DVB can also form undesirable linear polymers. Hubbard, et al., *Reactive & Functional Polymers,* 1998, 36, 1-16.

Solid supports for conventional oligonucleotide synthesis are typically manufactured with a loading of 20-30 μmol of nucleoside per gram of resin. Oligonucleotide synthesis at higher loadings becomes less efficient owing to steric hindrance between adjacent DNA chains attached to the resin; however, polystyrene supports with loadings of up to 350 μmol/g are used in some applications, particularly for short oligonucleotides, and enable the synthesis of large quantities of oligonucleotides. However, there exists a need for improved polymeric solid support that can not only accommodate the increased loading of the nucleoside, but also enable the synthetic yield of longer length of oligonucleotides.

SUMMARY

Some aspect of the present disclosure provides a copolymer comprising one or more comonomer repeating units of Formula (I), and (II), and one or more crosslinker repeating units of Formula (III), (IV) or (V) or combinations thereof:

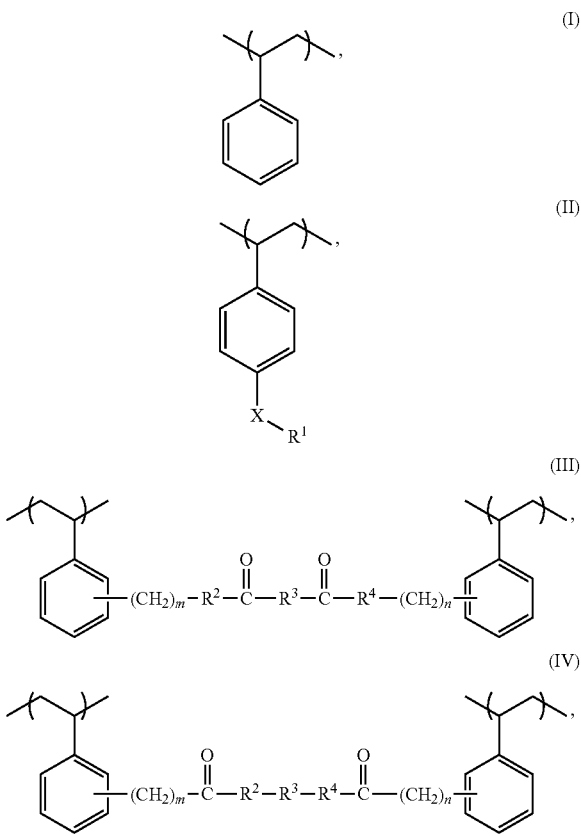

-continued

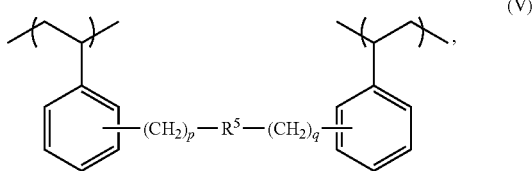
(V)

wherein X is absent or $C_1$-$C_4$ alkylene;
$R^1$ is OH, $NH_2$, OC(=O)$R^a$, or NHC(=O)$R^b$;
each of $R^a$ and $R^b$ is independently optionally substituted $C_1$-$C_6$ alkyl or optionally substituted $C_6$-$C_{10}$ aryl;
each of $R^2$ and $R^4$ is independently —O— or —$NR^c$—;
each $R^c$ is independently H or $C_1$-$C_6$ alkyl;
each $R^3$ is independently an optionally substituted $C_6$-$C_{10}$ arylene, optionally substituted $C_3$-$C_{10}$ membered cycloalkylene, optionally substituted five to ten membered heteroarylene, optionally substituted three to ten membered heterocyclylene, optionally substituted $C_1$-$C_{10}$ alkylene, optionally substituted 2 to 1500 membered heteroalkylene, or $C_1$-$C_{10}$ alkylene or 2 to 1500 membered heteroalkylene each independently interrupted by a ring or ring system selected from the group consisting of an optionally substituted $C_6$-$C_{10}$ arylene, optionally substituted $C_3$-$C_{10}$ membered cycloalkylene, optionally substituted five to ten membered heteroarylene, and optionally substituted three to ten membered heterocyclylene;
$R^5$ is a bond, an optionally substituted $C_6$-$C_{10}$ arylene, optionally substituted $C_3$-$C_{10}$ membered cycloalkylene, optionally substituted five to ten membered heteroarylene, optionally substituted three to ten membered heterocyclylene, optionally substituted $C_1$-$C_{10}$ alkylene, or optionally substituted 2 to 1500 membered heteroalkylene;
each of m, n, p and q is independently 0, 1, 2, 3, 4, 5 or 6;
wherein each phenyl moiety in Formula (I), (II), (III), (IV) or (V) is optionally substituted with one or more $R^6$; and
each $R^6$ is independently selected from the group consisting of halo, cyano, hydroxy, amino, $C_1$-$C_6$ alkyl, $C_1$-$C_6$ haloalkyl, $C_1$-$C_6$ alkoxy, $C_1$-$C_6$ haloalkoxy, ($C_1$-$C_6$ alkyl)amino, ($C_1$-$C_6$ alkyl)hydroxy, ($C_1$-$C_6$ alkoxy)$C_1$-$C_6$ alkyl, and —O—($C_1$-$C_6$ alkoxy)$C_1$-$C_6$ alkyl. In some embodiments, the polymer described herein comprises one or more repeating units of:

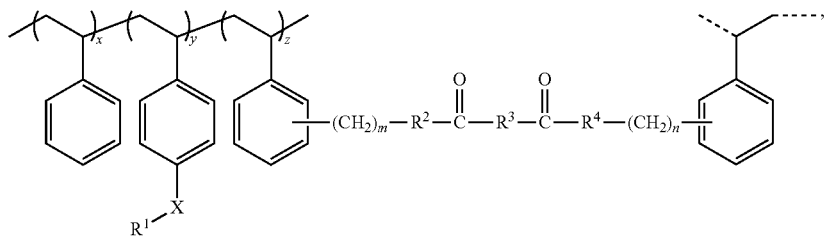

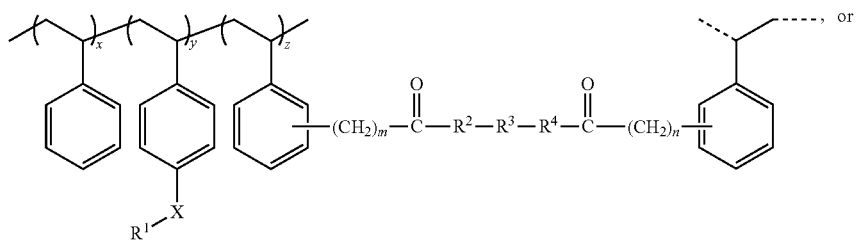

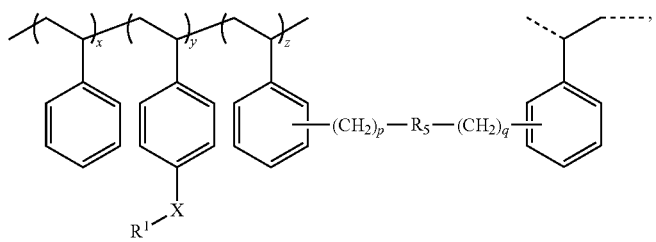

or combinations thereof, wherein x, y, and z are each independently an integer from 1 to about 10000. In some further embodiments, the polymer of the present disclosure may be in the form of porous beads.

Some aspect of the present disclosure relates to a process of producing porous polymeric beads, comprising:
copolymerizing a styrene monomer, an acetoxy styrene monomer or an acetoxymethyl styrene monomer, and one or more crosslinker monomers of Formula (VI) (VII), or (VIII) or combinations thereof, to provide a crosslinked copolymer; and
hydrolyzing the crosslinked copolymer to convert the acetoxymethyl group to hydroxymethyl group or the acetoxy group to hydroxy group in the crosslinked copolymer;

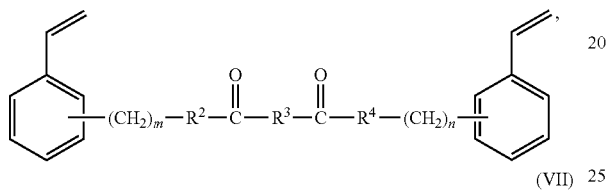

(VI)

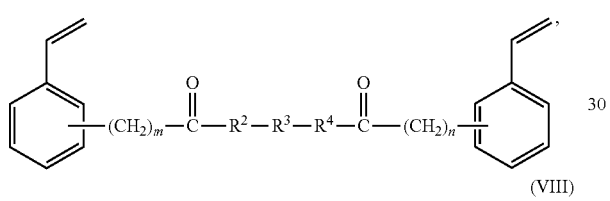

(VII)

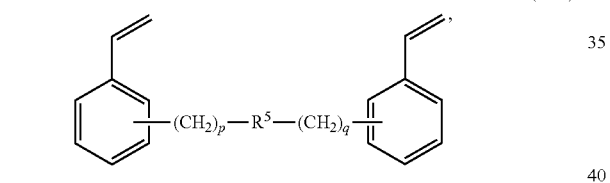

(VIII)

wherein each of $R^2$ and $R^4$ is independently —O— or —$NR^c$—;

each $R^c$ is independently H or $C_1$-$C_6$ alkyl;

each $R^3$ is independently an optionally substituted $C_6$-$C_{10}$ arylene, optionally substituted $C_3$-$C_{10}$ membered cycloalkylene, optionally substituted five to ten membered heteroarylene, optionally substituted three to ten membered heterocyclylene, optionally substituted $C_1$-$C_{10}$ alkylene, optionally substituted 2 to 1500 membered heteroalkylene, or $C_1$-$C_{10}$ alkylene or 2 to 1500 membered heteroalkylene each independently interrupted by a ring or ring system selected from the group consisting of an optionally substituted $C_6$-$C_{10}$ arylene, optionally substituted $C_3$-$C_{10}$ membered cycloalkylene, optionally substituted five to ten membered heteroarylene, and optionally substituted three to ten membered heterocyclylene;

$R^5$ is a bond, optionally substituted $C_6$-$C_{10}$, optionally substituted $C_3$-$C_{10}$ membered cycloalkylene, optionally substituted five to ten membered heteroarylene, optionally substituted three to ten membered heterocyclylene, optionally substituted $C_1$-$C_{10}$ alkylene, or optionally substituted 2 to 1500 membered heteroalkylene;

each of m, n, p and q is independently 0, 1, 2, 3, 4, 5 or 6;

wherein each phenyl moiety in Formula (VI), (VII) or (VIII) is optionally substituted with one or more $R^6$; and each $R^6$ is independently selected from the group consisting of halo, cyano, hydroxy, amino, $C_1$-$C_6$ alkyl, $C_1$-$C_6$ haloalkyl, $C_1$-$C_6$ alkoxy, $C_1$-$C_6$ haloalkoxy, ($C_1$-$C_6$ alkyl)amino, ($C_1$-$C_6$ alkyl)hydroxy, ($C_1$-$C_6$ alkoxy)$C_1$-$C_6$ alkyl, and —O—($C_1$-$C_6$ alkoxy)$C_1$-$C_6$ alkyl. In some embodiments, the crosslinked copolymer comprising one or more repeating units of:

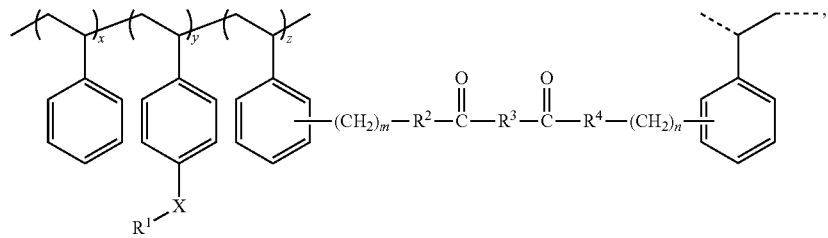

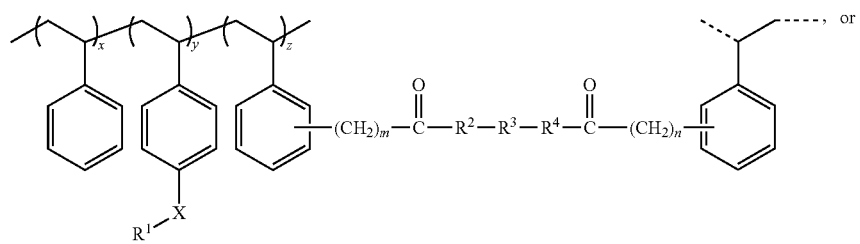

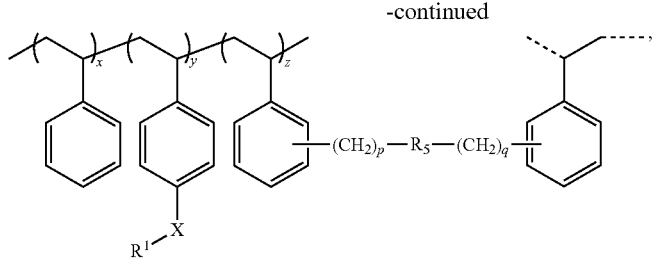

or combinations thereof, wherein x, y, and z are each independently an integer from 1 to about 10000, wherein X is absent or $CH_2$; and $R^1$ is —OH.

Some additional aspect of the present disclosure relates to polymeric beads formed by the process described herein.

Some additional aspect of the present disclosure relates to a compound of Formula (A1):

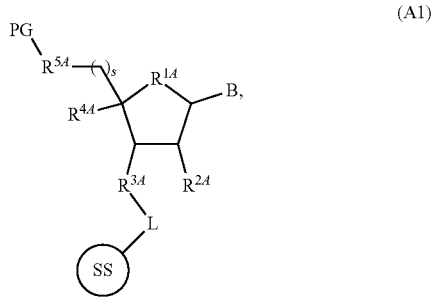

or a salt thereof, wherein:

$R^{1A}$ is O, S, $CH_2$, CFH, $CF_2$, or —CH=CH—;

$R^{2A}$ is H, hydroxy, a protected hydroxy, halogen, —O—($C_1$-$C_6$ alkyl), or —O—($C_1$-$C_6$ haloalkyl), or $R^{2A}$ together with $R^{4A}$ forms an optionally substituted $C_3$-$C_{10}$ carbocyclyl or an optionally substituted five to ten membered heterocyclyl;

$R^{3A}$ is O, S, $CH_2$, or NH;

$R^{4A}$ is H, or $R^{4A}$ together with $R^{2A}$ forms an optionally substituted $C_3$-$C_{10}$ carbocyclyl or an optionally substituted five to ten membered heterocyclyl;

$R^{5A}$ is O, S, $CH_2$, or NH;

s is 0 or 1;

B is a natural or modified nucleobase;

PG is H or a removable protecting group;

L is a linking moiety; and

SS is a polymeric bead as disclosed herein.

Some additional aspect of the present disclosure relates to a compound of Formula (A2):

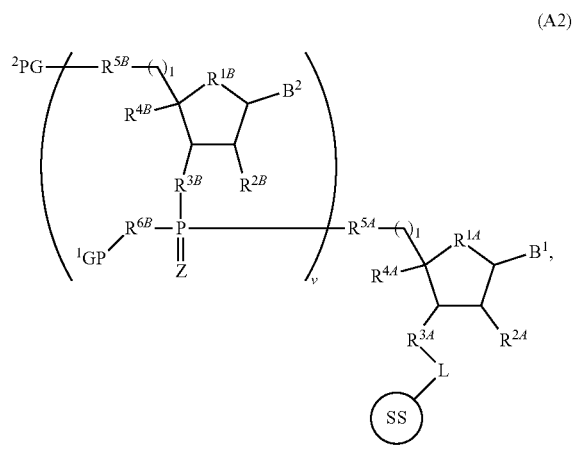

or a salt thereof, wherein
each of $R^{1A}$ and $R^{1B}$ is independently O, S, $CH_2$, CFH, $CF_2$, or —CH=CH—;
each of $R^{2A}$ and $R^{2B}$ is independently H, hydroxy, a protected hydroxy, halogen, —O—($C_1$-$C_6$ alkyl), or —O—($C_1$-$C_6$ haloalkyl), or $R^{2A}$ together with $R^{4A}$ forms an optionally substituted $C_3$-$C_{10}$ carbocyclyl or an optionally substituted five to ten membered heterocyclyl, or $R^{2B}$ together with $R^{4B}$ forms an optionally substituted $C_3$-$C_{10}$ carbocyclyl or an optionally substituted five to ten membered heterocyclyl;
each of $R^{3A}$ and $R^{3B}$ is independently O, S, $CH_2$, or NH;
each of $R^{4A}$ and $R^{4B}$ is H, or $R^{4A}$ together with $R^{2A}$ forms an optionally substituted $C_3$-$C_{10}$ carbocyclyl or an optionally substituted five to ten membered heterocyclyl, or $R^{4B}$ together with $R^{2B}$ forms an optionally substituted $C_3$-$C_{10}$ carbocyclyl or an optionally substituted five to ten membered heterocyclyl,
each of $R^{5A}$, $R^{5B}$ and $R^{6B}$ is independently O, S, $CH_2$, or NH;
each of s and u is independently 0 or 1;
v is an integer of 1 to 500;
each of $B^1$ and $B^2$ is independently a natural or modified nucleobase;
each of $PG^1$ and $PG^2$ is independently H or a removable protecting group;
Z is O or S;
L is a linking moiety; and
SS is a polymeric bead as disclosed herein.

DETAILED DESCRIPTION

Figure 1:
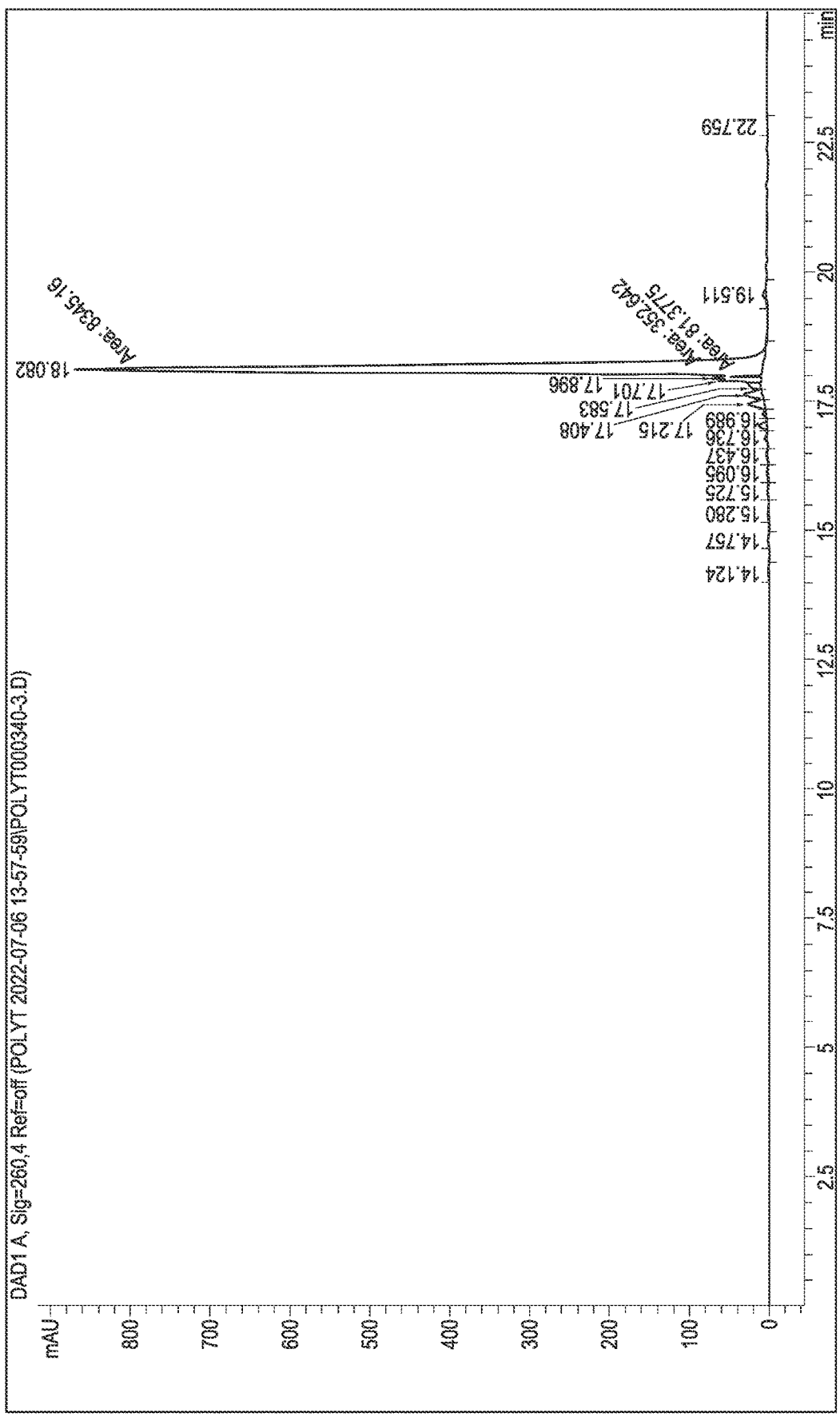
FIG. 1 is a HPLC chromatogram of a T20 DNA oligonucleotide synthesized utilizing crosslinker of Formula VIII-4 according one embodiment of the present disclosure.

The compounds disclosed herein relate to novel and improved solid support for oligonucleotide synthesis. In some embodiments, the polymeric solid support disclosed herein (e.g., porous polymeric beads) confers improved loading capacity, yield and stability in oligonucleotide synthesis and mitigates the oxidative phenolic functionality that may impair bioconjugation. Furthermore, the polymeric solid support described herein may also improve the physical/mechanical integrity of the solid support. By avoiding the use of divinylbenzene in the manufacturing of the polymeric beads described herein, it eliminates the undesirable side reaction caused by divinylbenzene (DVB).

Definitions

Unless defined otherwise, all technical and scientific terms used herein have the same meaning as is commonly understood by one of ordinary skill in the art. All patents, applications, published applications and other publications referenced herein are incorporated by reference in their entirety unless stated otherwise. In the event that there are a plurality of definitions for a term herein, those in this section prevail unless stated otherwise. As used in the specification and the appended claims, the singular forms "a," "an" and "the" include plural referents unless the context clearly dictates otherwise. Unless otherwise indicated, conventional methods of mass spectroscopy, NMR, HPLC, protein chemistry, biochemistry, recombinant DNA techniques and pharmacology are employed. The use of "or" or "and" means "and/or" unless stated otherwise. Furthermore, use of the term "including" as well as other forms, such as "include", "includes," and "included," is not limiting.

While the disclosure has been illustrated and described in detail in the foregoing description, such description is to be considered illustrative or exemplary and not restrictive. The disclosure is not limited to the disclosed embodiments. Variations to the disclosed embodiments can be understood and effected by those skilled in the art in practicing the claimed disclosure, from a study of the disclosure and the appended claims.

All references cited herein are incorporated herein by reference in their entirety. To the extent publications and patents or patent applications incorporated by reference contradict the disclosure contained in the specification, the specification is intended to supersede and/or take precedence over any such contradictory material.

Unless otherwise defined, all terms (including technical and scientific terms) are to be given their ordinary and customary meaning to a person of ordinary skill in the art, and are not to be limited to a special or customized meaning unless expressly so defined herein. It should be noted that the use of particular terminology when describing certain features or aspects of the disclosure should not be taken to imply that the terminology is being re-defined herein to be restricted to include any specific characteristics of the features or aspects of the disclosure with which that terminology is associated.

Where a range of values is provided, it is understood that the upper and lower limit, and each intervening value between the upper and lower limit of the range is encompassed within the embodiments.

The term "oligonucleotide" embraces a class of compounds that include naturally-occurring, as well as modified, oligonucleotides. Both naturally-occurring and modified oligonucleotides have proven useful in a variety of settings, and both may be made by similar processes, with appropriate modifications made to account for the specific modifications adopted. A naturally occurring oligonucleotide (i.e., a short strand of DNA or RNA) may be envisioned as being a member of the following generic formulas, denominated oligo-RNA and oligo-DNA, respectively. Physiologic pH, an oligonucleotide occurs as the anion, as the phosphate easily dissociates at neutral pH, and an oligonucleotide will generally occur in solid phase, whether amorphous or crystalline, as a salt. Thus, unless otherwise modified, the term "oligonucleotide" encompasses each of the anionic, salt and free acid forms above.

As used herein, "loading capacity" or "load" is expressed in mmol or pmol of a nucleoside bound to the solid support medium per gram of solid support medium (i.e., mmol/g).

As used herein, any "R" group(s) represent substituents that can be attached to the indicated atom. An R group may be substituted or unsubstituted. If two "R" groups are described as being "taken together" the R groups and the atoms they are attached to can form a cycloalkyl, aryl, heteroaryl, or heterocycle. For example, without limitation, if $R^a$ and $R^b$, and the atom to which it is attached, are indicated to be "taken together" or "joined together" it means that they are covalently bonded to one another to form a ring:

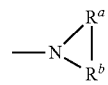

Whenever a group is described as being "optionally substituted" that group may be unsubstituted or substituted with one or more of the indicated substituents. Likewise, when a group is described as being "substituted", the substituent may be selected from one or more of the indicated substituents. If no substituents are indicated, it is meant that the indicated "optionally substituted" or "substituted" group may be one or more group(s) individually and independently selected from alkyl (e.g., $C_1$-$C_6$ alkyl); alkenyl (e.g., $C_2$-$C_6$ alkenyl); alkynyl (e.g., $C_2$-$C_6$ alkynyl); $C_3$-$C_8$ carbocyclyl (for example, $C_3$-$C_8$ cycloalkyl, $C_3$-$C_8$ cycloalkenyl, or $C_3$-$C_8$ cyclalkynyl, each may further be optionally substituted, for example, with halo, $C_1$-$C_6$ alkyl, $C_1$-$C_6$ alkoxy, $C_1$-$C_6$ haloalkyl, $C_1$-$C_6$ haloalkoxy, ($C_1$-$C_6$ alkoxy)$C_1$-$C_6$ alkyl, or —O($C_1$-$C_6$ alkoxy)$C_1$-$C_6$ alkyl); ($C_3$-$C_7$ carbocyclyl)$C_1$-$C_6$ alkyl (may further be optionally substituted, for example, with halo, $C_1$-$C_6$ alkyl, $C_1$-$C_6$ alkoxy, $C_1$-$C_6$ haloalkyl, $C_1$-$C_6$ haloalkoxy, ($C_1$-$C_6$ alkoxy)$C_1$-$C_6$ alkyl, or —O($C_1$-$C_6$ alkoxy)$C_1$-$C_6$ alkyl); 5-10 membered heterocyclyl (may further be optionally substituted, for example, with halo, $C_1$-$C_6$ alkyl, $C_1$-$C_6$ alkoxy, $C_1$-$C_6$ haloalkyl, $C_1$-$C_6$ haloalkoxy, ($C_1$-$C_6$ alkoxy)$C_1$-$C_6$ alkyl, or —O($C_1$-$C_6$ alkoxy)$C_1$-$C_6$ alkyl); (5-10 membered heterocyclyl)$C_1$-$C_6$ alkyl (may further be optionally substituted, for example, with halo, $C_1$-$C_6$ alkyl, $C_1$-$C_6$ alkoxy, $C_1$-$C_6$ haloalkyl, $C_1$-$C_6$ haloalkoxy, ($C_1$-$C_6$ alkoxy)$C_1$-$C_6$ alkyl, or —O($C_1$-$C_6$ alkoxy)$C_1$-$C_6$ alkyl); aryl (may further be optionally substituted, for example, with halo, $C_1$-$C_6$ alkyl, $C_1$-$C_6$ alkoxy, $C_1$-$C_6$ haloalkyl, $C_1$-$C_6$ haloalkoxy, ($C_1$-$C_6$ alkoxy)$C_1$-$C_6$ alkyl, or —O($C_1$-$C_6$ alkoxy)$C_1$-$C_6$ alkyl); (aryl)$C_1$-$C_6$ alkyl (may further be optionally substituted, for example, with halo, $C_1$-$C_6$ alkyl, $C_1$-$C_6$ alkoxy, $C_1$-$C_6$ haloalkyl, $C_1$-$C_6$ haloalkoxy, ($C_1$-$C_6$ alkoxy)$C_1$-$C_6$ alkyl, or —O($C_1$-$C_6$ alkoxy)$C_1$-$C_6$ alkyl); 5-10 membered heteroaryl (may further be optionally substituted with halo, $C_1$-$C_6$ alkyl, $C_1$-$C_6$ alkoxy, $C_1$-$C_6$ haloalkyl, $C_1$-$C_6$ haloalkoxy, ($C_1$-$C_6$ alkoxy)$C_1$-$C_6$ alkyl, or —O($C_1$-$C_6$ alkoxy)$C_1$-$C_6$ alkyl); (5-10 membered heteroaryl)$C_1$-$C_6$ alkyl (may further be optionally substituted with halo, $C_1$-$C_6$ alkyl, $C_1$-$C_6$ alkoxy, $C_1$-$C_6$ haloalkyl, $C_1$-$C_6$ haloalkoxy, ($C_1$-$C_6$ alkoxy)$C_1$-$C_6$ alkyl, or —O($C_1$-$C_6$ alkoxy)$C_1$-$C_6$ alkyl); halo (e.g., fluoro, chloro, bromo, iodo); cyano; hydroxy; protected hydroxy; alkoxy (e.g., $C_1$-$C_6$ alkoxy); haloalkyl (e.g., $C_1$-$C_6$ haloalkyl, such as —$CF_3$); haloalkyl (e.g., $C_1$-$C_6$ haloalkoxy such as —$OCF_3$); ($C_1$-$C_6$ alkoxy)$C_1$-$C_6$ alkyl; —O($C_1$-$C_6$ alkoxy)$C_1$-$C_6$ alkyl; ($C_1$-$C_6$ haloalkoxy)$C_1$-$C_6$ alkyl; —O($C_1$-$C_6$ haloalkoxy)$C_1$-$C_6$ alkyl; aryloxy; sulfhydryl (mercapto); alkylthio (e.g., $C_1$-$C_6$ alkylthio); arylthio; azido; nitro; O-carbamyl; N-carbamyl; O-thiocarbamyl; N-thiocarbamyl; C-amido; N-amido; S-sulfonamido; N-sulfonamido; C-carboxy; protected C-carboxy; O-carboxy; acyl; cyanate; isocyanato; thiocyanato; isothiocyanato; silyl; sulfenyl; sulfinyl; sulfonyl; trihalomethanesulfonyl; trihalomethanesulfonamido; amino (including protected derivatives thereof); mono-substituted amino (for example, NH($C_1$-$C_6$ alkyl); di-substituted amino (for example, N($C_1$-$C_6$ alkyl)$_2$); oxo (=O); and thioxo (=S).

As used herein, "$C_a$ to $C_b$" in which "a" and "b" are integers refer to the number of carbon atoms in an alkyl group, or the number of ring atoms of a cycloalkyl, aryl, heteroaryl or heterocyclyl group. That is, the alkyl, ring of the cycloalkyl, and ring of the aryl, can contain from "a" to "b", inclusive, carbon atoms. Likewise, the ring of the heteroaryl and ring of the heterocyclyl can contain from "a" to "b", inclusive, total ring atoms. Thus, for example, a "$C_1$ to $C_4$ alkyl" group refers to all alkyl groups having from 1 to 4 carbons, that is, $CH_3$—, $CH_3CH_2$—, $CH_3CH_2CH_2$—, $(CH_3)_2CH$—, $CH_3CH_2CH_2CH_2$—, $CH_3CH_2CH(CH_3)$— and $(CH_3)_3C$—; a $C_3$ to $C_4$ cycloalkyl group refers to all cycloalkyl groups having from 3 to 4 carbon atoms, that is, cyclopropyl and cyclobutyl. Similarly, a "4 to 6 membered heterocyclyl" group refers to all heterocyclyl groups with 4 to 6 total ring atoms, for example, azetidine, oxetane, oxazoline, pyrrolidine, piperidine, piperazine, morpholine, and the like. If no "a" and "b" are designated with regard to an alkyl, cycloalkyl, aryl, heteroaryl or heterocyclyl group, the broadest range described in these definitions is to be assumed. As used herein, the term "$C_1$-$C_6$" includes $C_1$, $C_2$, $C_3$, $C_4$, $C_5$ and $C_6$, and a range defined by any of the two numbers. For example, $C_1$-$C_6$ alkyl includes $C_1$, $C_2$, $C_3$, $C_4$, $C_5$ and $C_6$ alkyl, $C_2$-$C_6$ alkyl, $C_1$-$C_3$ alkyl, etc. Similarly, $C_3$-$C_8$ carbocyclyl or cycloalkyl each includes hydrocarbon ring containing 3, 4, 5, 6, 7 and 8 carbon atoms, or a range defined by any of the two numbers, such as $C_3$-$C_7$ cycloalkyl or $C_5$-$C_6$ cycloalkyl.

As used herein, "alkyl" refers to a straight or branched hydrocarbon chain that comprises a fully saturated (no double or triple bonds) hydrocarbon group. The alkyl group may have 1 to 20 carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc., up to and including 20 carbon atoms, although the present definition also covers the occurrence of the term "alkyl" where no numerical range is designated). The alkyl group may also be a medium size alkyl having 1 to 10 carbon atoms. The alkyl group could also be a lower alkyl having 1 to 6 carbon atoms. The alkyl group of the compounds may be designated as "$C_1$-$C_4$ alkyl" or similar designations. By way of example only, "$C_1$-$C_4$ alkyl" indicates that there are one to four carbon atoms in the alkyl chain, i.e., the alkyl chain is selected from methyl, ethyl, propyl, iso-propyl, n-butyl, iso-butyl, sec-butyl, and t-butyl. Typical alkyl groups include, but are in no way limited to, methyl, ethyl, n-propyl, isopropyl, butyl, isobutyl, tertiary butyl, pentyl (straight chain or branched), and hexyl (straight chain or branched). The alkyl group may be substituted or unsubstituted.

As used herein, "alkenyl" refers to a straight or branched hydrocarbon chain containing one or more double bonds. The alkenyl group may have 2 to 20 carbon atoms. By way of example only, "$C_2$-$C_6$ alkenyl" indicates that there are two to six carbon atoms in the alkenyl chain, i.e., the alkenyl chain is selected from the group consisting of ethenyl, propen-1-yl, propen-2-yl, propen-3-yl, buten-1-yl, buten-2-yl, buten-3-yl, buten-4-yl, 1-methyl-propen-1-yl, 2-methyl-propen-1-yl, 1-ethyl-ethen-1-yl, 2-methyl-propen-3-yl, buta-1,3-dienyl, buta-1,2,-dienyl, and buta-1,2-dien-4-yl. Typical alkenyl groups include, but are in no way limited to, ethenyl, propenyl, butenyl, pentenyl, and hexenyl, and the like. The alkenyl group may be substituted or unsubstituted.

As used herein, "alkynyl" refers to a straight or branched hydrocarbon chain containing one or more triple bonds. The alkynyl group may have 2 to 20 carbon atoms. By way of example only, "$C_2$-$C_4$ alkynyl" indicates that there are two to six carbon atoms in the alkynyl chain, i.e., the alkynyl chain is selected from the group consisting of ethynyl, propyn-1-yl, propyn-2-yl, butyn-1-yl, butyn-3-yl, butyn-4-yl, and 2-butynyl. Typical alkynyl groups include, but are in no way limited to, ethynyl, propynyl, butynyl, pentynyl, and hexynyl, and the like. The alkynyl group may be substituted or unsubstituted.

As used herein, "cycloalkyl" refers to a completely saturated (no double or triple bonds) mono- or multi-cyclic hydrocarbon ring system. When composed of two or more rings, the rings may be joined together in a fused, bridged or spiro fashion. As used herein, the term "fused" refers to two rings which have two atoms and one bond in common. As used herein, the term "bridged cycloalkyl" refers to compounds wherein the cycloalkyl contains a linkage of one or more atoms connecting non-adjacent atoms. As used herein, the term "spiro" refers to two rings which have one atom in common and the two rings are not linked by a bridge. Cycloalkyl groups can contain 3 to 10 atoms in the ring(s), 3 to 8 atoms in the ring(s), or 3 to 6 atoms in the ring(s). A cycloalkyl group may be unsubstituted or substituted. Examples of monocyclic cycloalkyl groups include, but are in no way limited to, cyclopropyl, cyclobutyl, cyclopentyl, cyclohexyl, cycloheptyl and cyclooctyl. Examples of bicyclic fused cycloalkyl groups are decahydronaphthalenyl, dodecahydro-1H-phenalenyl and tetradecahydroanthracenyl; examples of bicyclic bridged cycloalkyl groups are bicyclo[1.1.1]pentyl, adamantanyl and norbornanyl; and examples of bicyclic spiro cycloalkyl groups include spiro[3.3]heptane and spiro[4.5]decane.

As used herein, "carbocyclyl" refers to a non-aromatic a mono- or multi-cyclic hydrocarbon ring system. When composed of two or more rings, the rings may be joined together in a fused, bridged or spiro fashion, as described herein. Carbocyclyl groups can contain 3 to 30 atoms in the ring(s), 3 to 20 atoms in the ring(s), 3 to 10 atoms in the ring(s), 3 to 8 atoms in the ring(s) or 3 to 6 atoms in the ring(s). A carbocyclyl group may be unsubstituted or substituted. Examples of carbocyclyl groups include, but are in no way limited to, cycloalkyl groups, as defined herein, and the non-aromatic portions of 1,2,3,4-tetrahydronaphthalene, 2,3-dihydro-1H-indene, 5,6,7,8-tetrahydroquinoline and 6,7-dihydro-5H-cyclopenta[b]pyridine.

As used herein, "aryl" refers to a carbocyclic (all carbon) monocyclic or multicyclic aromatic ring system (including fused ring systems where two carbocyclic rings share a chemical bond) that has a fully delocalized pi-electron system throughout all the rings. The number of carbon atoms in an aryl group can vary. For example, the aryl group can be a $C_6$ aryl group, or a $C_{10}$ aryl group. Examples of aryl groups include, but are not limited to, benzene and naphthalene. An aryl group may be substituted or unsubstituted.

As used herein, "heteroaryl" refers to a monocyclic or multicyclic aromatic ring system (a ring system with fully delocalized pi-electron system) that contain(s) one or more heteroatoms (for example, 1, 2 or 3 heteroatoms), that is, an element other than carbon, including but not limited to, nitrogen, oxygen and sulfur. The number of atoms in the ring(s) of a heteroaryl group can vary. For example, the heteroaryl group can contain 5 to 10 atoms in the ring(s), 6 to 10 atoms in the ring(s) or 5 to 6 atoms in the ring(s), such as nine carbon atoms and one heteroatom; eight carbon atoms and two heteroatoms; seven carbon atoms and three heteroatoms; eight carbon atoms and one heteroatom; seven carbon atoms and two heteroatoms; six carbon atoms and three heteroatoms; five carbon atoms and four heteroatoms; five carbon atoms and one heteroatom; four carbon atoms and two heteroatoms; three carbon atoms and three heteroatoms; four carbon atoms and one heteroatom; three carbon atoms and two heteroatoms; or two carbon atoms and three heteroatoms. Furthermore, the term "heteroaryl" includes fused ring systems where two rings, such as at least one aryl ring and at least one heteroaryl ring or at least two heteroaryl rings, share at least one chemical bond. Examples of heteroaryl rings include, but are not limited to, furan, furazan, thiophene, benzothiophene, phthalazine, pyrrole, oxazole, benzoxazole, 1,2,3-oxadiazole, 1,2,4-oxadiazole, thiazole, 1,2,3-thiadiazole, 1,2,4-thiadiazole, benzothiazole, imidazole, benzimidazole, indole, indazole, pyrazole, benzopyrazole, isoxazole, benzoisoxazole, isothiazole, triazole, benzotriazole, thiadiazole, tetrazole, pyridine, pyridazine, pyrimidine, pyrazine, purine, pteridine, quinoline, isoquinoline, quinazoline, quinoxaline, cinnoline and triazine. A heteroaryl group may be substituted or unsubstituted.

As used herein, "heterocyclyl" refers to three-, four-, five-, six-, seven-, eight-, nine-, and ten-membered mono-cyclic, bicyclic and tricyclic ring system wherein carbon atoms together with from 1 to 5 heteroatoms constitute said ring system. A heterocycle may optionally contain one or more unsaturated bonds situated in such a way, however, that a fully delocalized pi-electron system does not occur throughout all the rings (i.e., heterocyclyl groups are not aromatic). The heteroatom(s) is an element other than carbon including, but not limited to, oxygen, sulfur and nitrogen. A heterocycle may further contain one or more carbonyl functionalities, so as to make the definition include oxo-systems such as lactams, lactones, and cyclic carbamates. When composed of two or more rings, the rings may be joined together in a fused, bridged or spiro fashion. As used herein, the term "fused" refers to two rings which have two atoms and one bond in common. As used herein, the term "bridged heterocyclyl" refers to compounds wherein the heterocyclyl contains a linkage of one or more atoms connecting non-adjacent atoms. As used herein, the term "spiro" refers to two rings which have one atom in common and the two rings are not linked by a bridge. Heterocyclyl groups can contain 3 to 10 atoms in the ring(s), 3 to 8 atoms in the ring(s), 3 to 6 atoms in the ring(s), or 5 to 6 atoms in the ring(s). For example, five carbon atoms and one heteroatom; four carbon atoms and two heteroatoms; three carbon atoms and three heteroatoms; four carbon atoms and one heteroatom; three carbon atoms and two heteroatoms; two carbon atoms and three heteroatoms; one carbon atom and four heteroatoms; three carbon atoms and one heteroatom; or two carbon atoms and one heteroatom. Additionally, any nitrogen in a heterocyclyl group may be quaternized. Heterocyclyl groups can be linked to the rest of the molecule via a carbon atom in the heterocyclyl group (C-linked) or by a heteroatom in the heterocyclyl group, such as a nitrogen atom (N-linked). Heterocyclyl groups may be unsubstituted or substituted. Examples of such "heterocyclyl" groups include but are not limited to, aziridine, oxirane, thiirane, azetidine, oxetane, 1,3-dioxin, 1,3-dioxane, 1,4-dioxane, 1,2-dioxolane, 1,3-dioxolane, 1,4-dioxolane, 1,3-oxathiane, 1,4-oxathiin, 1,3-oxathiolane, 1,3-dithiole, 1,3-dithiolane, 1,4-oxathiane, tetrahydro-1,4-thiazine, 2H-1,2-oxazine, maleimide, succinimide, barbituric acid, thiobarbituric acid, dioxopiperazine, hydantoin, dihydrouracil, trioxane, hexahydro-1,3,5-triazine, imidazoline, imidazolidine, isoxazoline, isoxazolidine, oxazoline, oxazolidine, oxazolidinone, thiazoline, thiazolidine, morpholine, oxirane, piperidine N-oxide, piperidine, piperazine, pyrrolidine, azepane, pyrrolidone, pyrrolidione, 4-piperidone, pyrazoline, pyrazolidine, 2-oxopyrrolidine, tetrahydropyran, 4H-pyran, tetrahydrothiopyran, thiamorpholine, thiamorpholine sulfoxide, thiamorpholine sulfone and their benzo-fused analogs (e.g., benzimidazolidinone, tetrahydroquinoline and/or 3,4-methylenedioxyphenyl). Examples of spiro heterocyclyl groups include 2-azaspiro[3.3]heptane, 2-oxaspiro[3.3]heptane, 2-oxa-6-azaspiro[3.3]heptane, 2,6-diazaspiro[3.3]heptane, 2-oxaspiro[3.4]octane and 2-azaspiro[3.4]octane.

As used herein, "alkylene" refers to a branched, or straight chain fully saturated di-radical chemical group containing only carbon and hydrogen that is attached to the rest of the molecule via two points of attachment. By way of example only, "$C_1$-$C_{10}$ alkylene" indicates that there are one to ten carbon atoms in the alkylene chain. Non-limiting examples include ethylene and propylene. When an alkylene is interrupted by a ring or ring system described herein, it means the ring or ring system is either inserted into a single covalent bond between two carbon atoms in the alkylene, or the ring or ring system is added to one terminal of the alkylene. For example, when a $C_2$ alkylene is interrupted by a phenylene, it can encompass the following structures: —CH$_2$-Ph-CH$_2$— or -Ph-CH$_2$CH$_2$—.

As used herein, "heteroalkylene" refers to an alkylene group, as defined herein, containing one or more heteroatoms in the carbon back bone (i.e., an alkylene group in which one or more carbon atoms is replaced with a heteroatom, for example, nitrogen atom (N), oxygen atom (S) or sulfur atom (S)). For example, a —CH$_2$— may be replaced with —O—, —S—, or —NH—. Heteroalkylene groups include, but are not limited to ether, thioether, aminoalkylene, and alkylene-amino-alkylene moieties. In some embodiments, the heteroalkylene may include one, two, three, four, or five —CH$_2$CH$_2$O— unit(s). Alternatively and/or additionally, one or more carbon atoms can also be substituted with an oxo (=O) to become a carbonyl. For example, a —CH$_2$— may be replaced with —C(=O)—. It is understood that when a carbon atom is replaced with a carbonyl group, it refers to the replacement of —CH$_2$— with —C(=O)—. When a carbon atom is replaced with a nitrogen atom, it refers to the replacement of —CH— with —N—. When a carbon atom is replaced with an oxygen or sulfur atom, it refers to the replacement of —CH$_2$— with —O— or —S—. When a heteroalkylene is interrupted by a ring or ring system described herein, it means the ring or ring system is either inserted into a single covalent bond (e.g., between two carbon atoms, or between a carbon atom and a heteroatom) in the heteroalkylene, or the ring or ring system is added to one terminal of the heteroalkylene. For example, when a —CH$_2$—O—CH$_2$— is interrupted by a phenylene, it can encompass the following structures: —CH$_2$-Ph-OCH$_2$— or -Ph-CH$_2$OCH$_2$—.

As used herein, "aralkyl" and "(aryl)alkyl" refer to an aryl group, as defined above, connected, as a substituent, via an alkylene group, as described above. The alkylene and aryl group of an aralkyl may be substituted or unsubstituted. Examples include but are not limited to benzyl, 2-phenylalkyl, 3-phenylalkyl, and naphthylalkyl. In some embodiments, the alkylene is an unsubstituted straight chain containing 1, 2, 3, 4, 5, or 6 methylene unit(s).

As used herein, "heteroaralkyl" and "(heteroaryl)alkyl" refer to a heteroaryl group, as defined above, connected, as a substituent, via an alkylene group, as defined above. The alkylene and heteroaryl group of heteroaralkyl may be substituted or unsubstituted. Examples include but are not limited to 2-thienylalkyl, 3-thienylalkyl, furylalkyl, thienylalkyl, pyrrolylalkyl, pyridylalkyl, isoxazolylalkyl, and imidazolylalkyl, and their benzo-fused analogs. In some embodiments, the alkylene is an unsubstituted straight chain containing 1, 2, 3, 4, 5, or 6 methylene unit(s).

As used herein, "(heterocyclyl)alkyl" refer to a heterocyclic or a heterocyclyl group, as defined above, connected, as a substituent, via an alkylene group, as defined above. The alkylene and heterocyclyl groups of a (heterocyclyl)alkyl may be substituted or unsubstituted. Examples include but are not limited to (tetrahydro-2H-pyran-4-yl)methyl, (piperidin-4-yl)ethyl, (piperidin-4-yl)propyl, (tetrahydro-2H-thiopyran-4-yl)methyl, and (1,3-thiazinan-4-yl)methyl. In some embodiments, the alkylene is an unsubstituted straight chain containing 1, 2, 3, 4, 5, or 6 methylene unit(s).

As used herein, "cycloalkylalkyl" and "(cycloalkyl)alkyl" refer to a cycloalkyl group (as defined herein) connected, as a substituent, via an alkylene group. Examples include but are not limited to cyclopropylmethyl, cyclobutylmethyl, cyclopentylethyl, and cyclohexylpropyl. In some embodiments, the alkylene is an unsubstituted straight chain containing 1, 2, 3, 4, 5, or 6 methylene unit(s).

As used herein, "alkoxy" refers to the formula —OR wherein R is an alkyl group, as defined herein. A non-limiting list of alkoxy group includes methoxy, ethoxy, n-propoxy, 1-methylethoxy (isopropoxy), n-butoxy, iso-butoxy, sec-butoxy, and tert-butoxy. An alkoxy may be substituted or unsubstituted.

As used herein, "haloalkyl" refers to an alkyl group in which one or more of the hydrogen atoms are replaced by a halogen (e.g., mono-haloalkyl, di-haloalkyl, and tri-haloalkyl). Such groups include but are not limited to, chloromethyl, fluoromethyl, difluoromethyl, trifluoromethyl and 1-chloro-2-fluoromethyl, 2-fluoroisobutyl. A haloalkyl may be substituted or unsubstituted.

As used herein, "haloalkoxy" refers to an alkoxy group in which one or more of the hydrogen atoms are replaced by a halogen (e.g., mono-haloalkoxy, di-haloalkoxy and tri-haloalkoxy). Such groups include but are not limited to, chloromethoxy, fluoromethoxy, difluoromethoxy, trifluoromethoxy and 1-chloro-2-fluoromethoxy, 2-fluoroisobutoxy. A haloalkoxy may be substituted or unsubstituted.

As used herein, "amino" refer to a —NH$_2$ group. The term "mono-substituted amino group" as used herein refers to an amino (—NH$_2$) group where one of the hydrogen atom is replaced by a substituent. The term "di-substituted amino group" as used herein refers to an amino (—NH$_2$) group where each of the two hydrogen atoms is replaced by a substituent. The term "optionally substituted amino," as used herein refer to a —NR$_A$R$_B$ group where R$_A$ and R$_B$ are independently hydrogen, alkyl, cycloalkyl, aryl, heteroaryl, heterocyclyl, aralkyl, or heterocyclyl(alkyl), as defined herein.

As used herein, "alkylamino" or "(alkyl)amino" refers to a —NR$_A$R$_B$ group where R$_A$ and R$_B$ are hydrogen or alkyl as defined above, and at least one of R$_A$ and R$_B$ is alkyl. The alkyl portion of the (alkyl)amine, includes, for example, C$_1$-C$_6$ alkyl groups.

As used herein, "aminoalkyl" or "(amino)alkyl" refers to an alkyl group in which one or more of the hydrogen atoms are replaced by an amino group or "—NR$_A$R$_B$" group as defined herein. The alkyl portion of the aminoalkyl, includes, for example, C$_1$-C$_6$ alkyl.

The term "halogen atom" or "halogen" as used herein, means any one of the radio-stable atoms of column 7 of the Periodic Table of the Elements, such as, fluorine, chlorine, bromine, and iodine.

As used herein, "alkoxyalkyl" or "(alkoxy)alkyl" refers to an alkoxy group connected via an alkylene group, such as C$_2$-C$_8$ alkoxyalkyl, or (C$_1$-C$_6$ alkoxy)C$_1$-C$_6$ alkyl, for example, —(CH$_2$)$_{1-3}$—OCH$_3$.

As used herein, "—O-alkoxyalkyl" or "—O-(alkoxy)alkyl" refers to an alkoxy group connected via an —O-(alkylene) group, such as —O—(C$_1$-C$_6$ alkoxy)C$_1$-C$_6$ alkyl, for example, —O—(CH$_2$)$_{1-3}$—OCH$_3$.

As used herein, "aryloxy" and "arylthio" refers to RO— and RS—, in which R is an aryl, as defined above, such as but not limited to phenyl. Both an aryloxy and arylthio may be substituted or unsubstituted.

A "sulfenyl" group refers to an "—SR" group in which R can be hydrogen, alkyl, alkenyl, alkynyl, carbocyclyl, aryl, heteroaryl, heterocyclyl, aralkyl, or heterocyclyl(alkyl), as defined above. A sulfenyl may be substituted or unsubstituted.

A "sulfinyl" group refers to an "—S(=O)—R" group in which R can be the same as defined with respect to sulfenyl. A sulfinyl may be substituted or unsubstituted.

A "sulfonyl" group refers to an "SO$_2$R" group in which R can be the same as defined with respect to sulfenyl. A sulfonyl may be substituted or unsubstituted.

An "O-carboxy" group refers to a "RC(=O)O—" group in which R can be hydrogen, alkyl, alkenyl, alkynyl, carbocyclyl, aryl, heteroaryl, heterocyclyl, aralkyl, or heterocyclyl (alkyl), as defined herein. An O-carboxy may be substituted or unsubstituted.

The terms "ester" and "C-carboxy" refer to a "—C(=O)OR" group in which R can be the same as defined with respect to O-carboxy. An ester or C-carboxy may be substituted or unsubstituted.

A "trihalomethanesulfonyl" group refers to an "X$_3$CSO$_2$—" group wherein X is a halogen.

A "trihalomethanesulfonamido" group refers to an "X$_3$CS(O)$_2$N(R)—" group wherein X is a halogen and R is be hydrogen, alkyl, alkenyl, alkynyl, carbocyclyl, aryl, heteroaryl, heterocyclyl, aralkyl, or heterocyclyl(alkyl), as defined herein.

A "mercapto" group refers to an "—SH" group.

An "S-sulfonamido" group refers to a "—SO$_2$N(R$_A$R$_B$)" group in which R$_A$ and R$_B$ can be independently hydrogen, alkyl, alkenyl, alkynyl, carbocyclyl, aryl, heteroaryl, heterocyclyl, aralkyl, or heterocyclyl(alkyl) as defined herein. An S-sulfonamido may be substituted or unsubstituted.

An "N-sulfonamido" group refers to a "RSO$_2$N(R$_A$)—" group in which R and R$_A$ can be independently hydrogen, alkyl, alkenyl, alkynyl, carbocyclyl, aryl, heteroaryl, heterocyclyl, aralkyl, or heterocyclyl(alkyl), as defined herein. An N-sulfonamido may be substituted or unsubstituted.

An "O-carbamyl" group refers to a "—OC(=O)N(R$_A$R$_B$)" group in which R$_A$ and R$_B$ can be the same as defined with respect to S-sulfonamido. An O-carbamyl may be substituted or unsubstituted.

An "N-carbamyl" group refers to an "ROC(=O)N(R$_A$)—" group in which R and R$_A$ can be the same as defined with respect to N-sulfonamido. An N-carbamyl may be substituted or unsubstituted.

An "O-thiocarbamyl" group refers to a "—OC(=S)—N(R$_A$R$_B$)" group in which R$_A$ and R$_B$ can be the same as defined with respect to S-sulfonamido. An O-thiocarbamyl may be substituted or unsubstituted.

An "N-thiocarbamyl" group refers to an "ROC(=S)N(R$_A$)—" group in which R and R$_A$ can be the same as defined with respect to N-sulfonamido. An N-thiocarbamyl may be substituted or unsubstituted.

A "C-amido" group refers to a "—C(=O)N(R$_A$R$_B$)" group in which R$_A$ and R$_B$ can be the same as defined with respect to S-sulfonamido. A C-amido may be substituted or unsubstituted.

An "N-amido" group refers to a "RC(=O)N(R$_A$)—" group in which R and R$_A$ can be the same as defined with respect to N-sulfonamido. An N-amido may be substituted or unsubstituted.

Where the numbers of substituents is not specified (e.g., haloalkyl), there may be one or more substituents present. For example, "haloalkyl" may include one or more of the same or different halogens.

It is understood that, in any compound described herein having one or more chiral centers, if an absolute stereochemistry is not expressly indicated, then each center may independently be of R-configuration or S-configuration or a mixture thereof. Thus, the compounds provided herein may be enantiomerically pure, enantiomerically enriched, or may be stereoisomeric mixtures, and include all diastereomeric and enantiomeric forms. In addition, it is understood that, in any compound described herein having one or more double bond(s) generating geometrical isomers that can be defined as E or Z, each double bond may independently be E or Z a mixture thereof. Stereoisomers are obtained, if desired, by methods such as, stereoselective synthesis and/or the separation of stereoisomers by chiral chromatographic columns. Likewise, it is understood that, in any compound described, all tautomeric forms are also intended to be included.

Wherever a substituent is depicted as a di-radical (i.e., has two points of attachment to the rest of the molecule), it is to be understood that the substituent can be attached in any directional configuration unless otherwise indicated. Thus, for example, a substituent depicted as -AE- or

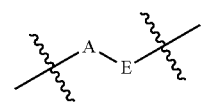

includes the substituent being oriented such that the A is attached at the leftmost attachment point of the molecule as well as the case in which A is attached at the rightmost attachment point of the molecule. In addition, if a group or substituent is depicted as

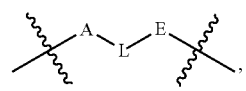

and when L is defined as a bond or absent; such group or substituent is equivalent to

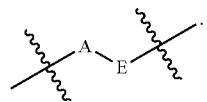

It is to be understood that where compounds disclosed herein have unfilled valencies, then the valencies are to be filled with hydrogens and/or deuteriums.

It is understood that the compounds described herein can be labeled isotopically or by another other means, including, but not limited to, the use of chromophores or fluorescent moieties, bioluminescent labels, or chemiluminescent labels. Substitution with isotopes such as deuterium may afford certain therapeutic advantages from greater metabolic stability, such as, for example, increased in vivo half-life or reduced dosage requirements. Each chemical element as represented in a compound structure may include any isotope of said element. For example, in a compound structure a hydrogen atom may be explicitly disclosed or understood to be present in the compound. At any position of the compound that a hydrogen atom may be present, the hydrogen atom can be any isotope of hydrogen, including but not limited to hydrogen-1 (protium), hydrogen-2 (deuterium), and hydrogen-3 (tritium). Thus, reference herein to a compound encompasses all potential isotopic forms unless the context clearly dictates otherwise.

Likewise, it is understood that the compounds described herein, such as compounds of preferred embodiments, include the compound in any of the forms described herein (e.g., pharmaceutically acceptable salts, crystalline forms, amorphous form, solvated forms, enantiomeric forms, tautomeric forms, and the like). Furthermore, it is understood that the word "polymer" includes homo-polymers, co-polymers, crosslinked homo-polymers and crosslinked co-polymers, etc.

As used herein, the abbreviations for any protective groups, amino acids and other compounds, are, unless indicated otherwise, in accord with their common usage, recognized abbreviations, or the IUPAC-IUB Commission on Biochemical Nomenclature (See, *Biochem.* 11:942-944 (1972)).

The terms "protecting group" and "protecting groups" as used herein refer to any atom or group of atoms that is added to a molecule in order to prevent existing groups in the molecule from undergoing unwanted chemical reactions. Examples of protecting group moieties are described in T. W. Greene and P. G. M. Wuts, *Protective Groups in Organic Synthesis,* 3. Ed. John Wiley & Sons, 1999, and in J. F. W. McOmie, *Protective Groups in Organic Chemistry* Plenum Press, 1973, both of which are hereby incorporated by reference for the limited purpose of disclosing suitable protecting groups. The protecting group moiety may be chosen in such a way, that they are stable to certain reaction conditions and readily removed at a convenient stage using methodology known from the art. A non-limiting list of protecting groups include benzyl (Bn); substituted benzyl; alkylcarbonyls (e.g., t-butoxycarbonyl (BOC), acetyl (i.e., —C(=O)CH₃ or Ac), or isobutyryl (iBu); arylalkylcarbonyls (e.g., benzyloxycarbonyl or benzoyl (i.e., —C(=O)Ph or Bz)); substituted methyl ether (e.g., methoxymethyl ether (MOM)); substituted ethyl ether (e.g., methoxyethyl ether (MOE); a substituted benzyl ether; tetrahydropyranyl ether; silyl ethers (e.g., trimethylsilyl (TMS), triethylsilyl, triisopropylsilyl, t-butyldimethylsilyl (TBDMS), tri-iso-propylsilyloxymethyl (TOM), or t-butyldiphenylsilyl); esters (e.g., benzoate ester); carbonates (e.g., methoxymethylcarbonate); sulfonates (e.g., tosylate or mesylate); acyclic ketal (e.g., dimethyl acetal); cyclic ketals (e.g., 1,3-dioxane or 1,3-dioxolanes); acyclic acetal; cyclic acetal; acyclic hemiacetal; cyclic hemiacetal; cyclic dithioketals (e.g., 1,3-dithiane or 1,3-dithiolane); and triarylmethyl groups (e.g., trityl; monomethoxytrityl (MMTr); 4,4'-dimethoxytrityl (DMTr); or 4,4',4"-trimethoxytrityl (TMTr)).

The term "leaving group" as used herein refers to any atom or moiety that is capable of being displaced by another atom or moiety in a chemical reaction. More specifically, in some embodiments, "leaving group" refers to the atom or moiety that is displaced in a nucleophilic substitution reaction. In some embodiments, "leaving groups" are any atoms or moieties that are conjugate bases of strong acids. Examples of suitable leaving groups include, but are not limited to, tosylates and halogens. Non-limiting characteristics and examples of leaving groups can be found, for example in *Organic Chemistry,* 2d ed., Francis Carey (1992), pages 328-331; *Introduction to Organic Chemistry,* 2d ed., Andrew Streitwieser and Clayton Heathcock (1981), pages 169-171; and *Organic Chemistry,* 5$^{th}$ ed., John McMurry (2000), pages 398 and 408; all of which are incorporated herein by reference for the limited purpose of disclosing characteristics and examples of leaving groups.

The term "pharmaceutically acceptable salt" as used herein is a broad term, and is to be given its ordinary and customary meaning to a person of ordinary skill in the art (and is not to be limited to a special or customized meaning), and refers without limitation to a salt of a compound that does not cause significant irritation to an organism to which it is administered and does not abrogate the biological activity and properties of the compound. In some embodiments, the salt is an acid addition salt of the compound. Pharmaceutical salts can be obtained by reacting a compound with inorganic acids such as hydrohalic acid (e.g., hydrochloric acid or hydrobromic acid), sulfuric acid, nitric acid, and phosphoric acid. Pharmaceutical salts can also be obtained by reacting a compound with an organic acid such as aliphatic or aromatic carboxylic or sulfonic acids, for example formic acid, acetic acid (AcOH), propionic acid, glycolic acid, pyruvic acid, malonic acid, maleic acid, fumaric acid, trifluoroacetic acid (TFA), benzoic acid, cinnamic acid, mandelic acid, succinic acid, lactic acid, malic acid, tartaric acid, citric acid, ascorbic acid, nicotinic acid, methanesulfonic acid, ethanesulfonic acid, p-toluensulfonic acid, salicylic acid, stearic acid, muconic acid, butyric acid, phenylacetic acid, phenylbutyric acid, valproic acid, 1,2-ethanedisulfonic acid, 2-hydroxyethanesulfonic acid, benzenesulfonic acid, 2-naphthalenesulfonic acid, or naphthalenesulfonic acid. Pharmaceutical salts can also be obtained by reacting a compound with a base to form a salt such as an ammonium salt, an alkali metal salt, such as a lithium, sodium or a potassium salt, an alkaline earth metal salt, such as a calcium, magnesium or aluminum salt, a salt of organic bases such as dicyclohexylamine, N-methyl-D-glucamine, tris(hydroxymethyl)methylamine, ($C_1$-$C_7$ alkyl)amine, cyclohexylamine, dicyclohexylamine, triethanolamine, ethylenediamine, ethanolamine, diethanolamine, triethanolamine, tromethamine, and salts with amino acids such as arginine and lysine; or a salt of an inorganic base, such as aluminum hydroxide, calcium hydroxide, potassium hydroxide, sodium carbonate, sodium hydroxide, or the like. In some embodiments, the compounds described herein may be in the form of a trifluoroacetate salt.

As used herein, a "nucleotide" includes a nitrogen containing heterocyclic base, a sugar, and one or more phosphate groups. They are monomeric units of a nucleic acid sequence. In RNA, the sugar is a ribose, and in DNA a deoxyribose, i.e. a sugar lacking a hydroxyl group that is present in ribose. The nitrogen containing heterocyclic base can be purine or pyrimidine base. Purine bases include adenine (A) and guanine (G), and modified derivatives or analogs thereof, such as deazapurine. Pyrimidine bases include cytosine (C), thymine (T), and uracil (U), and modified derivatives or analogs thereof. The C-1 atom of deoxyribose is bonded to N-1 of a pyrimidine or N-9 of a purine.

As used herein, a "nucleoside" is structurally similar to a nucleotide, but is missing the phosphate moieties. An example of a nucleoside analogue would be one in which the label is linked to the base and there is no phosphate group attached to the sugar molecule. The term "nucleoside" is used herein in its ordinary sense as understood by those skilled in the art. Examples include, but are not limited to, a ribonucleoside comprising a ribose moiety and a deoxyribonucleoside comprising a deoxyribose moiety. A modified pentose moiety is a pentose moiety in which an oxygen atom has been replaced with a carbon and/or a carbon has been replaced with a sulfur or an oxygen atom. A "nucleoside" is a monomer that can have a substituted base and/or sugar moiety. Additionally, a nucleoside can be incorporated into larger DNA and/or RNA polymers and oligomers.

The term "purine base" is used herein in its ordinary sense as understood by those skilled in the art, and includes its tautomers. Similarly, the term "pyrimidine base" is used herein in its ordinary sense as understood by those skilled in the art, and includes its tautomers. A non-limiting list of optionally substituted purine-bases includes purine, deazapurine, 7-deazapurine, adenine, 7-deaza adenine, guanine, 7-deaza guanine, hypoxanthine, xanthine, alloxanthine, 7-alkylguanine (e.g. 7-methylguanine), theobromine, caffeine, uric acid and isoguanine. Examples of pyrimidine bases include, but are not limited to, cytosine, thymine, uracil, 5,6-dihydrouracil and 5-alkylcytosine (e.g., 5-methylcytosine).

As used herein, "derivative" or "analogue" means a synthetic nucleoside or nucleotide derivative having modified base moieties and/or modified sugar moieties. Such derivatives and analogs are discussed in, e.g., Scheit, *Nucleotide Analogs* (John Wiley & Son, 1980) and Uhlman et al., *Chemical Reviews* 90:543-584, 1990. Nucleotide analogs can also comprise modified phosphodiester linkages, including phosphorothioate, phosphorodithioate, alkyl-phosphonate, phosphoranilidate, phosphoramidite, and phosphoramidate linkages. "Derivative" and "analog" as used herein, may be used interchangeably, and are encompassed by the terms "nucleotide" and "nucleoside" defined herein.

As used herein, the term "phosphate" is used in its ordinary sense as understood by those skilled in the art, and includes its protonated forms (for example,

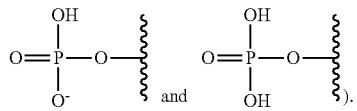

As used herein, the terms "monophosphate," "diphosphate," and "triphosphate" are used in their ordinary sense as understood by those skilled in the art, and include protonated forms.

Polymeric Solid Support

Some embodiments provide a polymer comprising one or more co-monomer repeating units of Formula (I), and (II), and one or more crosslinker repeating units of Formula (III), (IV) or (V) or combinations thereof as described herein:

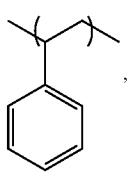 (I)

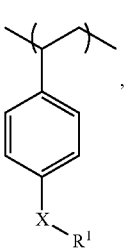 (II)

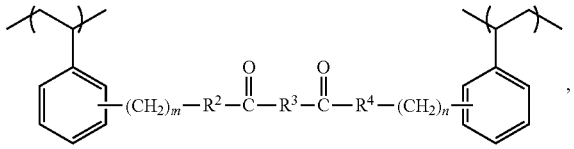 (III)

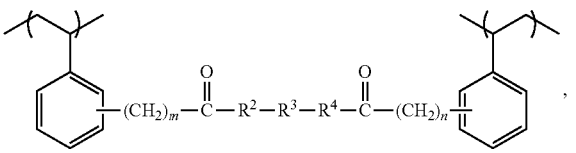 (IV)

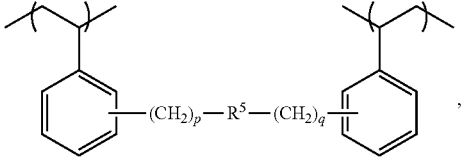 (V)

wherein X is absent or $C_1$-$C_4$ alkylene;

$R^1$ is OH, $NH_2$, OC(=O)$R^a$, or NHC(=O)$R^b$;

each of $R^a$ and $R^b$ is independently optionally substituted $C_1$-$C_6$ alkyl or optionally substituted $C_6$-$C_{10}$ aryl;

each of $R^2$ and $R^4$ is independently —O— or —$NR^c$—;

each $R^c$ is independently H or $C_1$-$C_6$ alkyl;

each $R^3$ is independently optionally substituted $C_6$-$C_{10}$ arylene, optionally substituted $C_3$-$C_{10}$ membered cycloalkylene, optionally substituted five to ten membered heteroarylene, optionally substituted three to ten membered heterocyclylene, optionally substituted $C_1$-$C_{10}$ alkylene, optionally substituted 2 to 1500 membered heteroalkylene, or $C_1$-$C_{10}$ alkylene or 2 to 1500 membered heteroalkylene each independently interrupted by a ring or ring system selected from the group consisting of an optionally substituted $C_6$-$C_{10}$ arylene, optionally substituted $C_3$-$C_{10}$ membered cycloalkylene, optionally substituted five to ten membered heteroarylene, and optionally substituted three to ten membered heterocyclylene;

$R^5$ is a bond, optionally substituted $C_6$-$C_{10}$ arylene, optionally substituted $C_3$-$C_{10}$ membered cycloalkylene, optionally substituted five to ten membered heteroarylene, optionally substituted three to ten membered heterocyclylene, optionally substituted $C_1$-$C_{10}$ alkylene, or optionally substituted 2 to 1500 membered heteroalkylene; and each of m, n, p and q is independently 0, 1, 2, 3, 4, 5 or 6.

In some embodiments of the polymer described herein, the repeating units of Formula (I) and (II) are part of the polymer backbone repeating units. In further embodiments, the polymer may comprise repeating units of Formulas (I), (II) and (III). In other embodiments, the polymer may comprise repeating units of Formulas (I), (II) and (IV). In further embodiments, the polymer may comprise repeating units of Formulas (I), (II) and (V). In further embodiments, the polymer may comprise repeating units of Formulas (I), (II), (III) and (IV). In further embodiments, the polymer may comprise repeating units of Formulas (I), (II), (III) and (V). In further embodiments, the polymer may comprise repeating units of Formulas (I), (II), (IV) and (V). In further embodiments, the polymer may comprise repeating units of Formulas (I), (II), (III), (IV) and (V). In some further embodiments, the polymer is a cross-linked copolymer comprising the structure:

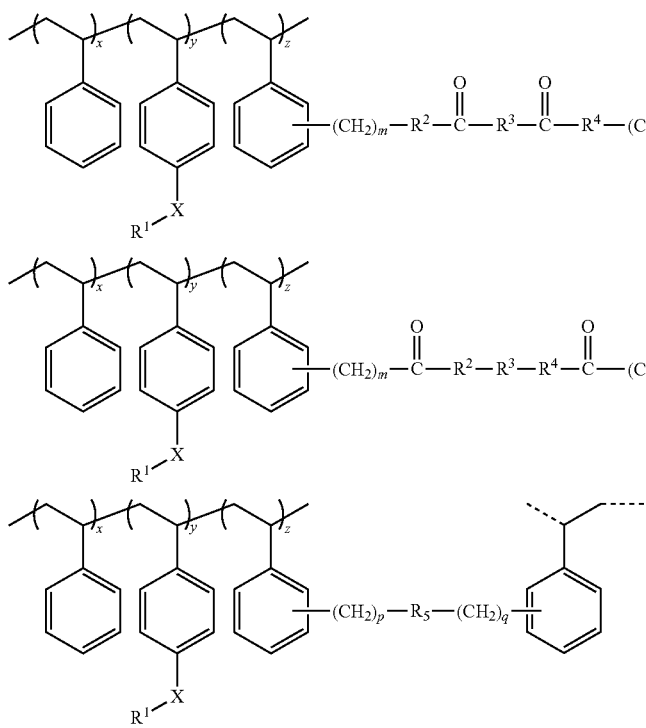

or combinations thereof, wherein x, y, and z are each independently an integer from 1 to about 10000.

In some embodiments of the polymer described herein, X in Formula (II) is absent. In other embodiments, X is $C_1$-$C_4$ alkylene, for example, methylene, ethylene, or propylene. In one embodiment, X is methylene (—$CH_2$—). In some embodiments, $R^1$ is —OC(═O)$R^a$. In some such embodiments, $R^a$ is $C_1$-$C_6$ alkyl, for example, methyl, ethyl, n-propyl, isopropyl, n-butyl, or t-butyl. In another embodiment, $R^1$ is —OH. In another embodiment, $R^1$ is —$NH_2$.

In some embodiments of the polymer described herein, $R^2$ of Formula (III) or (IV) is —O—. In some other embodiments, $R^2$ is —NH—. In some embodiments, $R^4$ of Formula (III) or (IV) is —O—. In some other embodiments, $R^4$ is —NH—. In some embodiments, both of $R^2$ and $R^4$ are —O—. In some other embodiments, both of $R^2$ and $R^4$ are —NH—. In still other embodiments, $R^2$ is —O— and $R^4$ is —NH—. In some further embodiments, $R^4$ is 0 and $R^2$ is —NH—. In some embodiment, each of m and n is independently 0, 1, 2, 3, 4, 5 or 6. In further embodiments, each of m and n is independently 1, 2 or 3. In further embodiment, both of m and n are 1, 2 or 3. In some embodiment, $R^3$ of Formula (III) or (IV) is an optionally substituted $C_6$-$C_{10}$ arylene, an optionally substituted five, six, nine or ten membered heteroarylene, optionally substituted $C_1$-$C_{10}$ alkylene, or optionally substituted 2, 3, 4, or 5 to 1500 membered heteroalkylene. In other embodiments, $R^3$ is optionally substituted $C_3$-$C_{10}$ membered cycloalkylene or optionally substituted three to ten membered heterocyclylene. In other embodiments, $R^3$ is optionally substituted $C_1$-$C_{10}$ alkylene or 2 to 1500 membered heteroalkylene, each independently interrupted by a ring or ring system selected from the group consisting of an optionally substituted $C_6$-$C_{10}$ arylene, optionally substituted $C_3$-$C_{10}$ membered cycloalkylene, optionally substituted five to ten membered heteroarylene, and optionally substituted three to ten membered heterocyclylene. In some further embodiments, each $R^3$ is independently $C_3$, $C_4$, $C_5$, or $C_6$ alkylene. In other embodiments, each $R^3$ is independently an unsubstituted or substituted phenylene. In other embodiments, $R^3$ is an optionally substituted 2, 3, 4, or 5 to 1500 membered heteroalkylene. In further embodiments, $R^3$ is $C_3$, $C_4$, $C_5$, or $C_6$ alkylene interrupted by a phenylene or cycloalkylene (such as cyclopropylene, cyclobutylene, cyclopentylene, or cyclohexylene). In further embodiments, $R^3$ is ($CH_2CH_2O)_k$—$CH_2CH_2$. In further embodiments, k is an integer from 1 to 500.

In some embodiments of the polymer described herein, $R^5$ of Formula (V) is an optionally substituted $C_6$-$C_{10}$ arylene or an optionally substituted five, six, nine or ten membered heteroarylene. In some embodiments, $R^5$ is an unsubstituted or substituted phenylene. In some other embodiments, $R^5$ is a bond. In some other embodiments, $R^5$ is optionally substituted $C_3$-$C_{10}$ membered cycloalkylene (such as cyclopropylene, cyclobutylene, cyclopentylene, or cyclohexylene). or optionally substituted three to ten membered heterocyclylene. In some other embodiments, $R^5$ is $C_1$-$C_6$ alkylene. In some other embodiments, $R^5$ is optionally substituted 2, 3, 4, or 5 to 1500 membered heteroalkylene. In some such embodiments, $R^5$ is $C_2$-$C_{10}$ heteroalkylene comprising one or more oxygen (O) or oxo (═O) atoms. In further embodiments, $R^5$ is —$CH_2OCH_2$—, —$CH_2O(CH_2)_{1-6}OCH_2$—, or —$CH_2O(C$═$O)OCH_2$. In some embodiments, each of p and q is independently 0, 1, 2, 3, 4, 5 or 6. In further embodiments, each of p and q is independently 0, 1, 2 or 3. In some further embodiments, both p and q are 0, 1, 2 or 3. In one embodiment, each of p and q is 1. In another embodiment, both p and q are 0.

In any embodiments of the compounds of Formula (I), (II), (III), (IV) or (V), each phenyl moiety is unsubstituted or substituted with one or more $R^6$, and each $R^6$ is independently selected from the group consisting of halo, cyano, hydroxy, amino, $C_1$-$C_6$ alkyl, $C_1$-$C_6$ haloalkyl, $C_1$-$C_6$ alkoxy, $C_1$-$C_6$ haloalkoxy, ($C_1$-$C_6$ alkyl)amino, ($C_1$-$C_6$ alkyl)hydroxy, ($C_1$-$C_6$ alkoxy)$C_1$-$C_6$ alkyl, and —O—($C_1$-$C_6$ alkoxy)$C_1$-$C_6$ alkyl.

In some embodiments of the polymer described herein, the polymer may comprise one or more repeating units of the following structures:

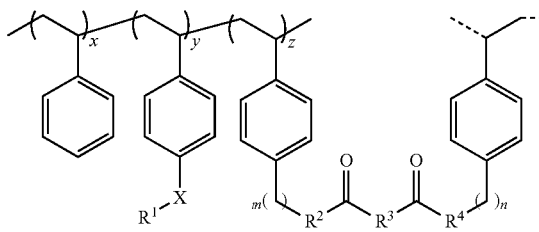

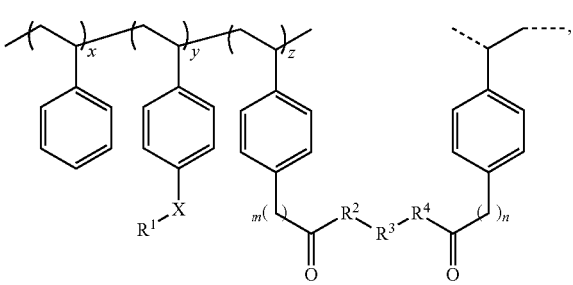

or

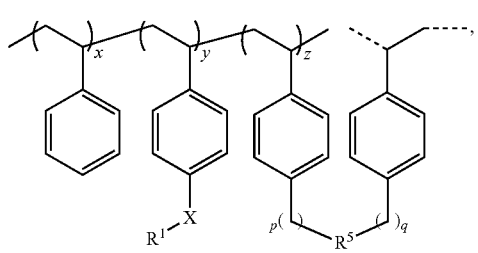

or combinations thereof. In some such embodiments, X is absent or $CH_2$. In some embodiments, $R^1$ is OH or —OC(=O)$CH_3$. In some embodiments, each of $R^2$ and $R^4$ is O or NH. In some embodiments, each $R^3$ is independently $C_1$-$C_6$ alkylene,

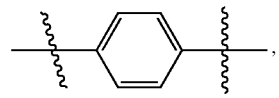

$C_3$-$C_6$ alkylene interrupted by a phenylene, or —($CH_2CH_2O)_k CH_2CH_2$—, and wherein k is an integer from 1 to 5. In some embodiments, $R^5$ is a bond, $C_3$, $C_4$, $C_5$, or $C_6$ alkylene,

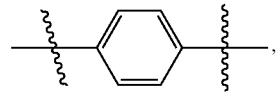

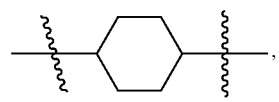

—$CH_2OCH_2$—, —$CH_2O(CH_2)_{1-6}OCH_2$—, —$O(CH_2)_{1-6}O$—, or —$CH_2O(C=O)OCH_2$—. In some further embodiments, each of m and n is independently 0 or 1. In one embodiment, both m and n are 1. In another embodiment, both m and n are 0. In some further embodiments, each of p and q is independently 0 or 1. In one embodiment, both p and q are 1. In another embodiment, both p and q are 0.

In some embodiments of the polymer described herein, the dash lines extended from the right side of the phenyl moiety in each of the structure means that such phenyl moiety may be further connected to other repeating units demonstrated on the left side of the structure, for example:

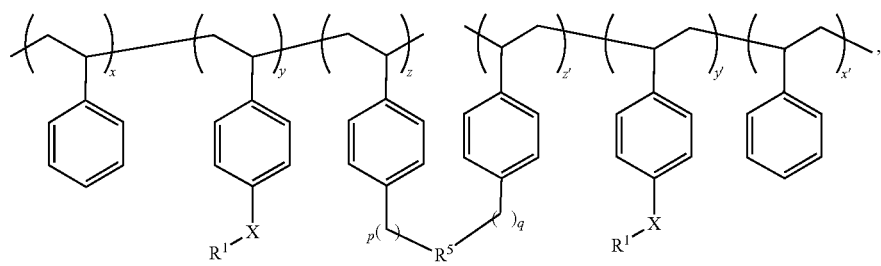

where x', y', and z' are each independently an integer from 1 to about 10000.

In any embodiments of the polymer described herein, heteroarylene or heterocyclylene may containing one, two or three heteroatoms selected from N, O and S. Heteroarylene may be five, six, nine or ten membered. Heterocyclylene may be four, five, six, or seven membered.

In any embodiments of the polymer described herein, the polymer may be in the form of porous polymeric beads. In some such embodiments, the porous polymeric beads have a loading capacity of from about 10 μmol to about 600 μmol, from about 20 μmol to about 500 μmol, from about 30 μmol to about 400 μmol, or from about 40 μmol to about 300 μmol, per gram of beads. In some further embodiments, the porous polymeric bead has a loading capacity of about 10 μmol, 20 μmol, 30 μmol, 40 μmol, 50 μmol, 60 μmol, 70 μmol, 80 μmol, 90 μmol, 100 μmol, 150 μmol, 200 μmol, 250 μmol, 300 μmol, 350 μmol, 400 μmol, 450 μmol, 500 μmol, 550 μmol or 600 μmol per gram of beads, or a range defined by any two of the preceding values.

In some embodiments of polymeric beads described herein, the polymeric beads have an average particle size from about 5 μm to about 600 μm, from about 10 μm to about 500 μm, from about 20 μm to about 400 μm, or from about 50 μm to about 300 μm. In further embodiments, the polymeric beads have an average particle size from about 20 μm to 100 μm. In some embodiment, the porous polymeric beads have an average particle size of about 5 μm, 10 μm, 20 μm, 30 μm, 40 μm, 50 μm, 60 μm, 70 μm, 80 μm, 90 μm, 100 μm, 110 μm, 120 μm, 125 μm, 130 μm, 140 μm, 150 μm, 175 μm, 200 μm, 225 μm, 250 μm, 275 μm, 300 μm, 325 μm, 350 μm, 375 μm or 400 μm, or in a range defined by any two of the preceding values. In some embodiments, the porous polymeric beads have an average particle size greater than about 50, 55, 60, 65, or 75 μm. In some embodiments, the porous polymeric beads have an average particle size ranging from about 70 μm to about 120 μm.

In some embodiments of the porous polymeric beads described herein, the polymeric beads have an average pore size from about 10 nm to about 200 nm, from about 20 nm to about 175 nm, from about 30 nm to about 150 nm, from about 40 nm to about 125 nm, or from about 50 nm to about 100 nm. In some further embodiments, the polymeric bead has an average pore size of about 10 nm, 20 nm, 30 nm, 40 nm, 50 nm, 60 nm, 70 nm, 80 nm, 90 nm, 100 nm, 120 nm, 140 nm, 160 nm, 180 nm or 200 nm, or a range defined by any two of the proceeding values.

Additional embodiments of the polymeric beads include those prepared by the process described herein.

Processes of Producing Porous Polymeric Beads

Some embodiments of the present application relate to a process for preparing porous polymeric beads, comprising:

copolymerizing a styrene monomer, an acetoxymethyl styrene or acetoxy styrene monomer, and one or more crosslinker monomers of Formula (VI), (VII) or (VIII) or a combination thereof, to provide a crosslinked copolymer; and hydrolyzing the crosslinked copolymer to convert the acetoxymethyl or acetoxy group to hydroxymethyl or hydroxy group in the crosslinked copolymer;

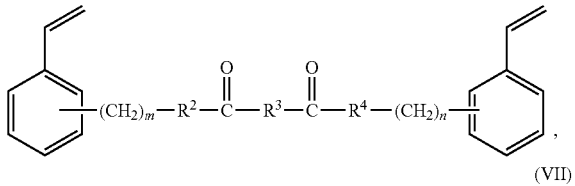

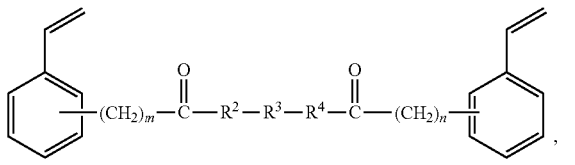

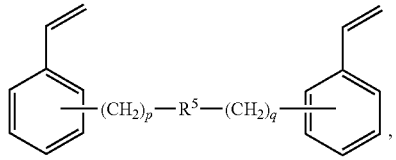

wherein each of $R^2$ and $R^4$ is independently —O— or —$NR^c$—;

each $R^c$ is independently H or $C_1$-$C_6$ alkyl;

each $R^3$ is independently optionally substituted $C_6$-$C_{10}$ arylene, optionally substituted $C_3$-$C_{10}$ membered cycloalkylene, optionally substituted five to ten membered heteroarylene, optionally substituted three to ten membered heterocyclylene, optionally substituted $C_1$-$C_{10}$ alkylene, optionally substituted 2 to 1500 membered heteroalkylene, or $C_1$-$C_{10}$ alkylene or 2 to 1500 membered heteroalkylene each independently interrupted by a ring or ring system selected from the group consisting of an optionally substituted $C_6$-$C_{10}$ arylene, optionally substituted $C_3$-$C_{10}$ membered cycloalkylene, optionally substituted five to ten membered heteroarylene, and optionally substituted three to ten membered heterocyclylene;

$R^5$ is a bond, optionally substituted $C_6$-$C_{10}$ arylene, optionally substituted $C_3$-$C_{10}$ membered cycloalkylene, optionally substituted five to ten membered heteroarylene, optionally substituted three to ten membered heterocyclylene, optionally substituted $C_1$-$C_{10}$ alkylene, or optionally substituted 2 to 1500 membered heteroalkylene; and each of m, n, p and q is independently 0, 1, 2, 3, 4, 5 or 6.

In some embodiments of the process described herein, the acetoxymethyl styrene is 4-acetoxymethyl styrene

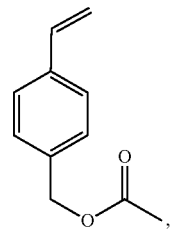

where the phenyl group is unsubstituted or substituted. In some embodiments, the acetoxy styrene monomer is 4-acetoxy styrene

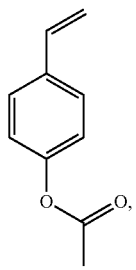

where the phenyl group is unsubstituted or substituted. In further embodiments, the hydrolyzing of the crosslinked copolymer converts the acetoxymethyl group to hydroxymethyl group

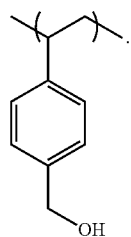

In further embodiments, the hydrolyzing of the crosslinked copolymer converts the acetoxy group to hydroxy group

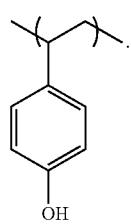

In some embodiments of the process described herein, crosslinker monomer of Formula (VI) is used in the copolymerization. In other embodiments, monomer of Formula (VII) is used in the copolymerization. In other embodiments, monomer of Formula (VIII) is used in the copolymerization. In other embodiments, both monomers of Formula (VI) and Formula (VII) are used. In other embodiments, both monomers of Formula (VI) and Formula (VIII) are used. In other embodiments, both monomers of Formula (VII) and Formula (VIII) are used. In other embodiments, all monomers of Formulas (VI), (VII) and (VIII) are used. In further embodiments, crosslinker monomer of Formula (VI) can also have the structure:

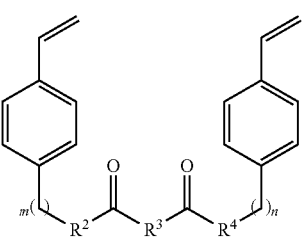

In further embodiments, crosslinker monomer of Formula (VII) can also have the structure:

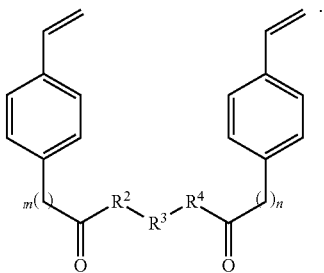

In further embodiments, crosslinker monomer of Formula (VIII) can also have the structure:

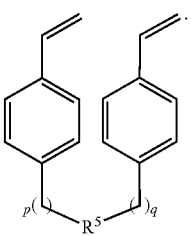

In some embodiments of the process described herein, $R^2$ of Formula (VI) or (VII) is —O—. In some other embodiments, $R^2$ is —NH—. In some embodiments, $R^4$ of Formula (VI) or (VII) is —O—. In some other embodiments, $R^4$ is —NH—. In some embodiments, both of $R^2$ and $R^4$ are —O—. In some other embodiments, both of $R^2$ and $R^4$ are —NH—. In still other embodiments, $R^2$ is —O— and $R^4$ is —NH—. In some further embodiments, $R^4$ is —O— and $R^2$ is —NH—. In some embodiment, each of m and n is independently 0, 1, 2, 3, 4, 5 or 6. In further embodiments, each of m and n is independently 1, 2 or 3. In further embodiment, both of m and n are 1, 2 or 3. In some embodiment, $R^3$ of Formula (VI) or (VII) is an optionally substituted $C_6$-$C_{10}$ arylene, an optionally substituted five, six, nine or ten membered heteroarylene, optionally substituted $C_1$-$C_{10}$ alkylene, or optionally substituted 2, 3, 4, or 5 to 1500 membered heteroalkylene. In other embodiments, $R^3$ is optionally substituted $C_3$-$C_{10}$ membered cycloalkylene or optionally substituted three to ten membered heterocyclylene. In other embodiments, $R^3$ is optionally substituted $C_1$-$C_{10}$ alkylene or 2 to 1500 membered heteroalkylene, each independently interrupted by a ring or ring system selected from the group consisting of an optionally substituted $C_6$-$C_{10}$ arylene, optionally substituted $C_3$-$C_{10}$ membered cycloalkylene, optionally substituted five to ten membered heteroarylene, and optionally substituted three to ten membered heterocyclylene. In some further embodiments, each $R^3$ is independently $C_3$, $C_4$, $C_5$, or $C_6$ alkylene. In other embodiments, each $R^3$ is independently an unsubstituted or substituted phenylene. In other embodiments, $R^3$ is an optionally substituted 2, 3, 4, or 5 to 1500 membered heteroalkylene. In further embodiments, $R^3$ is $C_3$, $C_4$, $C_5$, or $C_6$ alkylene interrupted by a phenylene or cycloalkylene (such as cyclopropylene, cyclobutylene, cyclopentylene, or cyclohexylene). In further embodiments, $R^3$ is $(CH_2CH_2O)_k$—$CH_2CH_2$. In further embodiments, k is an integer from 1 to 500. Non-limiting examples of the crosslinker monomer of Formula (VI) or (VII) include:

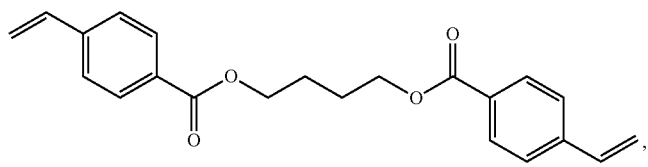
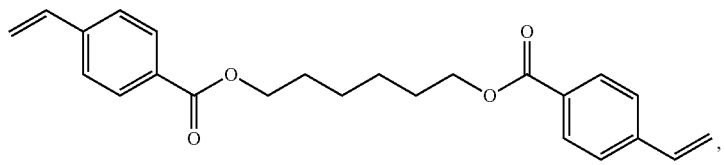
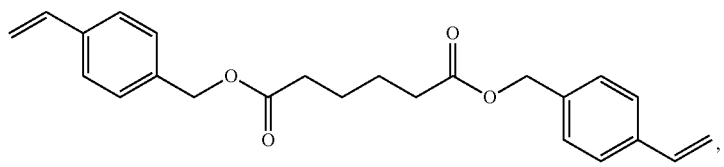
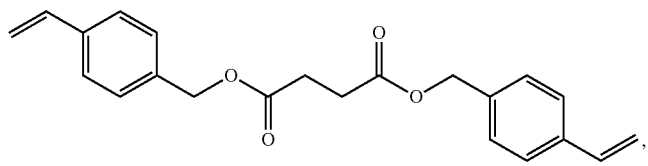
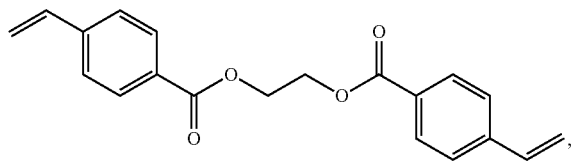
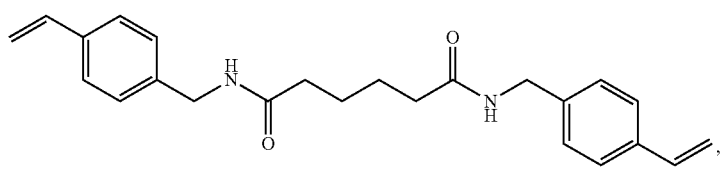
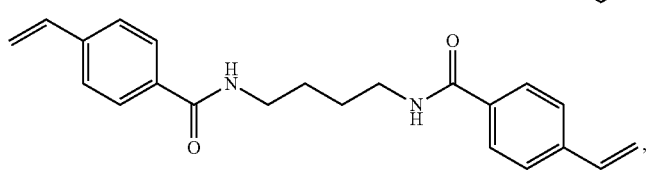
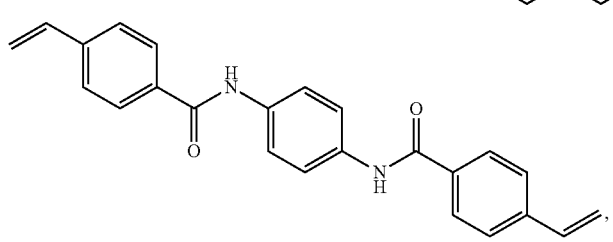
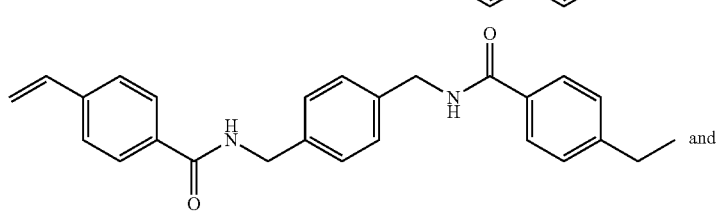

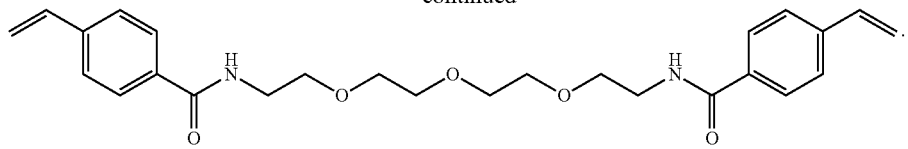

In some embodiments of the polymer described herein, $R^5$ of Formula (VIII) is an optionally substituted $C_6$-$C_{10}$ arylene or an optionally substituted five, six, nine or ten membered heteroarylene. In some embodiments, $R^5$ is an unsubstituted or substituted phenylene. In some other embodiments, $R^5$ is a bond. In some other embodiments, $R^5$ is optionally substituted $C_3$-$C_{10}$ membered cycloalkylene (such as cyclopropylene, cyclobutylene, cyclopentylene, or cyclohexylene). or optionally substituted three to ten membered heterocyclylene. In some other embodiments, $R^5$ is $C_1$-$C_6$ alkylene. In some other embodiments, $R^5$ is optionally substituted 2, 3, 4, or 5 to 1500 membered heteroalkylene. In some such embodiments, $R^5$ is $C_2$-$C_{10}$ heteroalkylene comprising one or more oxygen (O) or oxo (=O) atoms. In further embodiments, $R^5$ is —$CH_2OCH_2$—, —$CH_2O(CH_2)_{1-6}OCH_2$—, or —$CH_2O(C=O)OCH_2$—. In some embodiments, each of p and q is independently 0, 1, 2, 3, 4, 5 or 6. In further embodiments, each of p and q is independently 0, 1, 2 or 3. In some further embodiments, both p and q are 0, 1, 2 or 3. In one embodiment, each of p and q is 1. In another embodiment, both p and q are 0. Non-limiting examples of the crosslinker monomer of Formula (VIII) include:

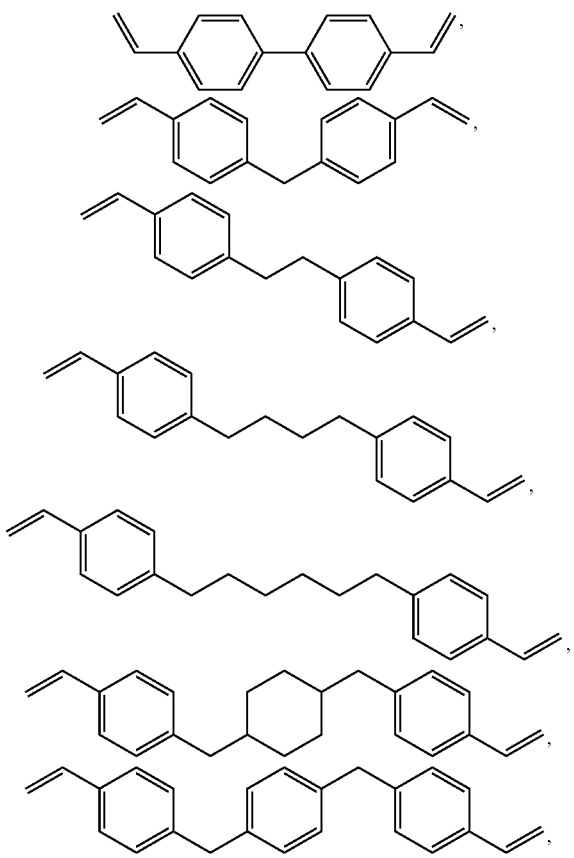

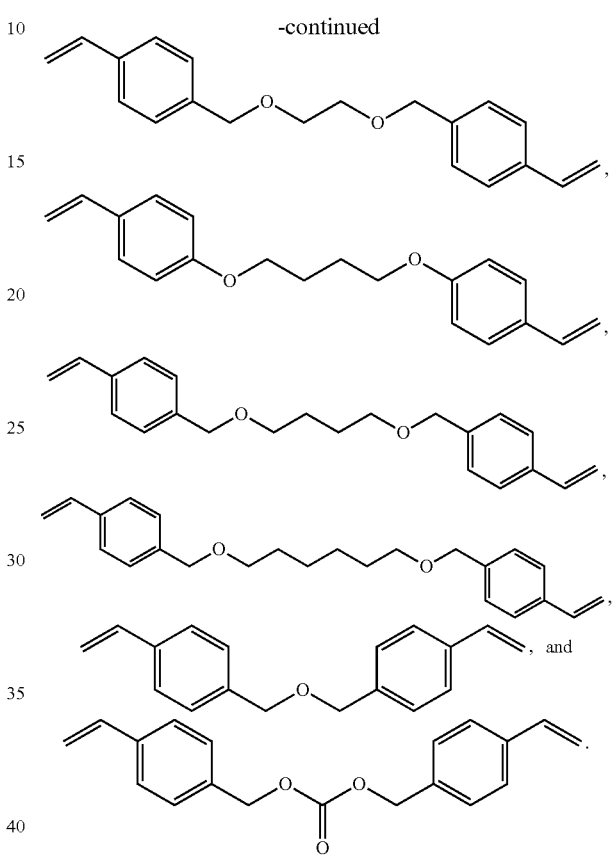

In some embodiments of the process described herein, each phenyl moiety in the monomer of Formula (VI), (VII) or (VIII) is optionally substituted with one or more $R^6$, and each $R^6$ is independently selected from the group consisting of halo, cyano, hydroxy, amino, $C_1$-$C_6$ alkyl, $C_1$-$C_6$ haloalkyl, $C_1$-$C_6$ alkoxy, $C_1$-$C_6$ haloalkoxy, ($C_1$-$C_6$ alkyl)amino, ($C_1$-$C_6$ alkyl)hydroxy, ($C_1$-$C_6$ alkoxy)$C_1$-$C_6$ alkyl, and —O—($C_1$-$C_6$ alkoxy)$C_1$-$C_6$ alkyl.

In any embodiments of the process described herein, heteroarylene or heterocyclylene may containing one, two or three heteroatoms selected from N, O and S. Heteroarylene may be five, six, nine or ten membered. Heterocyclylene may be four, five, six, or seven membered.

In some embodiments of the process described herein, the amount of styrene monomer present in the total amount of monomers is from about 20 wt % to about 90 wt %, from about 30 wt % to about 85 wt %, from about 40 wt % to about 80 wt %, from about 50 wt % to about 70 wt %, from about 60 wt % to about 80 wt %, from about 70 wt % to about 90 wt %, from about 80 wt % to about 95 wt %. In some embodiments, the amount of styrene monomer present in the total amount of monomers is about 20 wt %, 25 wt %, 30 wt %, 35 wt %, 40 wt %, 45 wt %, 50 wt %, 55 wt %, 60 wt %, 65 wt %, 70 wt %, 75 wt %, 80 wt %, 85 wt %, 90 wt %, or 95 wt %, or in a range defined by any two of the preceding values. In some such embodiments, the amount of styrene monomer refers to the initial amount of styrene present in the total amount of monomers at the beginning of the copolymerization step.

In some embodiments of the process described herein, the amount of acetoxymethyl or acetoxy styrene monomer (e.g., 4-acetoxymethyl or 4-acetoxy styrene monomer) present in the total amount of monomers is from about 1 wt % to about 30 wt %, for example, from about 1 wt % to about 5 wt %, from about 5 wt % to about 10 wt %, from about 10 wt % to about 15 wt %, from about 15 wt % to about 20 wt %, from about 20 wt % to about 25 wt %, or from about 25 wt % to about 30 wt %. In some embodiments, the amount of acetoxymethyl styrene or acetoxy styrene (such as 4-acetoxymethyl styrene or 4-acetoxy styrene) monomer present in the total amount of monomers is about 1 wt %, 5 wt %, 10 wt %, 15 wt %, 20 wt %, 25 wt %, 30 wt %, 35 wt %, 40 wt %, 45 wt %, 50 wt %, or 55 wt %, or in a range defined by any two of the preceding values. In some such embodiments, the amount of acetoxymethyl or acetoxy styrene monomer refers to the initial amount of acetoxymethyl or acetoxy styrene monomer present in the total amount of monomers at the beginning of the copolymerization step. In some embodiments, after the hydrolysis step, the loading of hydroxyl groups is from about 150 µmol/g to about 500 µmol/g, from about 160 µmol/g to about 400 µmol/g, or from about 170 µmol/g to about 350 µmol/g. In further embodiments, the loading of the hydroxyl groups is about 150, 160, 170, 180, 190, 200, 210, 220, 230, 240, 250, 260, 270, 280, 290, 300, 310, 320, 330, 340, 350, 360, 370, 380, 390, 400, 420, 440, 460, 480 or 500 µmol/g, or a range defined by any two of the preceding values.

In some embodiments of the process described herein, the amount of the crosslinker monomer(s) of Formula (VI), (VII) and/or (VIII) present in the total amount of monomers is from about 1 wt % to about 30 wt %, for example, from about 1 wt % to about 5 wt %, from about 5 wt % to about 10 wt %, from about 10 wt % to about 15 wt %, from about 15 wt % to about 20 wt %, from about 20 wt % to about 25 wt %, or from about 25 wt % to about 30 wt %. In some embodiments, the amount of the crosslinker monomer(s) present in the total amount of monomers is about 1 wt %, 5 wt %, 10 wt %, 15 wt %, 20 wt %, 25 wt %, 30 wt %, 35 wt %, or 40 wt %, or in a range defined by any two of the preceding values. In some such embodiments, the amount of crosslinker monomer of Formula (VI), (VII) and/or (VIII) refers to the initial amount of the crosslinker monomer(s) present in the total amount of monomers at the beginning of the copolymerization step.

In some embodiments of the process described herein, the monomers are dissolved in one or more organic solvents (e.g., porogens) to form an organic phase. For example, the organic solvent may be liquid alkanes, benzene, toluene, xylene, $C_5$ to $C_{12}$ alcohols, 2-ethylhexanol, isooctane, or combinations thereof. In further embodiments, the organic phase also includes one or more polymerization initiators (e.g., thermal polymerization initiator(s)). For example, the polymerization initiators may be benzoyl peroxide. In some embodiments, the copolymerizing includes contacting the organic phase with an aqueous phase comprising water and one or more dispersing agents (i.e., one or more surfactants or emulsifiers) to form an oil-in-water (O/W) emulsion. In further embodiments, the dispersing agents includes a polyalcohol. In yet another embodiment, the polyalcohol is a polyvinyl alcohol. In some further embodiments, the monomer organic solution and/or the aqueous phase also include at least one emulsifier or surfactant. In some embodiments, the crosslinked copolymer obtained in the copolymerization step of the process is also referred to as the first crosslinked copolymer, such first crosslinked copolymer is purified and dried before the hydrolyzing step to convert the acetoxymethyl or acetoxy group in the first crosslinked copolymer to hydroxymethyl or hydroxy group, arriving at a second crosslinked copolymer, which is then used in solid phase synthesis of oligonucleotides.

In some embodiments of the process described herein, the process produces crosslinked copolymer comprising the structure:

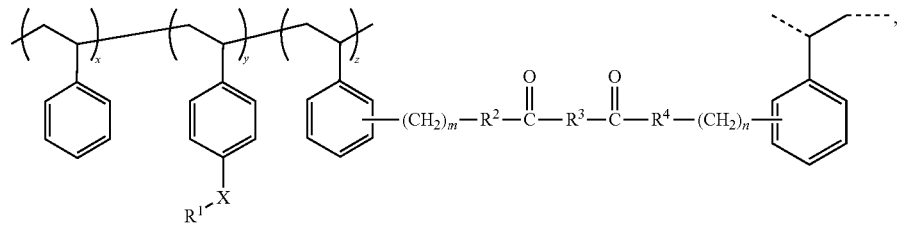

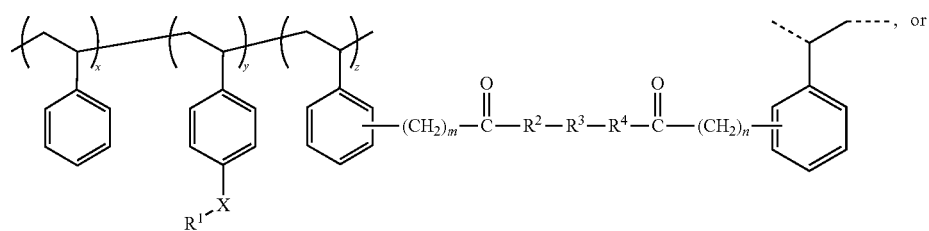

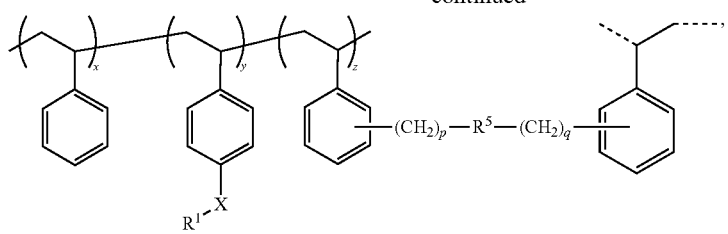

or combinations thereof, wherein R¹ is —OH; and X is absent or —CH$_2$—. In some embodiments, x, y, and z are each independently an integer from 1 to about 10000.

In some further embodiments of the process described herein, the crosslinked copolymer comprises the structure:

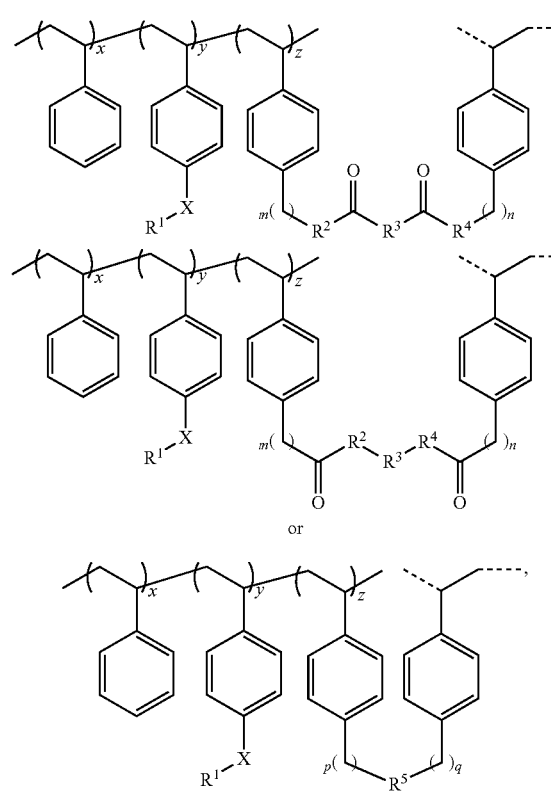

or combinations thereof. In some such embodiments, X is absent or —CH$_2$—. In some embodiments, R¹ is OH or —OC(=O)CH$_3$. In some embodiments, each of R² and R⁴ is O or NH. In some embodiments, each R³ is independently C$_1$-C$_6$ alkylene,

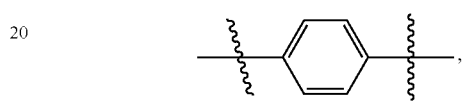

C$_3$-C$_6$ alkylene interrupted by a phenylene, or —(CH$_2$CH$_2$O)$_k$CH$_2$CH$_2$—, and wherein k is an integer from 1 to 5. In some embodiments, R⁵ is a bond, C$_3$, C$_4$, C$_5$, or C$_6$ alkylene,

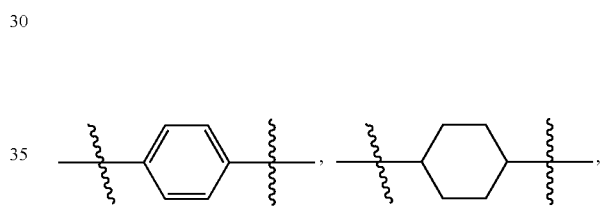

—CH$_2$OCH$_2$—, —CH$_2$O(CH$_2$)$_{1-6}$OCH$_2$—, —O(CH$_2$)$_{1-6}$O—, or —CH$_2$O(C=O)OCH$_2$—. In some further embodiments, each of m and n is independently 0 or 1. In one embodiment, both m and n are 1. In another embodiment, both m and n are 0. In some further embodiments, each of p and q is independently 0 or 1. In one embodiment, both p and q are 1. In another embodiment, both p and q are 0.

In some further embodiments of the process described herein, the dash lines extended from the right side of the phenyl moiety in each of the structure means that such phenyl moiety may be further connected to other repeating units demonstrated on the left side of the structure, for example:

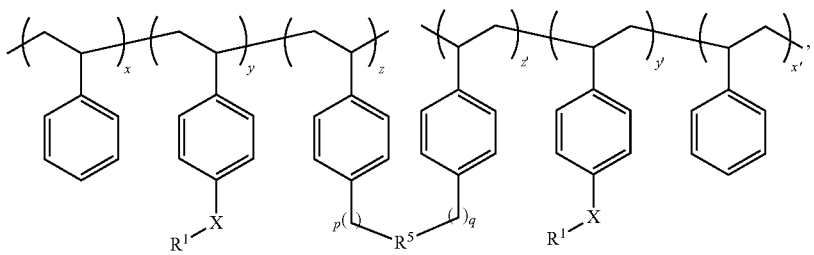

where x', y', and z' are each independently an integer from 1 to about 10000.

In any embodiment of the process described herein, the polymeric beads have an average particle size from about 5 μm to about 600 μm, from about 10 μm to about 500 μm, from about 20 μm to about 400 μm, or from about 50 μm to about 300 μm. In further embodiments, the polymeric bead has a particle size from about 20 μm to 100 μm. In some embodiment, the porous polymeric bead has a particle size of about 5 μm, 10 μm, 20 μm, 30 μm, 40 μm, 50 μm, 60 μm, 70 μm, 80 μm, 90 μm, 100 μm, 125 μm, 150 μm, 175 μm, 200 μm, 225 μm, 250 μm, 275 μm, 300 μm, 325 μm, 350 μm, 375 μm or 400 μm, or in a range defined by any two of the preceding values.

In any embodiment of the process described herein, the polymeric beads have an average pore size from about 10 nm to about 200 nm, from about 20 nm to about 175 nm, from about 30 nm to about 150 nm, from about 40 nm to about 125 nm, or from about 50 nm to about 100 nm. In some further embodiments, the polymeric bead has an average pore size of about 10 nm, 20 nm, 30 nm, 40 nm, 50 nm, 60 nm, 70 nm, 80 nm, 90 nm, 100 nm, 120 nm, 140 nm, 160 nm, 180 nm or 200 nm, or a range defined by any two of the proceeding values.

In any embodiment of the process described herein, the porous polymeric beads have a loading capacity (e.g., as measured by the hydroxy groups) of from about 10 μmol to about 600 μmol, from about 20 μmol to about 500 μmol, from about 30 μmol to about 400 μmol, or from about 40 μmol to about 300 μmol, per gram of beads. In some further embodiments, the porous polymeric bead has a loading capacity of about 10 μmol, 20 μmol, 30 μmol, 40 μmol, 50 μmol, 60 μmol, 70 μmol, 80 μmol, 90 μmol, 100 μmol, 150 μmol, 200 μmol, 250 μmol, 300 μmol, 350 μmol, 400 μmol, 450 μmol, 500 μmol, 550 μmol or 600 μmol per gram of beads, or a range defined by any two of the preceding values. In further embodiments, the loading capacity of the polymeric beads is from about 150 μmol/g to about 500 μmol/g, from about 160 μmol/g to about 400 μmol/g, or from about 170 μmol/g to about 350 μmol/g. There are several parameters that may be adjusted to improve the loading capacity of the beads, including but not limited to: adjusting the pore size and pore size distribution, porosity of the beads, and surface area per gram of beads, increasing the portion of the functional monomers in the copolymerization (i.e., acetoxymethyl styrene or acetoxystyrene); adjusting the cross-linker density; adding more porogen(s); adjusting the porogen type, ratio and/or concentration; decreasing the average particle size of the polymeric beads; and narrowing the particle size distribution of the polymeric beads.

Additional disclosure of the present application includes polymeric beads prepared by the process described herein. In some embodiments, the polymeric beads have a hydroxy group loading capacity of from about 10 μmol to about 600 μmol per gram of beads, more specifically from about 150 μmol/g to about 500 μmol/g, from about 160 μmol/g to about 400 μmol/g, or from about 170 μmol/g to about 350 μmol/g. In some embodiments, the polymeric beads have an average particle size of about 5 μm to about 400 μm, or from about 20 μm to 100 μm.

Compounds of Formula (A1)

Some embodiments of the present application provide a compound of Formula (A1), or a salt thereof as described herein:

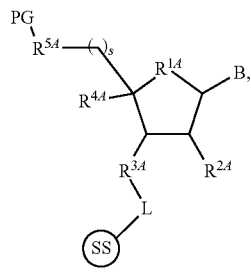

(A1)

wherein:

R$^{1A}$ is O, S, CH$_2$, CFH, CF$_2$, or —CH=CH—;

R$^{2A}$ is H, hydroxy, a protected hydroxy, halogen, —O—(C$_1$-C$_6$ alkyl), or —O—(C$_1$-C$_6$ haloalkyl), or R$^{2A}$ together with R$^{4A}$ forms an optionally substituted C$_3$-C$_{10}$ carbocyclyl or an optionally substituted five to ten membered heterocyclyl;

R$^{3A}$ is O, S, CH$_2$, or NH;

R$^{4A}$ is H, or R$^{4A}$ together with R$^{2A}$ forms an optionally substituted C$_3$-C$_{10}$ carbocyclyl or an optionally substituted five to ten membered heterocyclyl;

R$^{5A}$ is O, S, CH$_2$, or NH;

s is 0 or 1;

B is a natural or modified nucleobase;

PG is H or a removable protecting group;

L is a linking moiety; and

SS is any one of the polymeric beads described herein.

In some embodiments of the compound of Formula (A1), B is a natural nucleobase. In other embodiments, B is a modified natural nucleobase. In other embodiments, B is an unnatural nucleobase. In some embodiments, B is

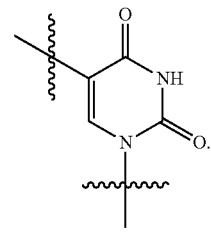 [SMILES: *c1cn(*)c(=O)[nH]c1=O]

In other embodiments, B is

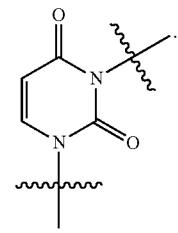 [SMILES: *n1ccc(=O)n(*)c1=O]

In other embodiments, B is

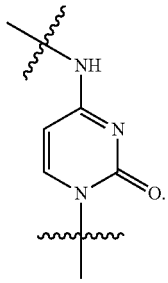 [SMILES: *Nc1ccn(*)c(=O)n1]

In yet other embodiments, B is.

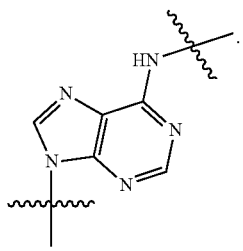 [SMILES: *Nc1ncnc2c1ncn2*]

In still other embodiments, B is

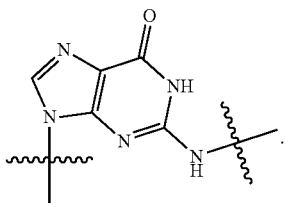 [SMILES: *Nc1nc2c(ncn2*)c(=O)[nH]1]

In some embodiments, B is

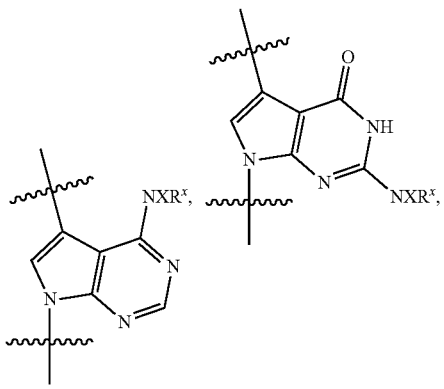

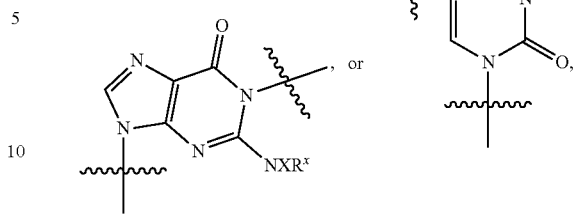

wherein $R^x$ is hydrogen or an amino protecting group, or the hydrogen in —NHR$^x$ is absent and $R^x$ is a divalent amino protecting group. In some embodiments, $R^x$ is —C(=O)C$_{1-6}$ alkyl. For example, in some embodiments, $R^x$ is —C(=O)CH$_3$ (Ac), —C(=O)CH$_2$CH$_3$, or —C(=O)CH(CH$_3$)$_2$ (iBu). In other embodiments, $R^x$ is —C(=O)-phenyl. In some other embodiments, the hydrogen in —NHR$^x$ is absent, and $R^x$ directed attaches to the nitrogen atom form an amino protecting group such as amidine type protecting group or the phthaloyl type protecting group. In some such embodiments, $R^x$ is N,N,-dimethylformamidine

In some other embodiments, $R^x$ is

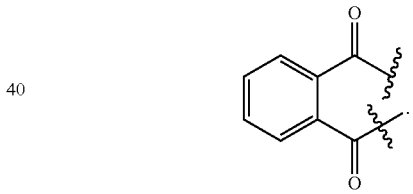

In some embodiments of the compound of Formula (A1), $R^{1A}$ is O, S, CH$_2$, CFH, CF$_2$, or —CH=CH—. In some embodiments, $R^{1A}$ is O. In some embodiments, $R^{1A}$ is S. In some embodiments, $R^{1A}$ is CH$_2$. In some embodiments, $R^{1A}$ is CFH. In some embodiments, $R^{1A}$ is CF$_2$. In some embodiments, $R^{1A}$ is —CH=CH—. In some embodiments, $R^{2A}$ is H, hydroxy, a protected hydroxy, halogen, —O—(C$_1$-C$_6$ alkyl), or —O—(C$_1$-C$_6$ haloalkyl). In some embodiments, $R^{2A}$ is H, hydroxy, or a protected hydroxy. In some embodiments, $R^{2A}$ is H. In some embodiments, $R^{2A}$ is hydroxy. In some embodiments, $R^{2A}$ is a protected hydroxy. In any embodiments of Formula (A1), $R^{2A}$ together with $R^{4A}$ forms an optionally substituted C$_3$-C$_{10}$ carbocyclyl or an optionally substituted five to ten membered heterocyclyl. In some embodiments, $R^{3A}$ is O, S, CH$_2$, or NH. In some embodiments, $R^{3A}$ is O. In some embodiments, $R^{3A}$ is S. In some embodiments, $R^{3A}$ is CH$_2$. In some embodiments, $R^{3A}$ is NH. In some embodiments, $R^{4A}$ is H. In other embodiments, $R^{4A}$ together with $R^{2A}$ forms an optionally substituted C$_3$-C$_{10}$ carbocyclyl or an optionally substituted five to ten membered heterocyclyl. In some embodiments, $R^{5A}$ is O, S, CH$_2$, or NH. In some embodiments, $R^{5A}$ is O. In some embodiments, $R^{5A}$ is S. In some embodiments, $R^{5A}$ is $CH_2$. In some embodiments, $R^{5A}$ is NH. In any embodiment of Formula (A1), s is 0 or 1. In some embodiments, s is 1, $R^{5A}$ is O, and PG is a removable hydroxy protecting group. In some embodiments, PG is a removable hydroxy protecting group. Non-limiting examples of the removable hydroxy protecting groups include A non-limiting list of protecting groups include silyl ethers (e.g., trimethylsilyl (TMS), triethylsilyl, triisopropylsilyl, t-butyldimethylsilyl (TBDMS), tri-iso-propylsilyloxymethyl (TOM), or t-butyldiphenylsilyl); acyclic acetal; cyclic acetal; acyclic hemiacetal; cyclic hemiacetal; and triarylmethyl groups (e.g., trityl; monomethoxytrityl (MMTr); 4,4'-dimethoxytrityl (DMTr); or 4,4',4"-trimethoxytrityl (TMTr)). In one embodiment, PG is DMTr.

In some embodiments of the compound of Formula (A1), the linker moiety L may be a succinate moiety of the structure: —C(=O)—$CH_2$—$CH_2$—C(=O)—, where one carboxy group of the succinic acid forms an ester or amide bond with a functional group on the solid support.

Oligonucleotides of Formula (A2)

Some additional embodiments of the present application relate to a compound of Formula (A2), or a salt thereof as described herein:

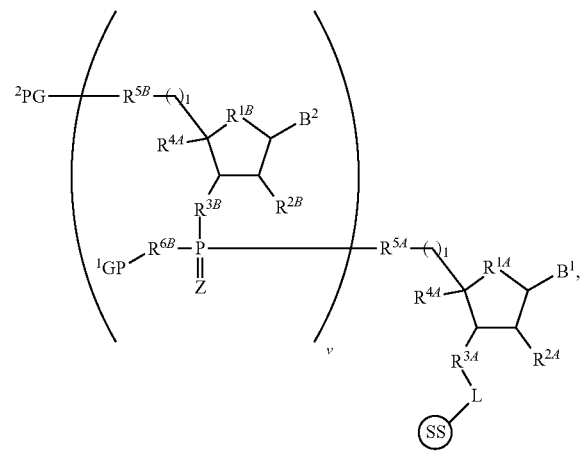

(A2)

wherein:
each of $R^{1A}$ and $R^{1B}$ is independently O, S, $CH_2$, CFH, $CF_2$, or —CH=CH—;
each of $R^{2A}$ and $R^{2B}$ is independently H, hydroxy, a protected hydroxy, halogen, —O—($C_1$-$C_6$ alkyl), or —O—($C_1$-$C_6$ haloalkyl), or $R^{2A}$ together with $R^{4A}$ forms an optionally substituted $C_3$-$C_{10}$ carbocyclyl or an optionally substituted five to ten membered heterocyclyl, or $R^{2B}$ together with $R^{4B}$ forms an optionally substituted $C_3$-$C_{10}$ carbocyclyl or an optionally substituted five to ten membered heterocyclyl;
each of $R^{3A}$ and $R^{3B}$ is independently O, S, $CH_2$, or NH;
each of $R^{4A}$ and $R^{4B}$ is H, or $R^{4A}$ together with $R^{2A}$ forms an optionally substituted $C_3$-$C_{10}$ carbocyclyl or an optionally substituted five to ten membered heterocyclyl, or $R^{4B}$ together with $R^{2B}$ forms an optionally substituted $C_3$-$C_{10}$ carbocyclyl or an optionally substituted five to ten membered heterocyclyl;
each of $R^{5A}$, $R^{5B}$ and $R^{6B}$ is independently O, S, $CH_2$, or NH;

each of s and u is independently 0 or 1;
v is an integer of 1 to 500;
each of $B^1$ and $B^2$ is independently a natural or modified nucleobase;
each of $PG^1$ and $PG^2$ is independently H or a removable protecting group;
Z is O or S;
L is a linking moiety; and
SS is any one of the polymeric beads as described herein.

In some embodiments of the compound of Formula (A2), each of $R^{1A}$ and $R^{1B}$ is independently O, S, $CH_2$, CFH, $CF_2$, or —CH=CH—. In one embodiment, each of $R^{1A}$ and $R^{1B}$ is independently O. In some embodiments, each of $R^{2A}$ and $R^{2B}$ is independently H, hydroxy, a protected hydroxy, halogen, —O—($C_1$-$C_6$ alkyl), or —O—($C_1$-$C_6$ haloalkyl). In some embodiments, each of $R^{2A}$ and $R^{2B}$ is H, hydroxy, or a protected hydroxy. In other embodiments, $R^{2A}$ together with $R^{4A}$ forms an optionally substituted $C_3$-$C_{10}$ carbocyclyl or an optionally substituted five to ten membered heterocyclyl. In other embodiments, $R^{2B}$ together with $R^{4B}$ forms an optionally substituted $C_3$-$C_{10}$ carbocyclyl or an optionally substituted five to ten membered heterocyclyl. In some embodiments, each of $R^{3A}$ and $R^{3B}$ is independently O, S, $CH_2$, or NH. In one embodiment, each of $R^{3A}$ and $R^{3B}$ is O. In some embodiment, each of $R^{4A}$ and $R^{4B}$ is H. In other embodiments, $R^{4A}$ together with $R^{2A}$ forms an optionally substituted $C_3$-$C_{10}$ carbocyclyl or an optionally substituted five to ten membered heterocyclyl. In still other embodiments, $R^{4B}$ together with $R^{2B}$ forms an optionally substituted $C_3$-$C_{10}$ carbocyclyl or an optionally substituted five to ten membered heterocyclyl. In some embodiments, each of $R^{5A}$, $R^{5B}$ and $R^{6B}$ is independently O, S, $CH_2$, or NH. In one embodiment, each of $R^{5A}$, $R^{5B}$ and $R^{6B}$ is O. In some embodiments, each of s and u is independently 0 or 1. In one embodiment, each of s and u is 1. In some embodiments, each of s and u is 1, each of $R^{5A}$, $R^{5B}$ and $R^{6B}$ is O. In some embodiments, Z is O. In some embodiments, Z is S. In some embodiments, v is an integer of 1 to 500, for example 1, 2, 3, 4, 5, 6, 7, 8, 9, 10, 15, 20, 25, 30, 35, 40, 45, 50, 55, 60, 65, 70, 75, 80, 85, 90, 95, 100, 150, or 200.

In some embodiments of the compound of Formula (A2), each of $B^1$ and $B^2$ is independently a natural nucleobase, a modified natural nucleobase, or an unnatural nucleobase. In some embodiments, each of $B^1$ and $B^2$ is

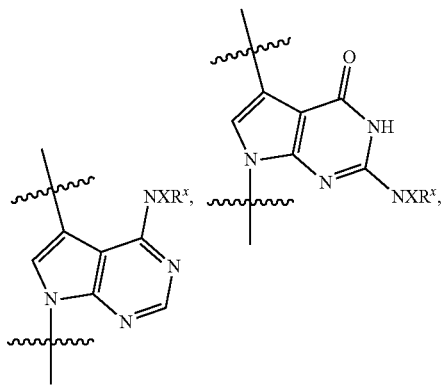

-continued

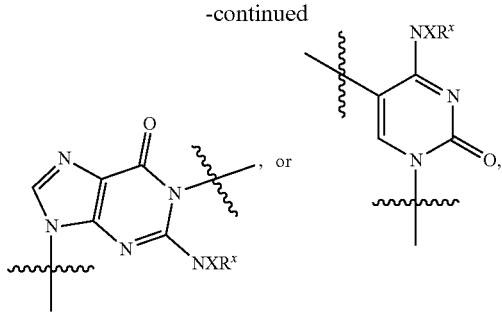

wherein $R^x$ is hydrogen or an amino protecting group, or the hydrogen in —$NHR^x$ is absent and $R^x$ is a divalent amino protecting group. In some embodiments, $R^x$ is —C(=O) $C_{1-6}$ alkyl. For example, in some embodiments, $R^x$ is —C(=O)$CH_3$ (Ac), —C(=O)$CH_2CH_3$, or —C(=O)CH $(CH_3)_2$(iBu). In other embodiments, $R^x$ is —C(=O)-phenyl. In some other embodiments, the hydrogen in —$NHR^x$ is absent and $R^x$ directed attaches to the nitrogen atom form an amino protecting group such as amidine type protecting group or the phthaloyl type protecting group. In some such embodiments, $R^x$ is N,N,-dimethylformamidine

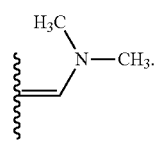

In some other embodiments, $R^x$ is

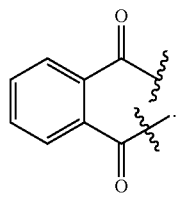 [SMILES: *C(=O)c1ccccc1C(*)=O]

In some embodiments of the compound of Formula (A2), $PG^1$ is H or a removable protecting group. In some embodiments, $PG^1$ is H. In some embodiments, $PG^1$ is

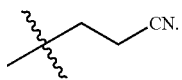

In some embodiments, $PG^2$ is H, a removable hydroxy protecting group, or DMT. In some such embodiments, $PG^2$ is H. In other embodiments, $PG^2$ is a removable hydroxy protecting group, such as those exemplified in the definition of PG of Formula (A1). In some embodiments, $PG^2$ is DMTr.

In some embodiments of the compound of Formula (A2), the linker moiety L may be a succinate moiety of the structure: —C(=O)—$CH_2$—$CH_2$—C(=O)—, where one carboxy group of the succinic acid forms an ester or amide bond with a functional group on the solid support.

EXAMPLES

The following examples, including experiments and results achieved, are provided for illustrative purposes only and are not to be construed as limiting the present application.

Example 1. Acetoxymethyl Styrene Preparation Protocol

To a mixture of 53.42 g of 4-chloromethyl styrene and 39.26 g of potassium acetate, 150 mL of dimethylformamide was added and stirred at 125 rpm with a 2" Teflon blade at 40° C. for 48 hours. The reaction mixture was poured into 500 mL of DI water and the organic layer was separated and saved. The aqueous layer was extracted with three 20-mL of chloroform. The chloroform extract was combined with the organic layer, washed with DI water, and dried over anhydrous calcium chloride. The organic solvent was removed under reduced pressure. To the remaining oil, 40 mg of hydroquinone was added, and vacuum distilled at 68° C. and 0.1 mmHg, producing 51.60 g (82.5% yield) of 4-acetoxymethyl styrene.

Example 2. Crosslinkers of Formula (VI) and (VII) Preparations and Uses

Scheme 1 illustrates the preparation protocol of three crosslinkers of Formula (VI) (crosslinker of Formulas VI-a, VI-b and VI-c), starting with phthalic anhydride and aminomethyl styrene and/or hydroxymethyl styrene. The phthalic anhydride can be replaced by 1,2-benzenedicarboxylic acid, 1,3-benzenedicarboxylic acid or 1,4-benzenedicarboxylic acid.

Scheme 1

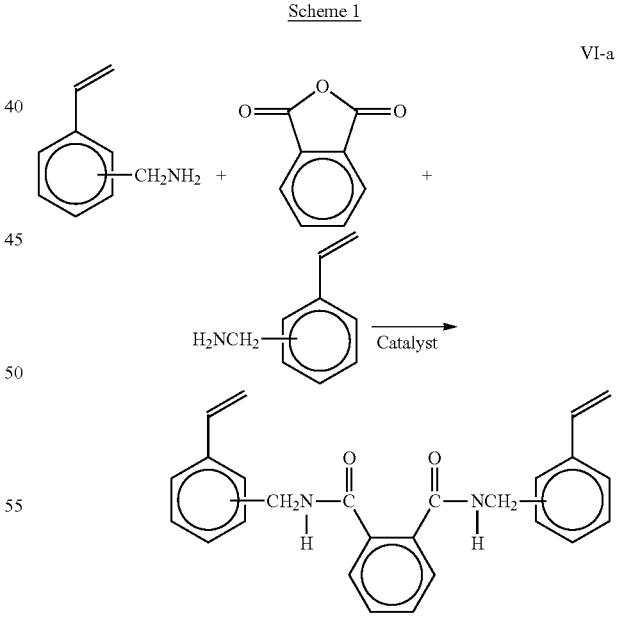

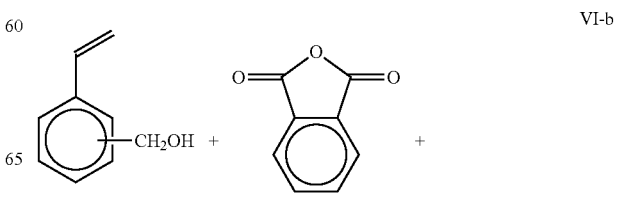

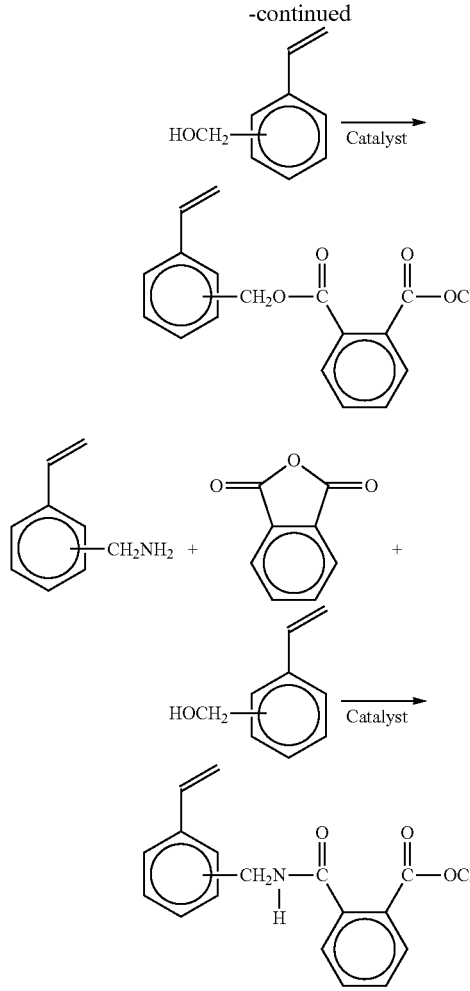

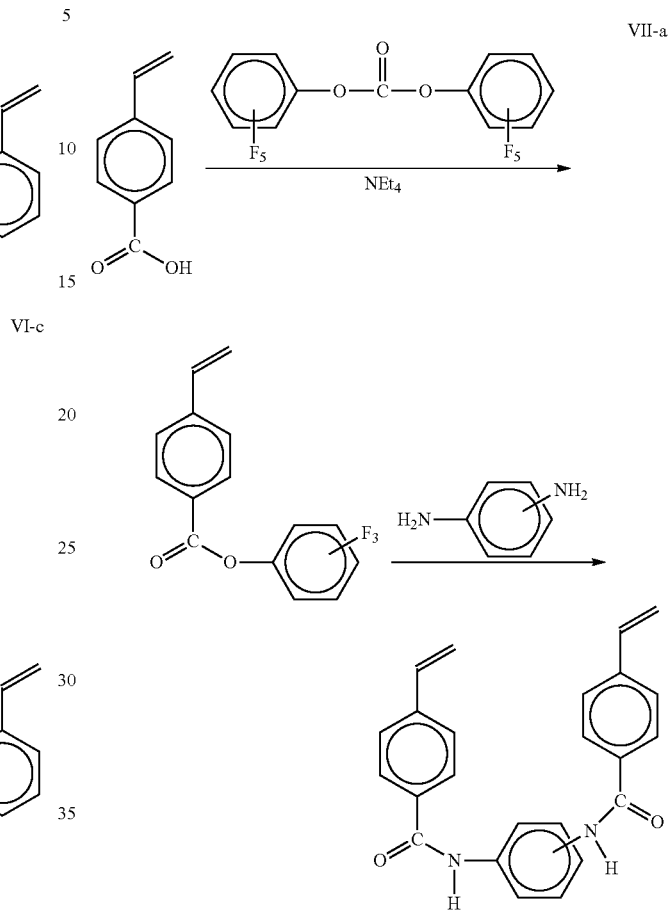

Crosslinker VI-a Preparation Protocol

A mixture of 30.00 g of 4-vinylbenzylamine, 15.00 g of phthalic anhydride, 50 mg of hydroquinone, and 100 mL of dimethylformamide are added and stirred at 125 rpm with a 2" Teflon blade at 35° C. for 18 hours. The reaction mixture is poured into 500 mL of 0.05 M acetic acid with constant stirring at ambient temperature for 15 minutes. The aqueous layer is then discarded. The residual is washed with three 50 mL of 0.1 M acidic acid, producing crosslinker of Formula VI-a. Similar preparation protocols can be applied to the syntheses of crosslinker of Formula VI-b and Formula VI-c.

Scheme 2 illustrates the preparation protocol of one crosslinker of Formula (VII) (crosslinker of Formula VII-a), starting with 4-carboxy styrene and bispentafluorophenyl carbonate. Bispentafluorophenyl carbonate can be replaced by bistetrafluorophenyl carbonate. The catalysts and coupling agents for amidization can be BOPCl, CDI, HATU, HOAT, HOBT, PyBOP, TBTU, TMOS, etc. Alternatively, compound of Formula VII-a can also be prepared by directly reacting 4-carboxy styrene with

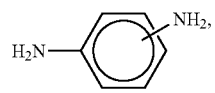

catalyzed by HATU.

Porous, Crosslinked Polystyrene Beads Preparation Protocol with Crosslinker VI-a A 500 mL three-neck round-bottom flask equipped with a heater/cooler, a stirrer and an argon introducing needle is set in a thermostat oil bath. Polyvinyl alcohol (7.1 g) is dissolved in water (373.3 g), and the obtained aqueous solution is placed in the 500 mL three-neck round-bottom flask. A mixed solution of a monomer, porogen and a polymerization initiator is prepared by mixing styrene (16 g), Crosslinker of Formula VI-a (4 g), 2-ethylhexanol (14 g), isooctane (6 g) and benzoyl peroxide (containing 25% of water, 0.4 g). The mixed solution is placed in the 500 mL three-neck round-bottom flask. The mixture is stirred under a room temperature argon stream and heated to 80° C. Suspension polymerization is conducted for 15 hr. The reaction product is cooled, filtered, and the residue is washed and dried to give porous microparticles. The obtained particles have a particle size from about 20 μm to about 100 μm. Agglomerate particles are not found.

Schemes 3A-3F illustrate the preparation protocol of six crosslinkers of Formula (VII) (VII-1, VII-2, VII-3, VII-4, VII-5 and VII-6), utilizing substituted styrene and a diol or diamine.

Schemes 3A
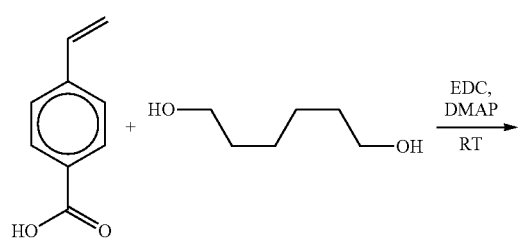
Schemes 3D
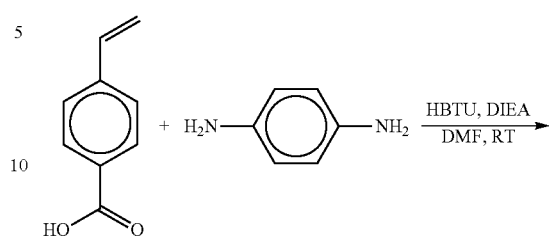
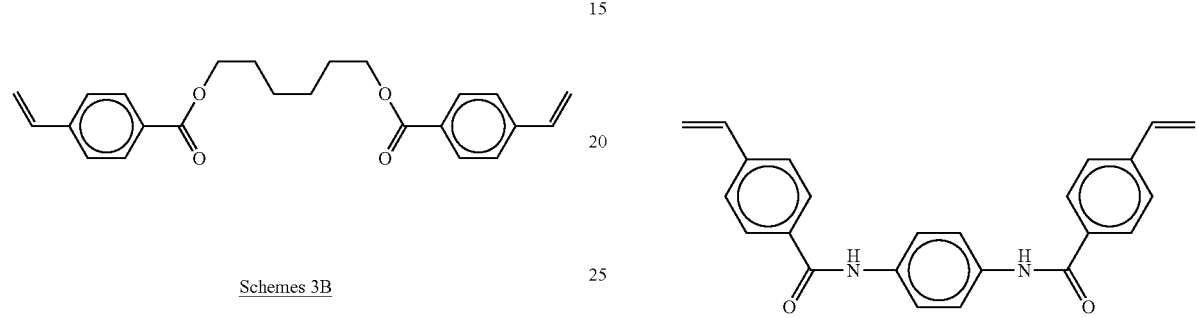
Schemes 3B
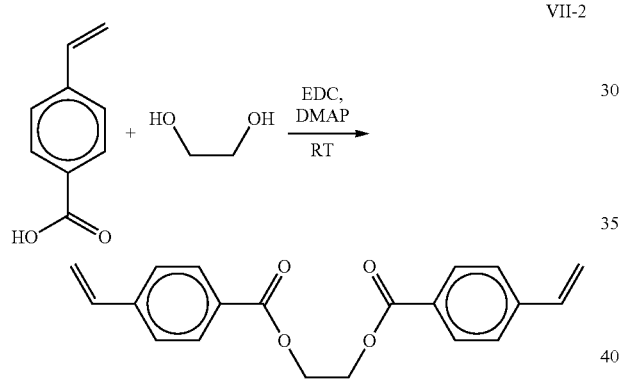
Schemes 3E
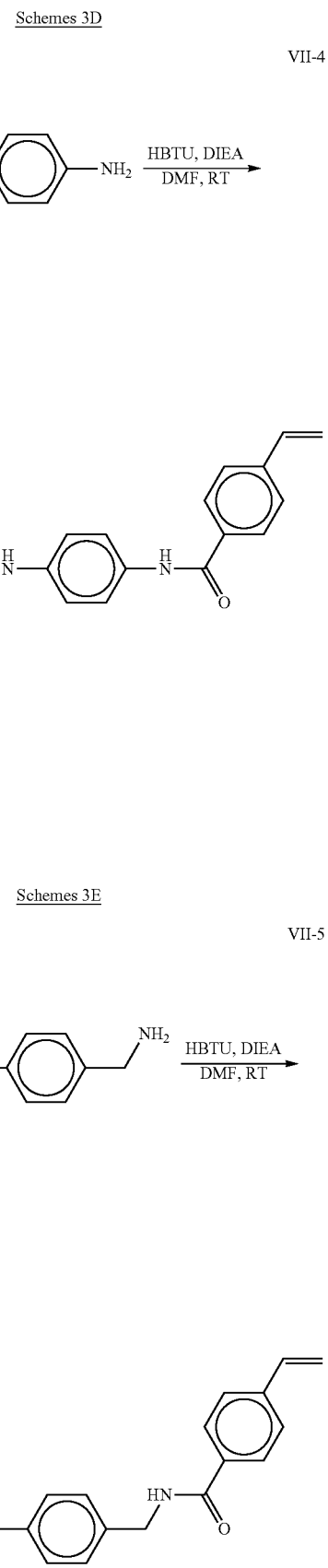
Schemes 3C
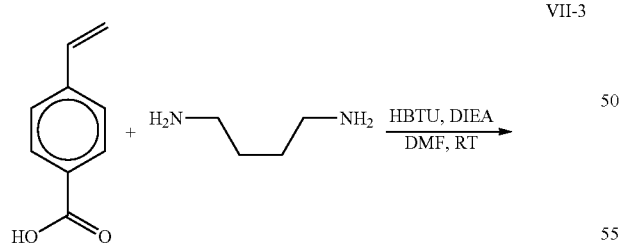
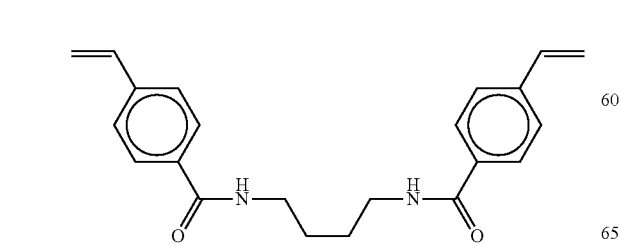

Schemes 3F

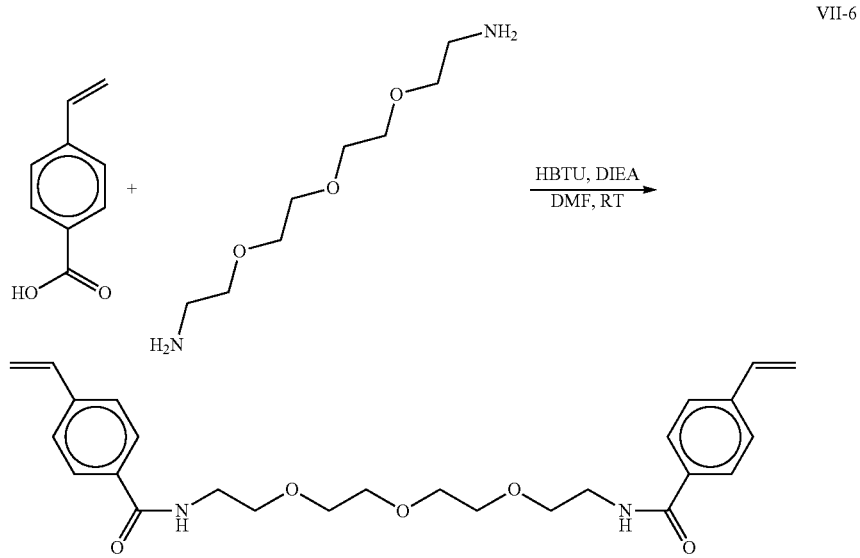

VII-6

Crosslinker VII-1 [hexane-1,6-diyl bis(4-vinylbenzoate)] Preparation Protocol Into a 100-mL round bottom flask, 1.97 g (13.3 mmol) of 4-vinylbenzoic acid, 3.8 g (19.8 mmol) of N-ethyl-N'-(3-dimethylaminopropyl)carbodiimide hydrochloride (EDC·HCl), and 4.8 g (39.3 mmol) of 4-Dimethylaminopyridine (DMAP) dissolved in 50.0 mL of dichloromethane were charged. The mixture was stirred at ambient temperature for 30 minutes. Then, 0.77 g (6.5 mmol) of 1,6-hexanediol was added to the reaction mixture. The reaction mixture was stirred for 24 hours and then poured into 70.0 mL of 2.0 N HCl. The reaction mixture was extracted with ethyl acetate. The organic phase was washed with saturated sodium bicarbonate (3×50.0 mL) and saturated NaCl solution (50.0 mL). The organic phase was dried over anhydrous sodium sulfate and concentrated in a RotaVap under reduced pressure to give 3.8 g (78% yield) of Compound VII-1 as beige powder. $^1$H NMR (CDCl$_3$) (δ, ppm): 1.57 (t, 4H), 1.81 (t, 4H), 4.31 (t, 4H), 5.236 (d, 2H), 5.83 (d, 2H), 6.70 (dd, 2H), 7.43 (d, 4H), 7.97 (d, 4H).

Crosslinker VII-2 [ethane-1,2-diyl bis(4-vinylbenzoate)] Preparation Protocol Into a 100-mL round bottom flask, 1.6 g (10.8 mmol) of 4-vinylbenzoic acid, 2.94 g (15.3 mmol) of N-ethyl-N'-(3-dimethylaminopropyl)carbodiimide hydrochloride (EDC·HCl), and 3.8 g (31.1 mmol) of 4-Dimethylaminopyridine (DMAP) dissolved in 50.0 mL of dichloromethane were charged. The reaction mixture was stirred at room temperature for 30 minutes. Then, 0.32 g (5.1 mmol) of purified ethylene glycol was added to the flask. The reaction was stirred for 24 hours. The solution was poured into 70.0 mL of 2 N HCl. The compound was extracted with ethyl acetate. The organic phase was washed with saturated sodium bicarbonate (3×50.0 mL) and saturated NaCl solution (50.0 mL). The organic phase was dried over anhydrous sodium sulfate and concentrated in a RotaVap under reduced pressure to give 1.5 g (85% yield) of Compound VII-2 as a beige powder. $^1$H NMR (CDCl$_3$) (δ, ppm): 4.67 (s, 4H), 5.37 (d, 2H), 5.83 (d, 2H), 6.70 (dd, 2H), 7.45 (d, 4H), 7.998 (d, 4H).

Crosslinker VII-3 [N,N'-(butane-1,4-diyl)bis(4-vinylbenzamide)] Preparation Protocol Into a 100-mL round bottom flask 4-vinylbenzoic acid (592.7 mg, 4 mmol), dimethylformamide (20.0 mL), N,N,N',N'-Tetramethyl-O-(1H-benzotriazol-1-yl)uronium hexafluorophosphate (HBTU) (2.28 g, 6.0 mmol), and N,N-diisopropylethylamine (3.5 mL, 20 mmol) were charged. The reaction mixture was stirred for 30 minutes. Then, 1,4-diaminobutane (176.3 mg, 2 mmol) was added and the reaction mixture was stirred for 24 hours at ambient temperature. The reaction mixture was poured into 50.0 mL of 2 N HCl and the compound was extracted using dichloromethane. The organic phase was washed with more water to remove DMF. The combined dichloromethane layers were dried over anhydrous sodium sulfate, filtered, and concentrated in a RotaVap. The isolated product gave 0.59 g (84% yield) of Compound VII-3 as a white powder. $^1$H NMR (DMSO) (δ, ppm): 1.56 (s, 4H), 3.27 (d, 4H), 5.34 (d, 2H), 5.91 (d, 2H), 6.77 (dd, 2H), 7.53 (d, 4H), 7.81 (d, 4H), 8.48 (t, 1H).

Crosslinker VII-4 [N,N'-(1,4-phenylene)bis(4-vinylbenzamide)] Preparation Protocol Into a 100-mL round bottom flask, 4-vinylbenzoic acid (626.3 mg, 4 mmol), dimethylformamide (20.0 mL), N,N,N',N'-Tetramethyl-O-(1H-benzotriazol-1-yl)uronium hexafluorophosphate (HBTU) (2.28 g, 6.0 mmol) and N,N-diisopropylethylamine (2.1 mL, 12 mmol) were charged. The mixture was magnetically stirred for 30 minutes at ambient temperature. Then, 1,4-phenylenediamine (216.3 mg, 2 mmol) was added and the reaction was magnetically stirred for 24 hours at ambient temperature. The reaction mixture was poured into 50.0 mL of 2 N HCl, and the compound was extracted using dichloromethane. The organic phase was extracted with water to remove DMF. The extracted organic phase was dried over anhydrous sodium sulfate, filtered, and concentrated in a RotaVap to give 0.68 g (87% yield) of Compound VII-4 as a white powder. $^1$H NMR (DMSO) (δ, ppm): 5.39 (d, 2H), 5.97 (d, 2H), 6.79 (dd, 2H), 7.62 (d, 4H), 7.75 (s, 4H), 7.95 (d, 4H), 10.24 (s, 1H).

Crosslinker VII-5 [N,N'-(1,4-phenylenebis(methylene))bis(4-vinylbenzamide)] Preparation Protocol Into a 100-mL round bottom flask. 4-vinylbenzoic acid (592.7 mg, 4 mmol), dimetylformamide (20.0 mL), N,N,N',N'-Tetramethyl-O-(1H-benzotriazol-1-yl)uronium hexafluorophosphate (HBTU) (2.28 g, 6.0 mmol) and N,N-diisopropylethylamine (3.5 mL, 20 mmol) were charged. The mixture was magnetically stirred for 30 minutes at ambient temperature. Then, 1,4-xylelenediamine (272.4 mg, 2 mmol) was added and the reaction was stirred constantly for 24 hours at ambient temperature. The reaction mixture was poured into xxx mL of 2 N HCl, and the compound was extracted using dichloromethane. The organic phase was washed with more water to remove DMF. The extracted organic phase was dried over anhydrous sodium sulfate, filtered, and concentrated in a RotaVap to give 0.71 g (90% yield) of Compound VII-5 as a white powder. $^1$H NMR (DMSO) (δ, ppm): 4.44 (d, 2H), 5.35 (d, 2H), 5.93 (d, 2H), 6.74 (dd, 2H), 7.28 (s, 4H), 7.55 (d, 4H), 7.85 (d, 4H), 9.03 (t, 1H).

Crosslinker VII-6 [N,N'-(((oxybis(ethane-2,1-diyl))bis(oxy))bis(ethane-2,1-diyl))bis(4-vinylbenzamide)] Preparation Protocol Into a 100-mL round bottom flask. 4-vinylbenzoic acid (0.89 g, 6 mmol), dimethylformamide (20.0 mL), N,N,N',N'-tetramethyl-O-(1H-benzotriazol-1-yl)uronium hexafluorophosphate (HBTU) (3.43 g, 9.0 mmol) and N,N-diisopropylethylamine (5.25 mL, 30 mmol) were charged. The mixture was magnetically stirred for 30 minutes at ambient temperature. Then, 1,11-diamine-3,6,9-trioxaundecane (0.6 g, 3.1 mmol) was added and the reaction mixture was stirred for 24 hours at room temperature. The mixture was poured into 50.0 mL of 2 N HCl, and the compound was extracted using dichloromethane. The organic phase was washed with more water (50.0 mL) to remove DMF. The combined organics were dried over anhydrous sodium sulfate, filtered, and concentrated in a RotaVap to give 0.87 g (64% yield) of Compound VII-6 as a white powder. $^1$H NMR (CDCl$_3$) (δ, ppm): 3.63 (t, 16H), 5.32 (d, 2H), 5.78 (d, 2H), 6.67 (dd, 2H), 7.42 (d, 4H), 7.73 (d, 4H).

Scheme 4 illustrates the use of a crosslinker of Formula (VI) for the preparation of porous, crosslinked polystyrene beads.

Scheme 4

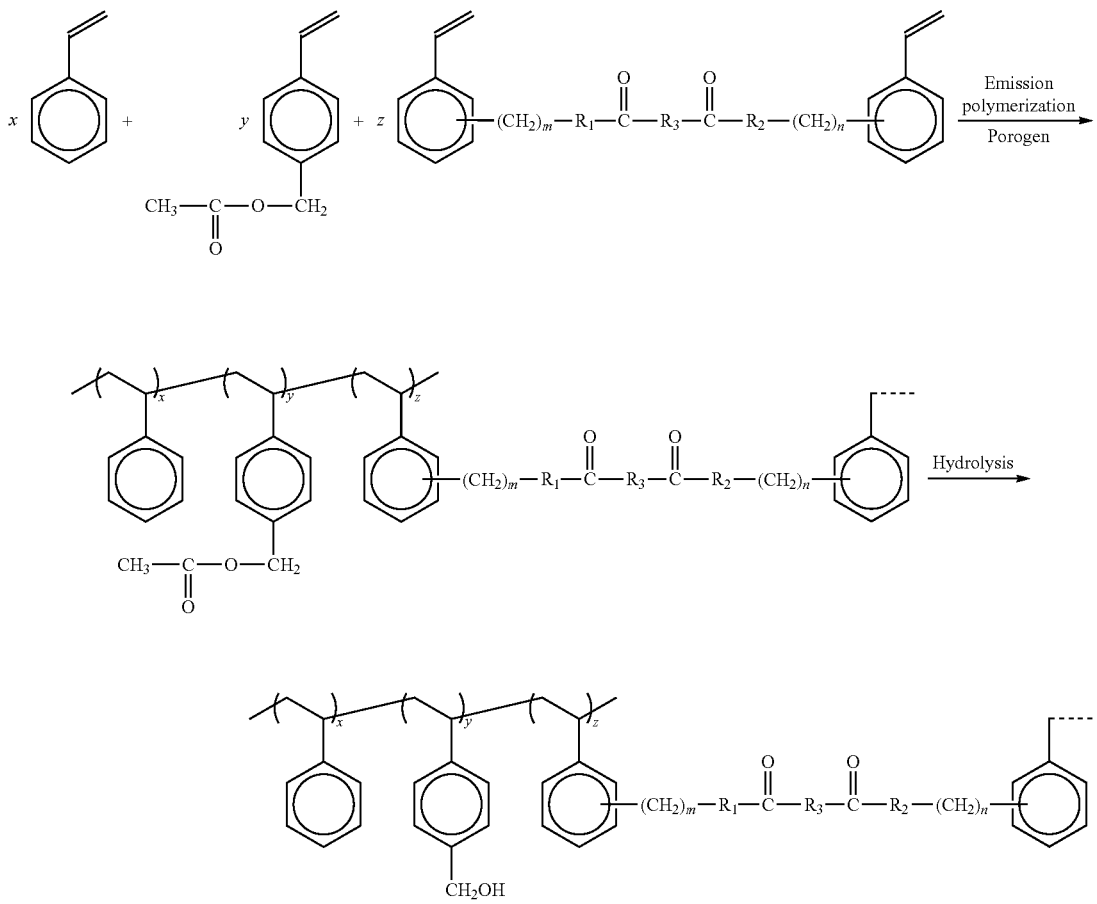

Example 3. Crosslinker of Formula (VIII) Preparation and Use

Scheme 5 illustrates the preparation protocol of a crosslinker of Formula VIII-a, starting with styrene and 1,4-bis(chloromethyl)benzene.

Scheme 5

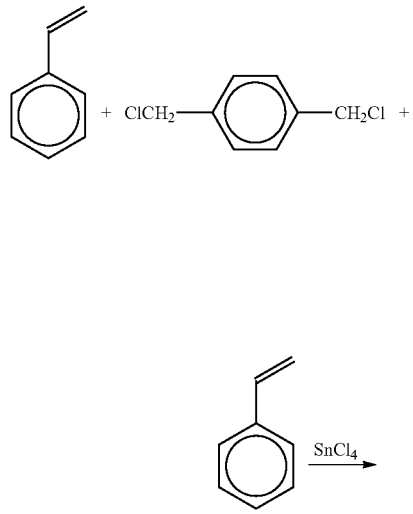

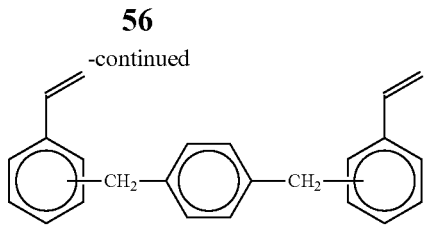

VIII-a

Porous, Crosslinked Polystyrene Beads Preparation Protocol with Crosslinker of Formula (VIII)

A 500 mL three-neck round-bottom flask equipped with a heater/cooler, a stirrer and an argon introducing needle is set in a thermostat oil bath. Polyvinyl alcohol (7.1 g) is dissolved in water (373.3 g), and the obtained aqueous solution is placed in the 500 mL three-neck round-bottom flask. A mixed solution of a monomer, porogen and a polymerization initiator is prepared by mixing styrene (16 g), Crosslinker of Formula VIII-1 (4 g), 2-ethylhexanol (14 g), isooctane (6 g) and benzoyl peroxide (containing 25% of water, 0.4 g). The mixed solution is placed in the 500 mL three-neck round-bottom flask. The mixture is stirred under a room temperature argon stream and heated to 80° C. Suspension polymerization is conducted for 15 hr. The reaction product is cooled, filtered, and the residue is washed and dried to give porous microparticles. The obtained particles have a particle size from about 20 μm to about 100 μm. Agglomerate particles are not found.

Scheme 6 illustrates the use of a crosslinker belonging to Crosslinker of Formula (VIII) in the preparation of porous, crosslinked polystyrene beads.

Scheme 6

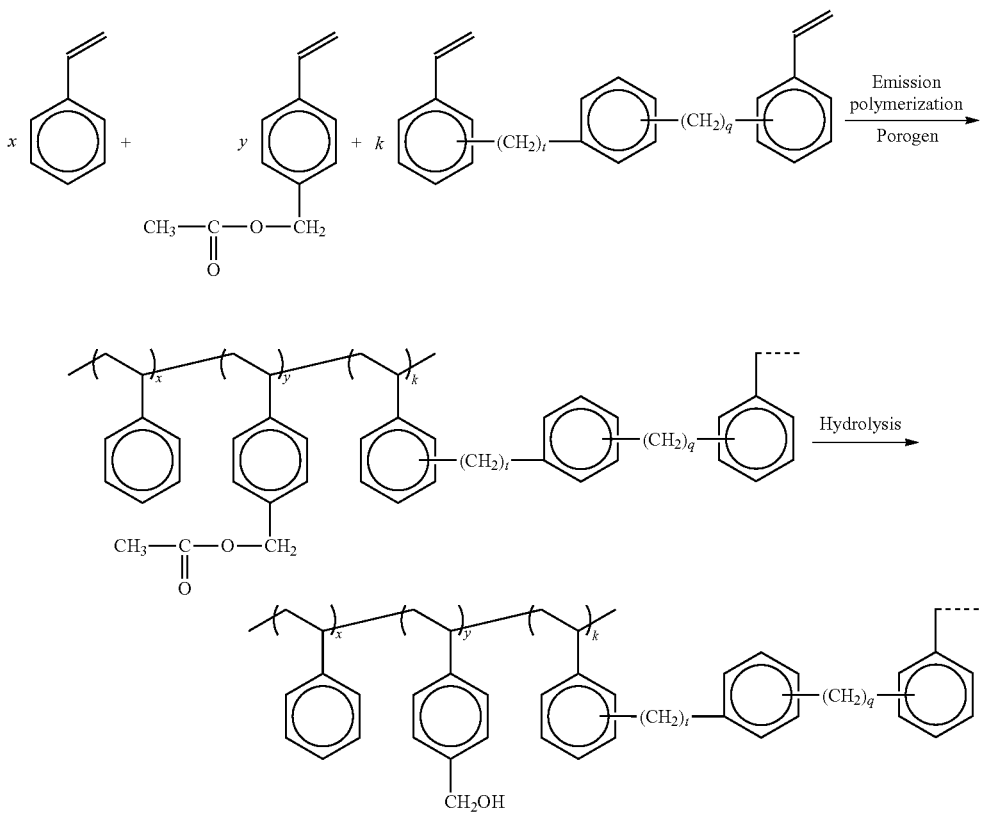

Schemes 7A-7C illustrates the preparation protocol of three various crosslinkers of Formula (VIII) (crosslinker of Formulas VIII-1, VIII-2 and VIII-3), starting with a halogenated styrene and utilizing burnished magnesium. Schemes 7D-7F illustrate the preparation protocol of three additional crosslinkers of Formula (VIII) (crosslinker of Formulas VIII-4, VIII-5 and VIII-6).

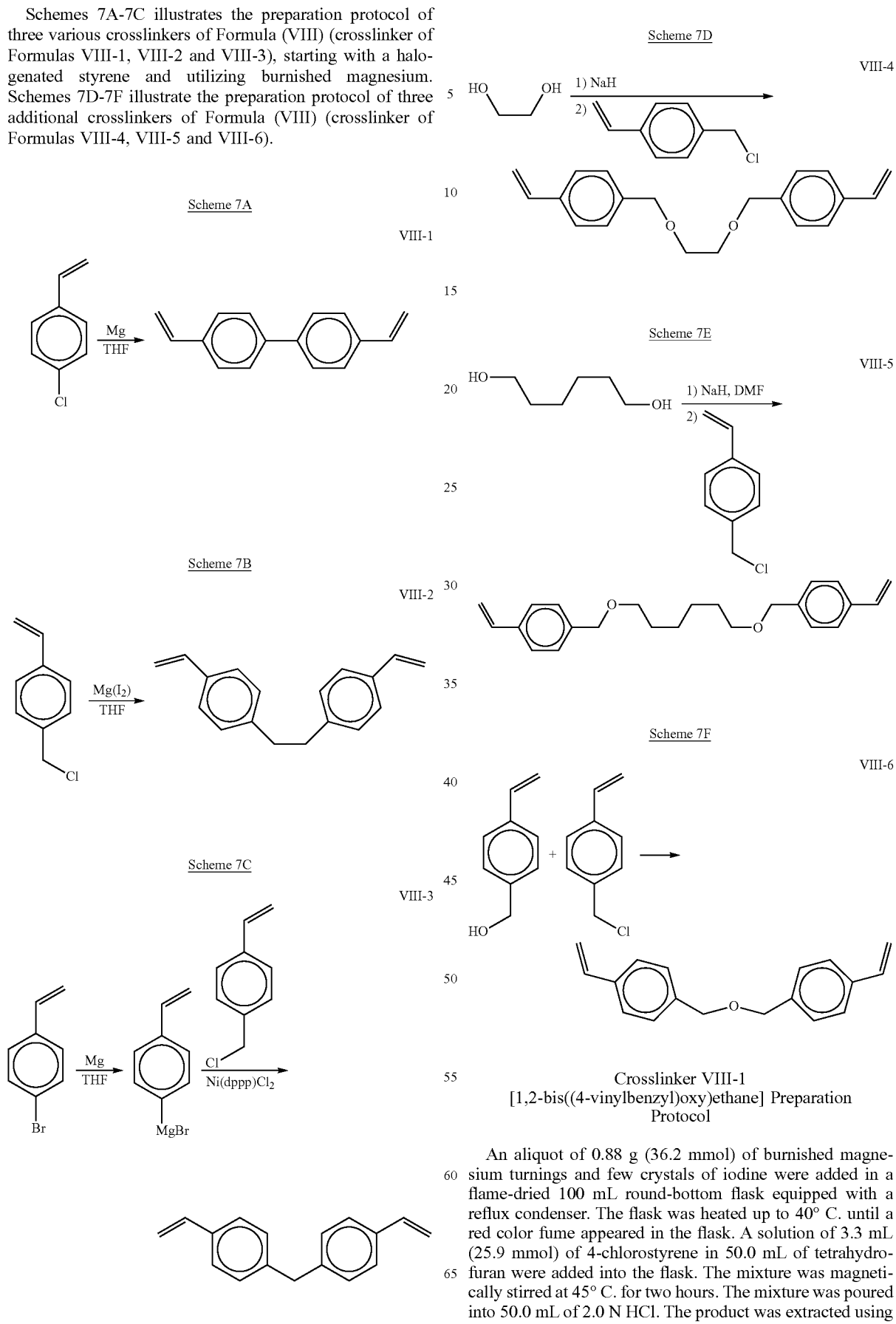

Crosslinker VIII-1
[1,2-bis((4-vinylbenzyl)oxy)ethane] Preparation Protocol

An aliquot of 0.88 g (36.2 mmol) of burnished magnesium turnings and few crystals of iodine were added in a flame-dried 100 mL round-bottom flask equipped with a reflux condenser. The flask was heated up to 40° C. until a red color fume appeared in the flask. A solution of 3.3 mL (25.9 mmol) of 4-chlorostyrene in 50.0 mL of tetrahydrofuran were added into the flask. The mixture was magnetically stirred at 45° C. for two hours. The mixture was poured into 50.0 mL of 2.0 N HCl. The product was extracted using dichloromethane. The organic phase was dried using anhydrous sodium sulfate and concentrated in a RotaVap to give 3.0 g (57% yield) of Compound VIII-1 as a beige powder. $^1$H NMR (CDCl$_3$) (δ, ppm): 5.26 (d, 2H), 5.76 (d, 2H), 6.71 (dd, 2H), 7.47 (d, 4H), 7.56 (d, 4H).

Crosslinker VIII-2 [1,2-bis(4-vinylphenyl)ethane] Preparation Protocol

An aliquot of 1.99 g (81.9 mmol) of burnished magnesium turnings and few crystals of iodine were added in a flame-dried 250 mL round-bottom flask with reflux condenser. The flask was heated up to 40° C. until a red color fume appeared in the flask. A solution of 8.90 mL (63.2 mmol) of 4-vinylbenzyl chloride in 100.0 mL of tetrahydrofuran were added into the flask. The mixture was magnetically stirred at 45° C. for two hours. The reaction mixture was poured into 70.0 mL of cold 2.0 N HCl. The product was extracted using dichloromethane. The organic phase was dried using anhydrous sodium sulfate and concentrated in a RotaVap to give 6.0 g (82% yield) of Compound VIII-2 as a beige powder. $^1$H NMR (CDCl$_3$) (δ, ppm): 2.90 (s, 4H), 5.18 (d, 2H), 5.68 (d, 2H), 6.65 (dd, 2H), 7.12 (d, 4H), 7.31 (d, 4H).

Crosslinker VIII-3 [bis(4-vinylphenyl)methane] Preparation Protocol

An aliquot of 1.04 g (42.8 mmol) of burnished magnesium turnings were added in a flame-dried 250 mL round-bottom flask equipped with a reflux condenser. A solution of 4.3 mL (32.9 mmol) of 4-bromostyrene in 70.0 mL of anhydrous tetrahydrofuran were added into the flask. The mixture was magnetically stirred at 45° C. for two hours. Then, 1.07 g (2.0 mmol) of 1,3-bis(diphenylphosphino)propane dichloronickel [Ni(dppp) Cl$_2$] and 4.7 mL (33.4 mmol) of 4-vinylbenzylchloride was added. The mixture was stirred for 48 hours at 45° C. The mixture was poured into 50.0 mL of 2.0 N HCl. The product was extracted using dichloromethane. The organic phase was dried using anhydrous sodium sulfate and concentrated in a RotaVap to give 5.2 g (72% yield) of Compound VIII-3 in a powder form. $^1$H NMR (CDCl$_3$) (δ, ppm): 3.94 (s, 2H), 5.17 (d, 2H), 5.67 (d, 2H), 6.63 (dd, 2H), 7.11 (d, 4H), 7.31 (d, 4H).

Crosslinker VIII-4 [1,2-bis((4-vinylbenzyl)oxy)ethane] Preparation Protocol

In a 100-mL round bottom flask equipped with a reflux condenser, an aliquot of 1.80 g (28.7 mmol) of ethylene glycol dissolved in 35.0 mL of anhydrous dimethylformamide (DMF) was added. A solution of 1.59 g (66.3 mmol) of dry sodium hydride in 20.0 mL of anhydrous DMF was added dropwise over a period of 30 minutes. The reaction mixture was magnetically stirred at room temperature for two hours. An aliquot of 8.50 mL (60.3 mmol) of 4-vinylbenzyl chloride was added to the flask. The mixture was constantly stirred at 45° C. for 24 hours. The reaction mixture was poured into 70.0 mL of water and the product was extracted with ethyl acetate. The organic extract was dried over anhydrous sodium sulfate and concentrated in a RotaVap under reduced pressure to give 6.0 g (71% yield) of Compound VIII-4 as a yellowish oil. $^1$H NMR (CDCl$_3$) (δ, ppm): 3.65 (s, 4H), 4.57 (s, 4H), 5.21 (d, 2H), 5.71 (d, 2H), 6.71 (dd, 2H), 7.29 (d, 4H), 7.38 (d, 4H).

Crosslinker VIII-5 [1,6-bis((4-vinylbenzyl)oxy)hexane] Preparation Protocol

In a 100-mL round bottom flask equipped with a reflux condenser, an aliquot of 1.20 g (10.2 mmol) of 1,6-hexanediol and 35.0 mL of anhydrous dimethylformamide (DMF) was charged. A solution of 0.55 g (22.9 mmol) dry sodium hydride in 20.0 mL of anhydrous DMF was added dropwise over a period of 30 minutes. The mixture was stirred constantly at ambient temperature for two hours. An aliquot of 3.0 mL (21.3 mmol) 4-vinylbenzyl chloride was added into the reaction mixture. The mixture was stirred constantly at 45° C. for 24 hours. The reaction mixture was poured into 70.0 mL of water and the product was extracted with ethyl acetate. The organic extract was dried over anhydrous sodium sulfate and concentrated in a RotaVap to give 2.2 g (63% yield) of Compound VIII-5 as a yellowish oil. $^1$H NMR (DMSO) (δ, ppm): 1.28 (s, 4H), 1.48 (s, 4H), 3.35 (t, 4H), 4.39 (s, 4H), 5.18 (d, 2H), 5.73 (d, 2H), 6.64 (dd, 2H), 7.24 (d, 4H), 7.38 (d, 4H).

Crosslinker VIII-6 [4,4'(oxybis(methylene))bis(vinylbenzene)] Preparation Protocol Into a 100-mL round bottom flask equipped with a reflux condenser, an aliquot of 10.3 g (76.8 mmol) of hydroxymethylstyrene and 20.0 mL of anhydrous dimethylformamide (DMF) were charged and dissolved. A solution of 2.21 g (92.1 mmol) of dry sodium hydride in 30.0 mL of anhydrous DMF was added dropwise over a period of 45 minutes. The mixture was magnetically stirred at room temperature for additional two hours. An aliquot of 11.9 mL (84.4 mmol) of 4-vinylbenzyl chloride was added to the flask. The mixture was constantly stirred at 45° C. for 48 hours. The reaction mixture was poured into 100.0 mL of water and the product was extracted with ethyl acetate. The organic phase was dried over anhydrous sodium sulfate and concentrated in a RotaVap under reduced pressure to give 8.4 g (44% yield) of Compound VIII-6 as white crystals. $^1$H NMR (CDCl$_3$) (δ, ppm): 4.54 (s, 4H), 5.22 (d, 2H), 5.71 (d, 2H), 6.71 (dd, 2H), 7.30 (d, 4H), 7.39 (d, 4H).

Example 4. Porous, Crosslinked Polystyrene Hydroxylated Polystyrene (PCHP) Beads Preparation Protocol and Oligo Synthesis Porous, crosslinked polystyrene hydroxylated polystyrene (PCHP) beads utilizing various crosslinkers were prepared and the particle size and size distribution of the resin beads were analyzed. The general procedures of the preparation of crosslinked acetoxymethylated polystyrene beads, the hydrolysis of the polystyrene beads, and loading of DMT-dT-3'-succinate on the PCHP resin beads are set forth below. The procedures and analysis of the efficiency of oligo synthesis of 20-mer DNA oligonucleotides are further provided.

Porous, Crosslinked Polystyrene Beads Preparation Protocol with Crosslinker of Formula (VIII-4)

Into a 1000-mL reactor flask, equipped with a condenser, an agitator and a nitrogen bleeding tube and setting on a constant temperature water bath, polyvinyl alcohol (7.1 g, supplied by KURARAY) and distilled water (340 g) were charged. The mixture was stirred at 300 rpm to dissolve the polyvinyl alcohol. A solution of styrene (16.0 g), p-acetoxymethylstyrene (2.0 g), crosslinker of Formula VIII-4 (2.0 g), 2-ethylhexanol (14.0 g), isooctane (6.0 g) and benzoyl peroxide (0.45 g) were added thereto. The reaction mixture was stirred constantly under a nitrogen stream at 80° C. to perform suspension copolymerization overnight. The polymerization product was washed by filtration using distilled water and acetone, and subsequently dispersed in 1 L of acetone. The dispersion was allowed to stand and settle. The supernatant was discarded. About 1 L of fresh acetone was added. The process of washing with 1 L of fresh acetone, sedimentation/precipitation, and discarding supernatant was repeated two more times. Filtration of the suspension and drying under reduced pressure gave 9.1 g of porous resin beads.

Hydrolysis of Porous, Crosslinked Polystyrene Beads Prepared with Crosslinker of Formula (VIII-4) to Give Hydroxylated Polystyrene Beads (Sample 1)

Into a 500-mL reaction flask, equipped with a condenser, an agitator and a nitrogen bleeding tube, the porous, crosslinked polystyrene beads prepared with crosslinker of Formula VIII-4 (2 g), ethanol (40 g), 10% sodium hydroxide solution (20 g), were charged. The reaction mixture was stirred constantly at 75° C. for 8 hr. The reaction mixture was neutralized with 2.0 N hydrochloric acid, washed with distilled water and acetone, and dried under reduced pressure to give 1.95 g of hydroxylated polystyrene (PCHP) resin beads.

Loading of DMT-dT-3'-Succinate on PCHP Resin Beads

Porous resin beads PCHP (Sample 1), DMT-dT-3'-succinate, O-(benzotriazole-1-yl)-N,N,N',N'-tetramethyluronium hexafluorophosphate (HBTU), N,N-diisopropylethylamine (DIEA) and acetonitrile were mixed, and the mixture was stirred at ambient temperature for 12 hr. The resins were filtered, washed with acetonitrile, and dried under reduced pressure. The dry resin beads were mixed with Cap A (15 mL, 10% acetic anhydride/80% THF/10% 2,6-lutidine), Cap B (15 ml, 16% 1-methylimidazole/84% THF), and the mixture was stirred at ambient temperature for 2 hr. The resin beads were filtered, washed with acetonitrile, and dried under reduced pressure to give 2.0 g porous resin beads loaded with DMT-dT-3'-succinate.

Functional group loading of resin beads was determined by the dimethoxytrityl (DMT) loading assay after coupling the first dT. To conduct the DMT assay, about 3 mg of the dT-conjugated polystyrene solid support was weighted and added into 100 mL of agitate 0.1 M toluene sulfonic acid in acetonitrile. The mixture was mixed well and let settle for 10 min. The supernatant was measured by UV-visible spectrophotometer to get the absorbance at 498 nm to determine the loading number. The amount of DMT-dT-3'-succinate loaded was 228 µmol/g.

Hydroxylated Polystyrene Beads with Crosslinker of Formula (VIII-6) (Sample 2)

Hydroxylated polystyrene beads with crosslinker of Formula VIII-6 were prepared in the same manner as described herein in the preparation of the hydroxylated polystyrene beads of Sample 1, by replacing crosslinker of Formula VIII-4 with crosslinker of Formula VIII-6. DMT-dT-3'-succinate was loaded on the porous resin beads. The amount of DMT-dT-3'-succinate loaded on the obtained porous resin beads was 263 µmol/g.

Hydroxylated Polystyrene Beads with Crosslinker of Formula VIII-3 (Sample 3)

Hydroxylated polystyrene beads with Crosslinker of Formula VIII-3 were prepared in the same manner as described herein in the preparation of the hydroxylated polystyrene beads of Sample 1, by replacing crosslinker of Formula VIII-4 with crosslinker of Formula VIII-3. DMT-dT-3'-succinate was loaded on the porous resin beads. The amount of DMT-dT-3'-succinate loaded on the obtained porous resin beads was 199 µmol/g.

Hydroxylated Polystyrene Beads with Divinylbenzene Crosslinker (Sample 4)

Hydroxylated polystyrene beads with divinylbenzene (DVB) crosslinker were prepared in the same manner as described herein in the preparation of the hydroxylated polystyrene beads of Sample 1, by replacing crosslinker of Formula VIII-4 with divinylbenzene. The amount of DMT-dT-3'-succinate loaded on the obtained porous resin beads was 179 µmol/g.

Hydroxylated Polystyrene Beads with Crosslinker of Formula VIII-4 and Acetoxystyrene (Comparative Sample 1)

Hydroxylated polystyrene beads obtained from crosslinker of Formula VIII-4 and acetoxy styrene were prepared in the same manner as described herein in the preparation of the hydroxylated polystyrene beads of Sample 1, by replacing acetoxymethyl styrene with acetoxystyrene. Styrene (16.0 g), p-acetoxystyrene (2.0 g), Crosslinker of Formula VIII-4 (2.0 g), 2-ethylhexanol (14.0 g) and isooctane (6.0 g) were used as co-monomers for copolymerization to prepare porous resin beads comprising hydroxy styrene repeat units after hydrolysis. DMT-dT-3'-succinate was loaded on the porous resin beads to give a loading of 231 µmol/g.

Hydroxylated Polystyrene Beads with Crosslinker of Formula VIII-5 and Acetoxystyrene (Comparative Sample 2)

Hydroxylated polystyrene beads obtained from crosslinker of Formula VIII-5 and acetoxystyrene were prepared in the same manner as described herein in the preparation of the hydroxylated polystyrene beads of Sample 1, by replacing acetoxymethyl styrene with acetoxystyrene. Styrene (16.0 g), p-acetoxystyrene (2.0 g), Crosslinker of Formula VIII-5 (2.0 g), 2-ethylhexanol (14.0 g) and isooctane (6.0 g) were used as the composition for co-polymerization to prepare porous resin beads comprising styrene and p-hydroxystyrene after hydrolysis. DMT-dT-3'-succinate was loaded on the obtained porous resin beads. The amount of DMT-dT-3'-succinate loaded on the porous resin beads was 258 µmol/g.

Hydroxylated Polystyrene Beads with Crosslinker of Formula VIII-2 and Acetoxystyrene (Comparative Sample 3)

Hydroxylated polystyrene beads with crosslinker of Formula VIII-2 and acetoxystyrene were prepared in the same manner as described herein in the preparation of the hydroxylated polystyrene beads of Sample 1, by replacing acetoxymethyl styrene with acetoxystyrene. Styrene (16.0 g), p-acetoxystyrene (2.0 g), crosslinker of Formula VIII-2 (2.0 g), 2-ethylhexanol (14.0 g) and isooctane (6.0 g) were used as the composition for co-polymerization to prepare porous resin beads comprising styrene and p-hydroxystyrene after hydrolysis. DMT-dT-3'-succinate was loaded on the obtained porous resin beads. The amount of DMT-dT-3'-succinate loaded on the obtained porous resin beads was 248 μmol/g.

Example 5. Solid Phase Oligo Synthesis

To determine the performance of our novel polystyrene solid supports, the first dT was conjugated to the solid support by succinate reaction through its 3' position. Oligonucleotide syntheses were subsequently performed. Oligonucleotides were synthesized by solid phase phosphoramidite method with MerMade 6 synthesizer (LGC, Biosearch Technologies). The novel PCHP solid supports with DMT-dT loading of about 150-300 μmol/g were first suspended in acetonitrile and then wet packed into empty MerMade columns. The amount of the solid support was 4-8 mg for each column to generate ~1 μmol synthesis scale. The oligonucleotide synthesis cycle included the following steps:
  (1) Detrylation with 3% dichloroacetic acid in toluene for 45 second two times to deprotect the 5'-DMT. It was followed by acetonitrile washing, and then detrylation for two more times; followed by acetonitrile washing again.
  (2) Coupling with 0.1 M DMT-dT-CE-Phosphoramidite (5'-O-(4,4'-Dimethoxytrityl)-thymidine-3'-cyanoethyl Phosphoramidite) in acetonitrile and 0.5 M activator (tetrazole in acetonitrile) for 1 minute. The coupling step was repeated three more times, followed by acetonitrile washing.
  (3) Oxidation with iodine (0.015 M iodine in water/pyridine/THF 2/20/78, v/v/v) for 45 second, followed by acetonitrile washing.
  (4) Capping with a mixture of acetic anhydride, pyridine, methylimidazole, and THF for 45 second, followed by acetonitrile washing.
  Repeated steps (1)-(4) 4 times for synthesizing a T5, or 19 times for a T20 elongated from the dT-PCHP solid support and finished by the final detrylation with acetonitrile washing.

After synthesis, the oligonucleotide-conjugated PCHP solid supports were treated with a 1:1 mixture of aqueous ammonia hydroxide and methylamine for 15 min to cleave the oligos off the solid supports and to de-protect phosphates. Upon completion, the liquid phase was collected and heat dried at 55° C. in reduced pressure. The dried residue was dissolved in water and analyzed by reverse-phase HPLC (Agilent 1260) and LC-MS (Applied Biosystems 4000 Q-Trap). The HPLC column was Waters XBridge Oligonucleotide BEH C18 column, 4.6 mm×50 mm. The A and B buffer used are A: 50 mM triethylammonium acetate in water and B: 20% acetonitrile and 80% 50 mM triethylammonium acetate in water. The gradient was 20-60% B in 20 min.

HPLC measurement to determine the percentages of Full-length product purity (FLP) for T5 and T20 to be 99.7% and of 90%, respectively as shown in Table 1. FIG. 1 is the HPLC chromatogram of a T20 DNA oligonucleotide synthesized from the PCHP resin beads prepared from Sample 1. The FLP for T20 DNA oligonucleotide synthesized from succinated PCHP resin beads prepared from Sample 1 was about 90%, a substantial improvement from the T20 FLP obtained using commercially available polystyrene solid supports of about 80% (see Table 1).

Figure 2A:
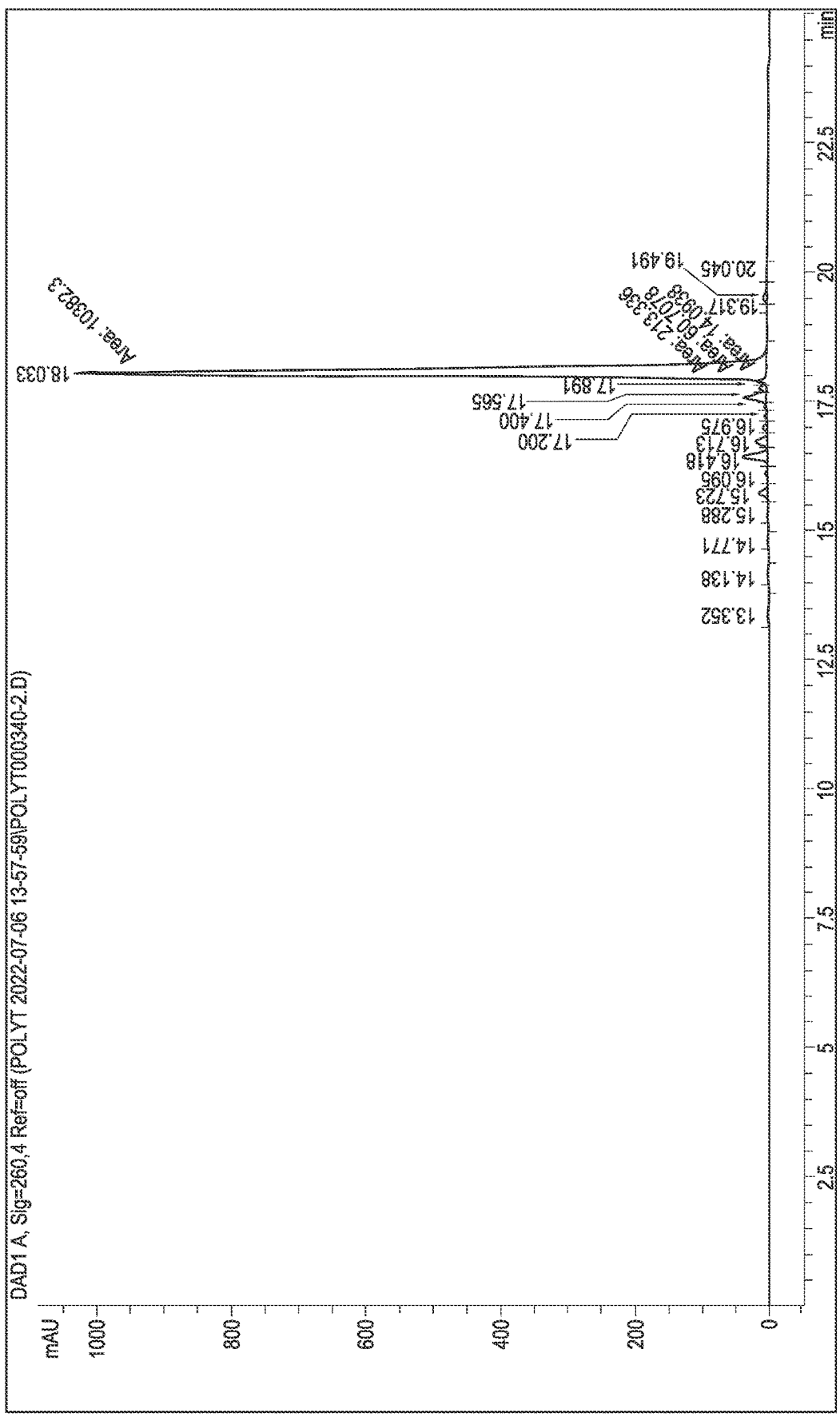
FIG. 2A is a HPLC chromatogram of a T20 DNA oligonucleotide synthesized utilizing crosslinker of Formula VIII-6 according one embodiment of the present disclosure.
Figure 2B:
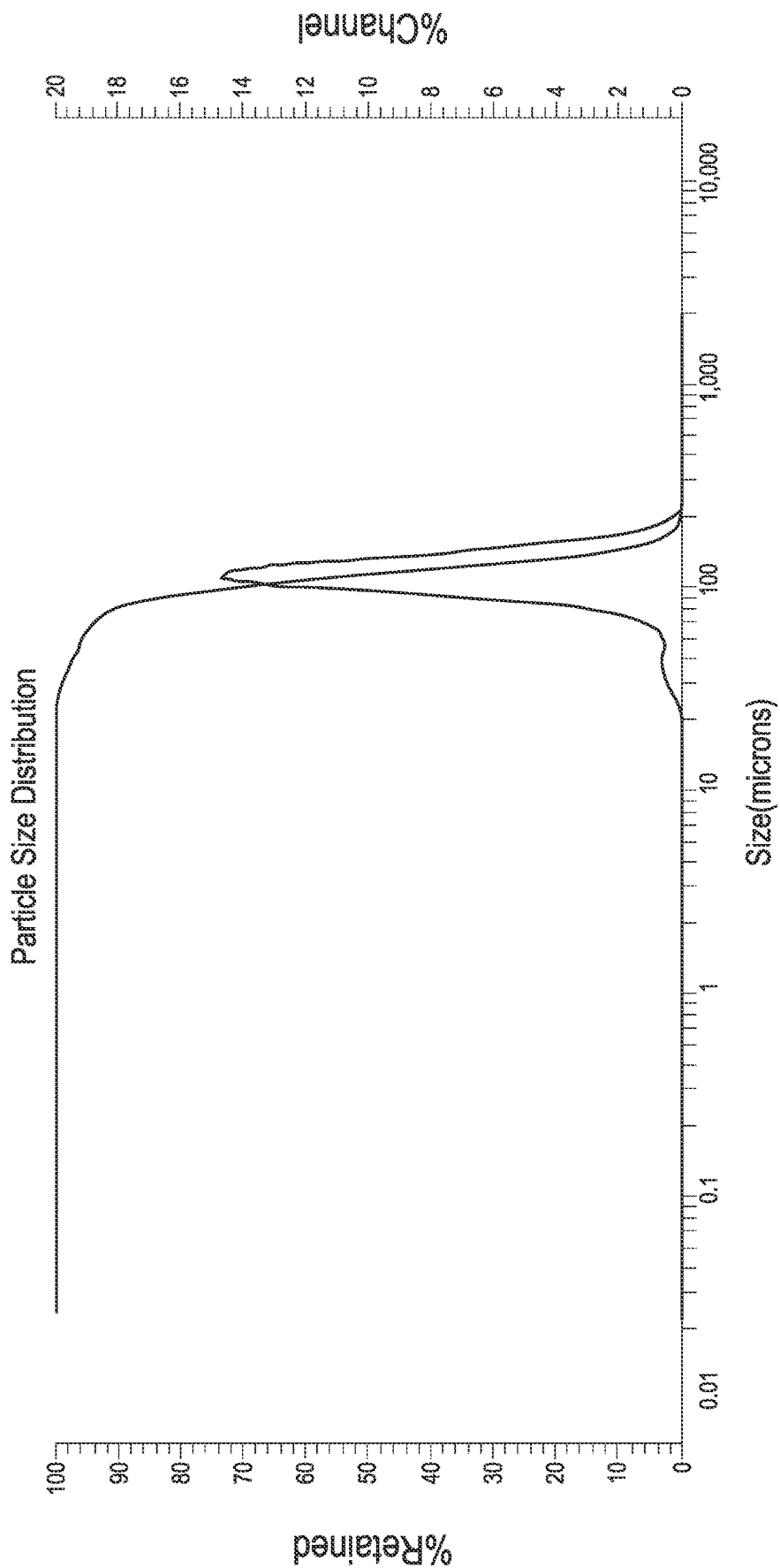
FIG. 2B is a particle size distribution of hydroxylated polystyrene beads with crosslinker of Formula VIII-6 according one embodiment of the present disclosure.

Following the same manner as described above in connection with Sample 1, DNA oligonucleotides with 5 mer and 20 mer were synthesized from succinated PCHP resin beads prepared from Sample 2, and the FLP's of the T5 and T20 oligonucleotides were determined as of 97% and 90%, respectively (see Table 1). FIG. 2A is the HPLC chromatogram of a T20 DNA oligonucleotide synthesized from the PCHP resin beads prepared from Sample 2. FIG. 2B is the particle size distribution of hydroxylated polystyrene beads with crosslinker of Formula VIII-6 (Sample 2) analyzed by MicroTrac before sieving. The viscosity average particle diameter (Dv) was determined to be 103 μm and the number average particle diameter (Dn) was determined to be 61 μm. The average particle size of the beads is about 78 μm after sieving.

Figure 3:
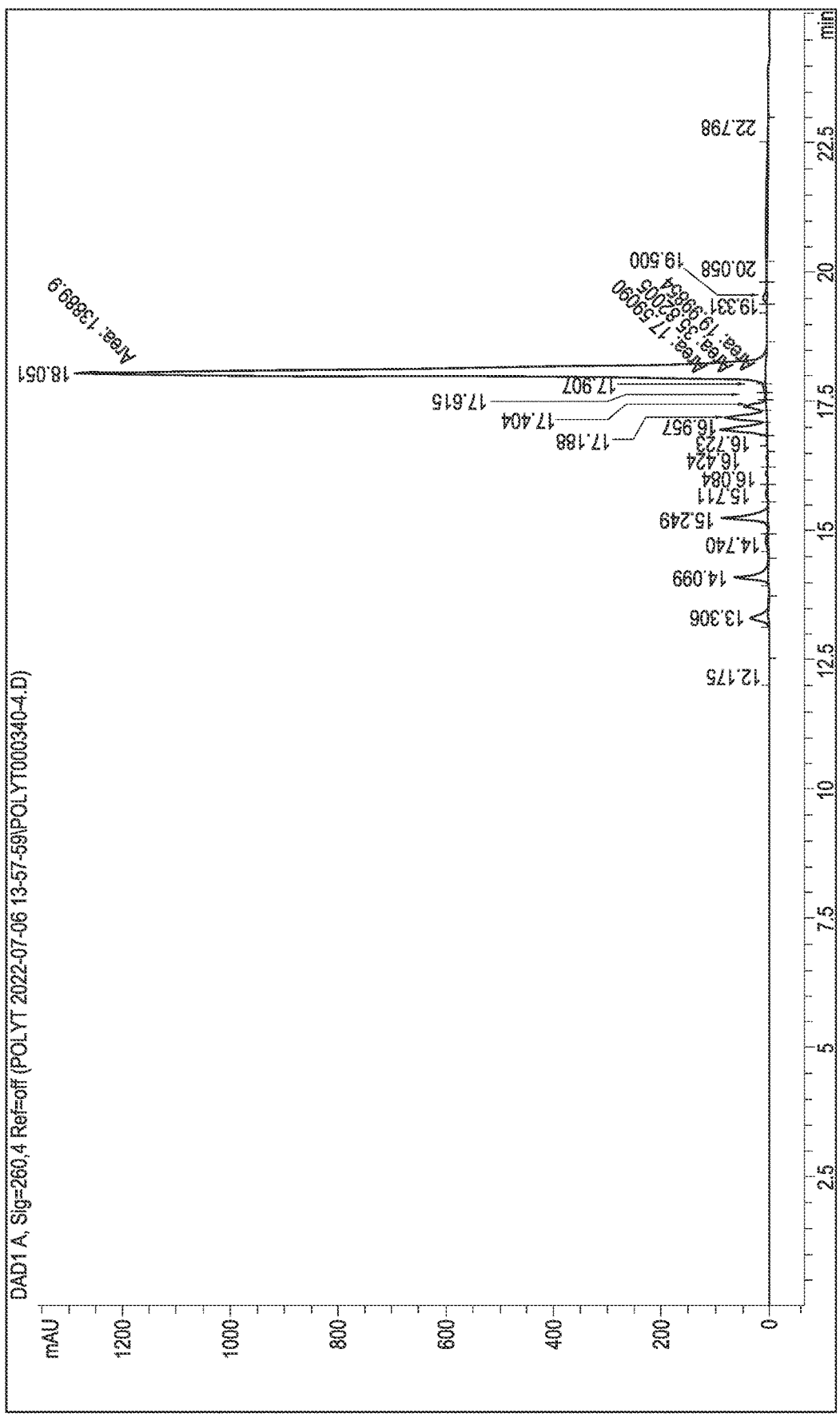
FIG. 3 is a HPLC chromatogram of a T20 DNA oligonucleotide synthesized utilizing crosslinker of Formula VIII-3 according one embodiment of the present disclosure.

Following the same manner as described above in connection with Sample 1, DNA oligonucleotides with 5 mer and 20 mer were synthesized from succinated PCHP resin beads prepared from Sample 3, and the FLP's of the T5 and T20 oligonucleotides were determined as of 98% and 82%, respectively (see Table 1). FIG. 3 is the HPLC chromatogram of a T20 DNA oligonucleotide synthesized from succinated PCHP resin beads prepared from Sample 3.

Figure 4:
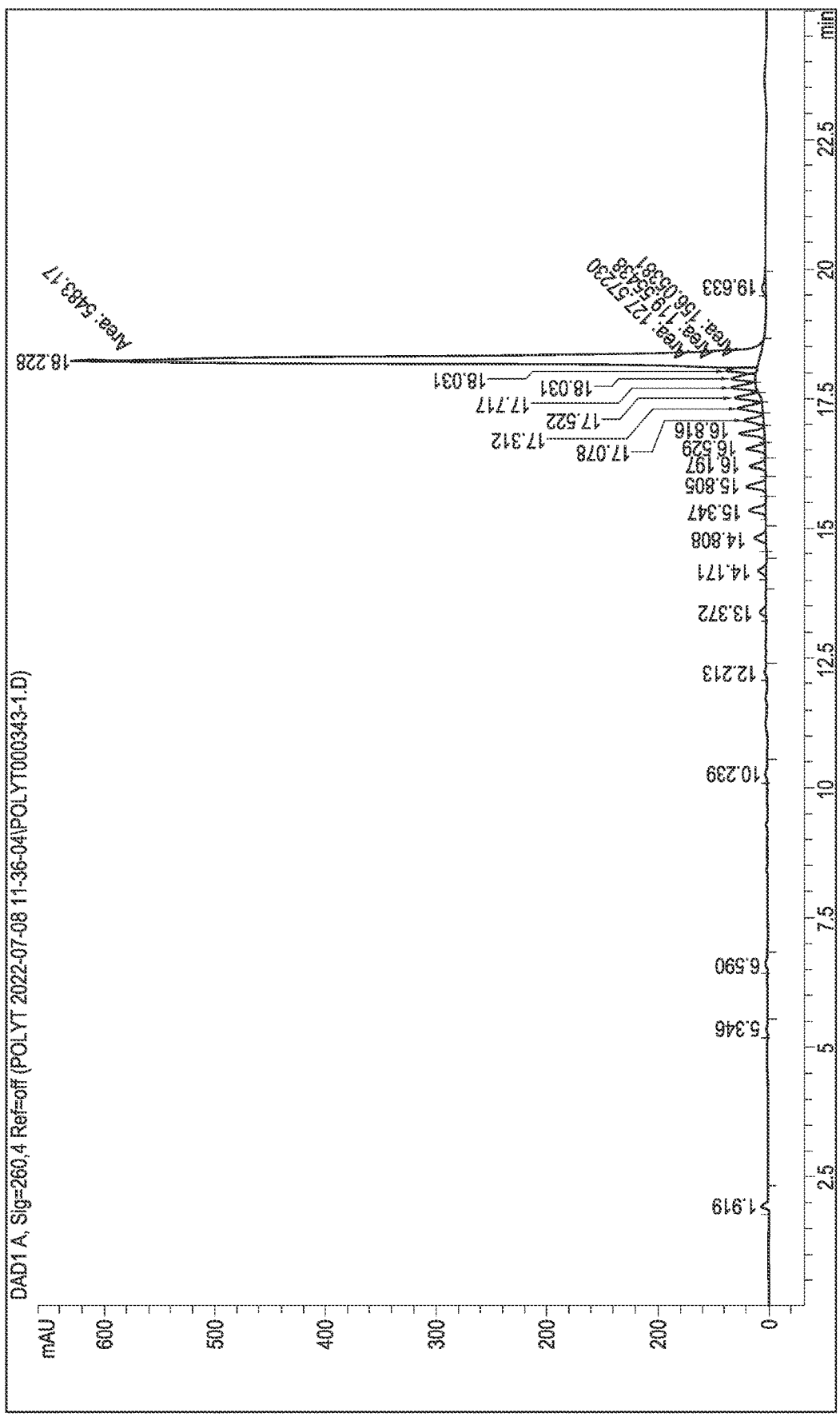
FIG. 4 is a HPLC chromatogram of a T20 DNA oligonucleotide synthesized utilizing divinylbenzene (DVB) as a crosslinker.

Following the same manner as described above in connection with Sample 1, DNA oligonucleotides with 5 mer and 20 mer were synthesized from succinated PCHP resin beads prepared from Sample 4, and the FLP's of the T5 and T20 oligonucleotides were determined 94% and 74%, respectively (see Table 1). FIG. 4 is the HPLC chromatogram of a T20 DNA oligonucleotide synthesized utilizing divinylbenzene (DVB) as a crosslinker.

Figure 5:
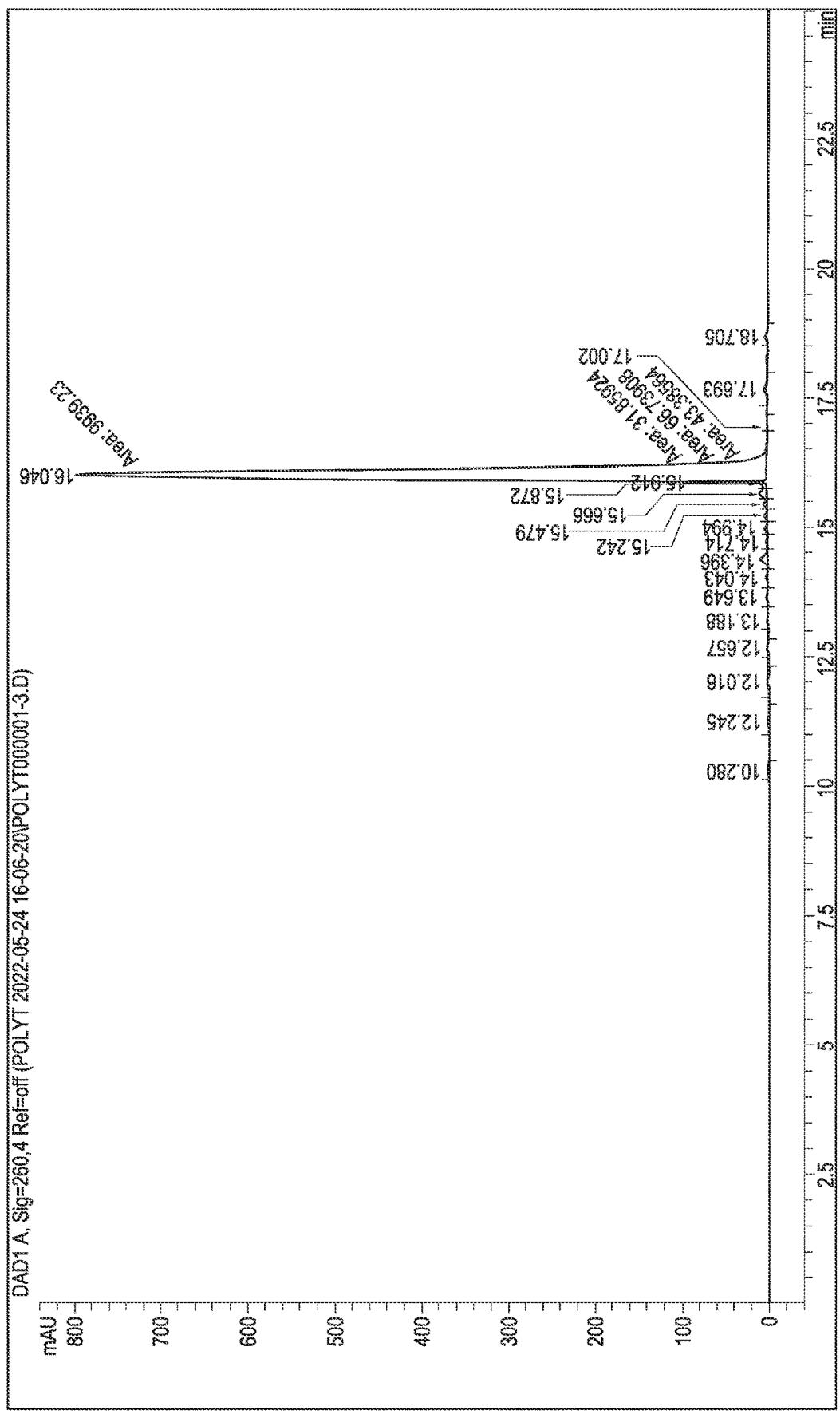
FIG. 5 is a HPLC chromatogram of a T20 DNA oligonucleotide synthesized utilizing crosslinker of Formula VIII-4 with acetoxystyrene according one embodiment of the present disclosure.

Following the same manner as described above in connection with Sample 1, DNA oligonucleotides with 5 mer and 20 mer were synthesized from succinated PCHP resin beads prepared from Comparative Sample 1. The FLP's of the T5 and T20 oligonucleotides were determined 99% and 94%, respectively (see Table 1). FIG. 5 is a HPLC chromatogram of a T20 DNA oligonucleotide synthesized in Comparative Sample 1.

Figure 6:
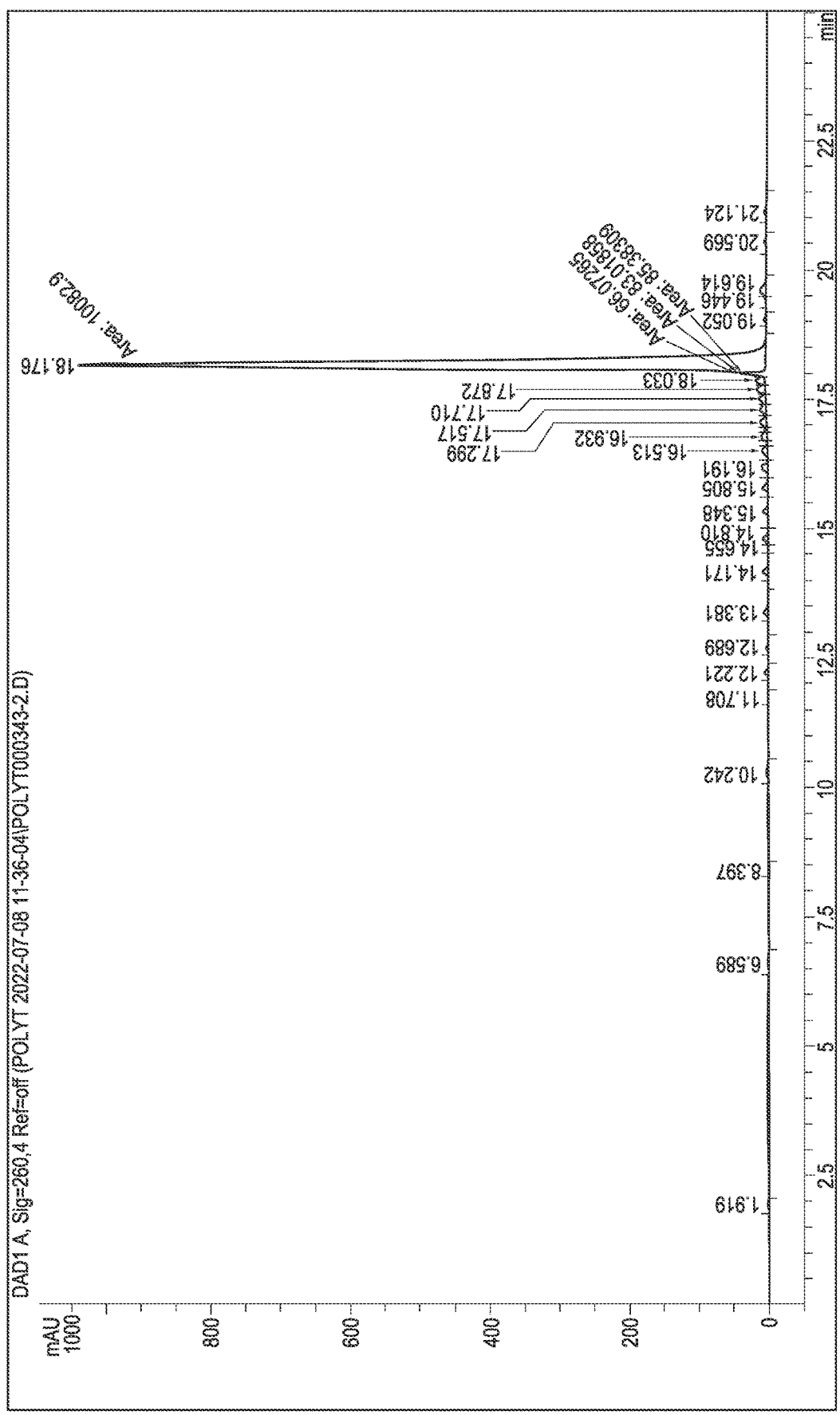
FIG. 6 is a HPLC chromatogram of a T20 DNA oligonucleotide synthesized utilizing crosslinker of Formula VIII-5 with acetoxystyrene according one embodiment of the present disclosure.

Following the same manner as described above in connection with Sample 1, DNA oligonucleotides with 5 mer and 20 mer were synthesized from succinated PCHP resin beads prepared from Comparative Sample 2. The FLP's of T5 and T20 were determined 90% and 88%, respectively (see Table 1). FIG. 6 is a HPLC chromatogram of a T20 DNA oligonucleotide synthesized in Comparative Sample 2.

Figure 7:
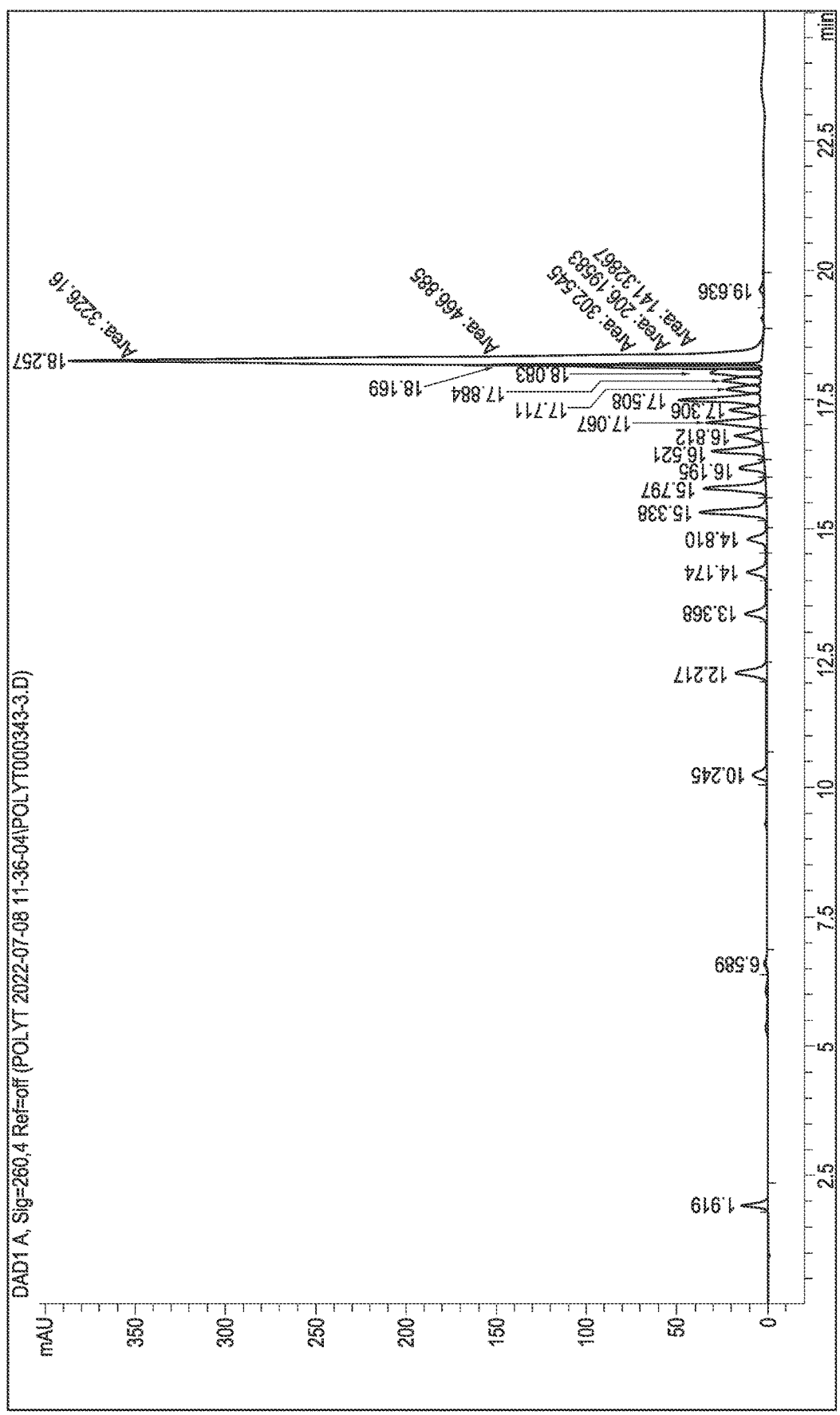
FIG. 7 is a HPLC chromatogram of a T20 DNA oligonucleotide synthesized utilizing crosslinker of Formula VIII-2 with acetoxystyrene according one embodiment of the present disclosure.

Following the same manner as described above in connection with Sample 1, DNA oligonucleotides with 5 mer and 20 mer were synthesized from succinated PCHP resin beads prepared from Comparative Sample 3. The FLP's of T5 and T20 were determined 88% and 52%, respectively (see Table 1). FIG. 7 is a HPLC chromatogram of a T20 DNA oligonucleotide synthesized in Comparative Sample 3.

TABLE 1

Summary of Resin Beads Particle Size Distribution, Loading and % FLP

| | Composition (% w/w) | | | | Particle Size | DMT Loading | FLP (%) | |
|---|---|---|---|---|---|---|---|---|
| ID# | Functional Comonomer | Styrene | Functional Comonomer Crosslinker | Crosslinker | μm | μmol/g | T5 | T20 |
| GE Primer Support ™ 5G | Amino-based styrene | n/a | n/a | n/a | 85 | 300 | 97 | 81 |
| NittoPhase ® HL | Hydroxy-based styrene | n/a | n/a | n/a | 98 | 327 | 94 | 88 |
| Sample 1 | Acetoxymethyl styrene | 80 | 10 | 10 (crosslinker of Formula VIII-4) | 94 | 228 | 99.7 | 90 |
| Sample 2 | Acetoxymethyl styrene | 80 | 10 | 10 (crosslinker of Formula VIII-6) | 78 | 263 | 97 | 90 |
| Sample 3 | Acetoxymethyl styrene | 80 | 10 | 10 (crosslinker of Formula VIII-3) | 101 | 199 | 98 | 82 |
| Sample 4 | Acetoxymethyl styrene | 60 | 20 | 20 (DVB) | 92 | 179 | 94 | 74 |
| Comparative Sample 1 | Acetoxy styrene | 80 | 10 | 10 (crosslinker of Formula VIII-4) | 93 | 231 | 99 | 94 |
| Comparative Sample 2 | Acetoxy styrene | 80 | 10 | 10 (crosslinker of Formula VIII-5) | 87 | 258 | 90 | 88 |
| Comparative Sample 3 | Acetoxy styrene | 80 | 10 | 10 (crosslinker of Formula VIII-2) | 99 | 248 | 88 | 52 |

What is claimed is:

1. A process of producing porous polymeric beads, comprising:
    copolymerizing (1) a styrene monomer, (2) an acetoxymethyl styrene or an acetoxystyrene monomer, and (3) one or more crosslinker monomers of Formula (VI), (VII) or (VIII) or a combination thereof, to provide a crosslinked copolymer; and
    hydrolyzing the crosslinked copolymer to convert the acetoxymethyl or acetoxy group to hydroxymethyl or hydroxy group in the crosslinked copolymer;

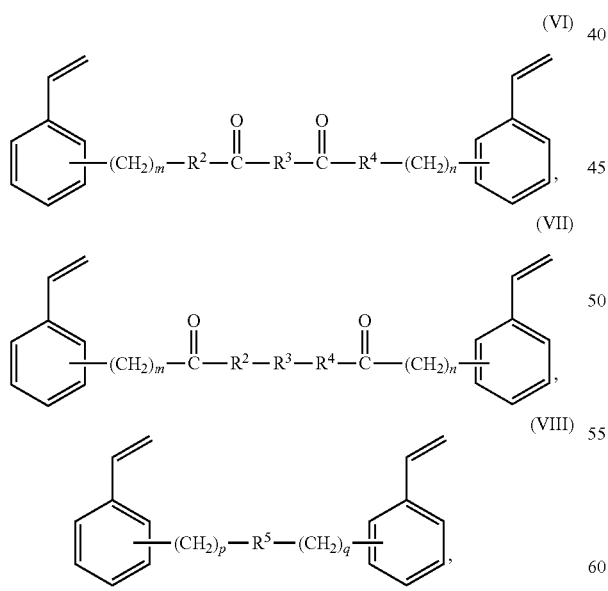

wherein each of $R^2$ and $R^4$ is independently —O— or —$NR^c$—;
each $R^c$ is independently H or $C_1$-$C_6$ alkyl;
each $R^3$ is independently $C_6$-$C_{10}$ arylene, $C_3$-$C_{10}$ membered cycloalkylene, five to ten membered heteroarylene, three to ten membered heterocyclylene, $C_1$-$C_{10}$ alkylene, 2 to 1500 membered heteroalkylene, or $C_1$-$C_{10}$ alkylene or 2 to 1500 membered heteroalkylene each independently interrupted by a ring or ring system selected from the group consisting of $C_6$-$C_{10}$ arylene, $C_3$-$C_{10}$ membered cycloalkylene, five to ten membered heteroarylene, and three to ten membered heterocyclylene;
$R^5$ is $C_6$-$C_{10}$ arylene, $C_3$-$C_{10}$ membered cycloalkylene, five to ten membered heteroarylene, three to ten membered heterocyclylene, —$CH_2OCH_2$—, —$CH_2O(CH_2)_{1-6}OCH_2$—, or $C_2$-$C_{10}$ heteroalkylene comprising one or more oxo (=O) atoms;
each of m, n, p and q is independently 0, 1, 2, 3, 4, 5 or 6;
wherein each phenyl moiety in Formula (VI), (VII) or (VIII) is optionally substituted with one or more $R^6$; and
each $R^6$ is independently selected from the group consisting of halo, cyano, hydroxy, amino, $C_1$-$C_6$ alkyl, $C_1$-$C_6$ haloalkyl, $C_1$-$C_6$ alkoxy, $C_1$-$C_6$ haloalkoxy, ($C_1$-$C_6$ alkyl)amino, ($C_1$-$C_6$ alkyl)hydroxy, ($C_1$-$C_6$ alkoxy)$C_1$-$C_6$ alkyl, and —O—($C_1$-$C_6$ alkoxy)$C_1$-$C_6$ alkyl.

2. The process of claim 1, wherein the amount of styrene monomer in the total amount of monomers is about 20 to 95 wt %.

3. The process of claim 1, wherein the amount of acetoxymethyl styrene monomer in the total amount of monomers is from about 1 to 55 wt %.

4. The process of claim 1, wherein the amount the crosslinker monomer(s) in the total amount of monomers is about 1 to 30 wt %.

5. The process of claim 1, wherein the loading amount of the acetoxymethyl styrene or acetoxystyrene monomer ranges from about 1 to 30 wt %, and the loading of hydroxyl groups after hydrolysis is at least about 170 μmol/g.

6. The process of claim 5, wherein the loading of the hydroxyl groups after hydrolysis is from about 250 μmol/g to about 350 μmol/g.

7. The process of claim 1, wherein the styrene monomer, the acetoxymethyl styrene or acetoxystyrene monomer, and the one or more crosslinker monomers are dissolved in one or more organic solvents to form an organic phase, and wherein the organic phase further comprises one or more polymerization initiators.

8. The process of claim 7, wherein the copolymerizing comprises contacting the organic phase with an aqueous phase comprising water and one or more dispersing agents to form an oil in water emulsion, and wherein the one or more dispersing agents comprises a polyalcohol.

9. The process of claim 3, wherein the acetoxymethyl styrene monomer has the structure

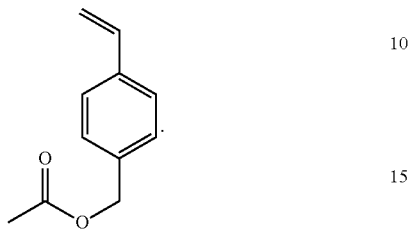

10. The process of claim 1, wherein the one or more crosslinker monomers of Formulas (VI), (VII) or (VIII) are selected from the group consisting of:

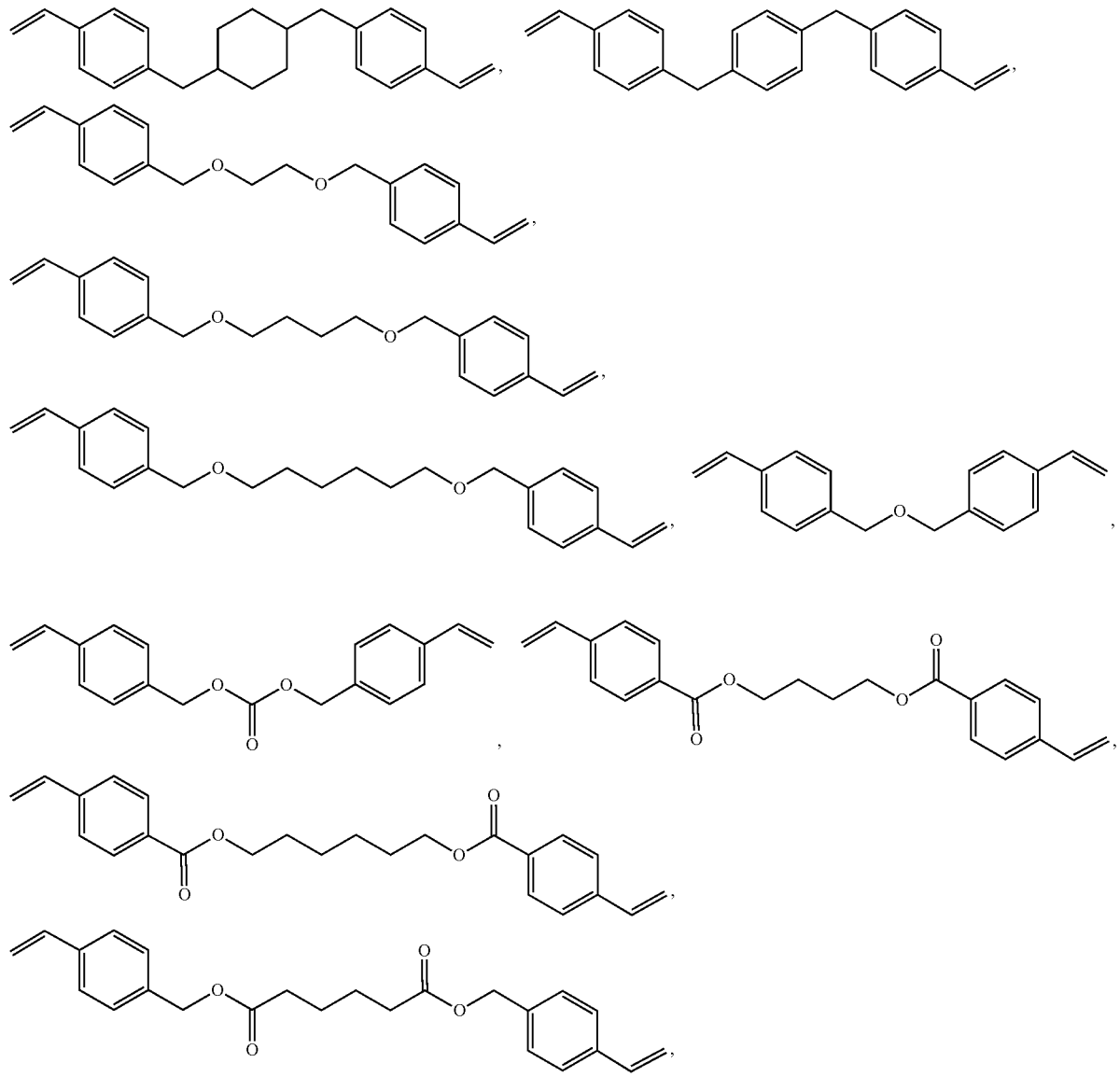

-continued
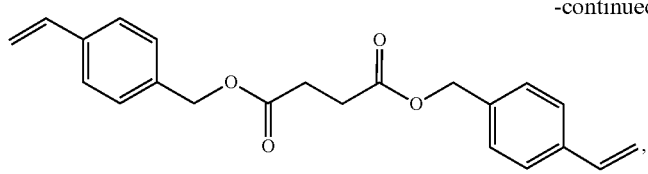
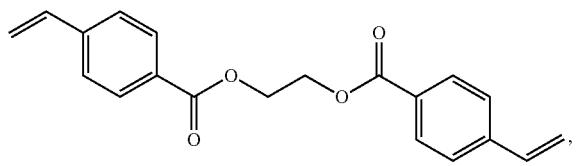
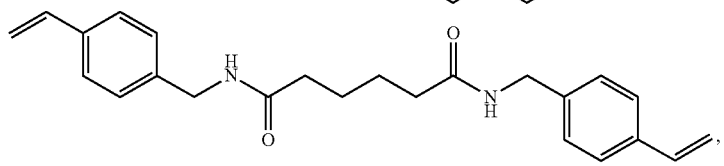
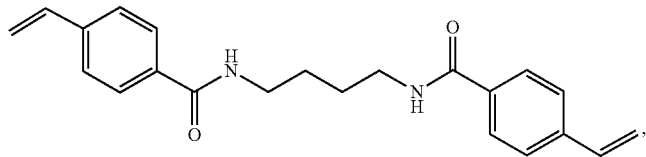
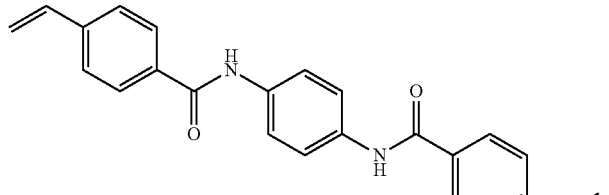
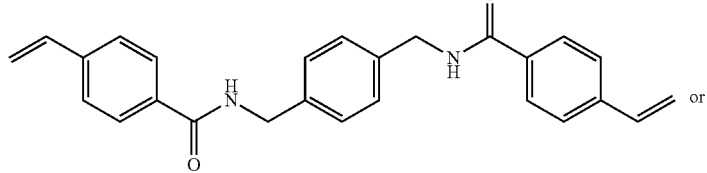 or
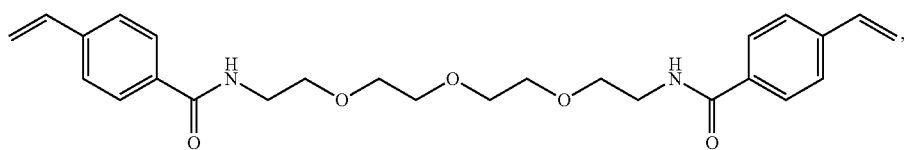
or combinations thereof.
11. The process of claim 1, wherein the crosslinked copolymer comprising the structure:
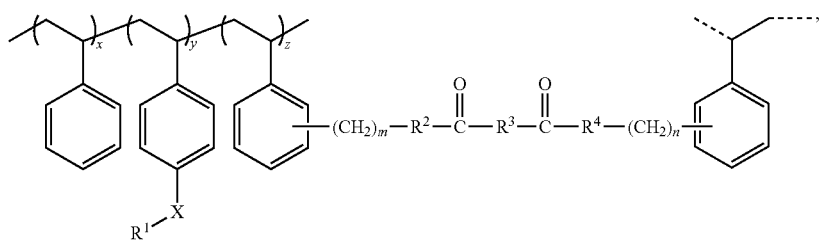

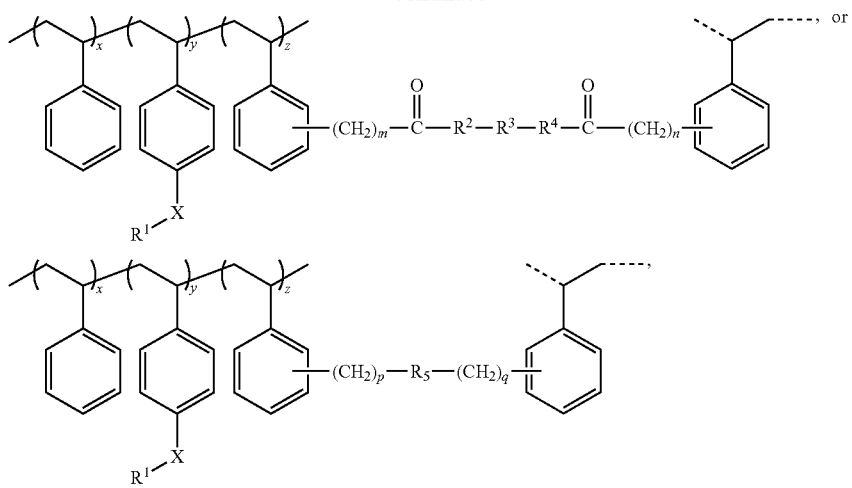

or combinations thereof, wherein R¹ is OH; X is absent or —CH₂—; x, y, and z are each independently an integer from 1 to about 10000.

12. The process of claim 11, wherein the crosslinked copolymer comprises the structure:

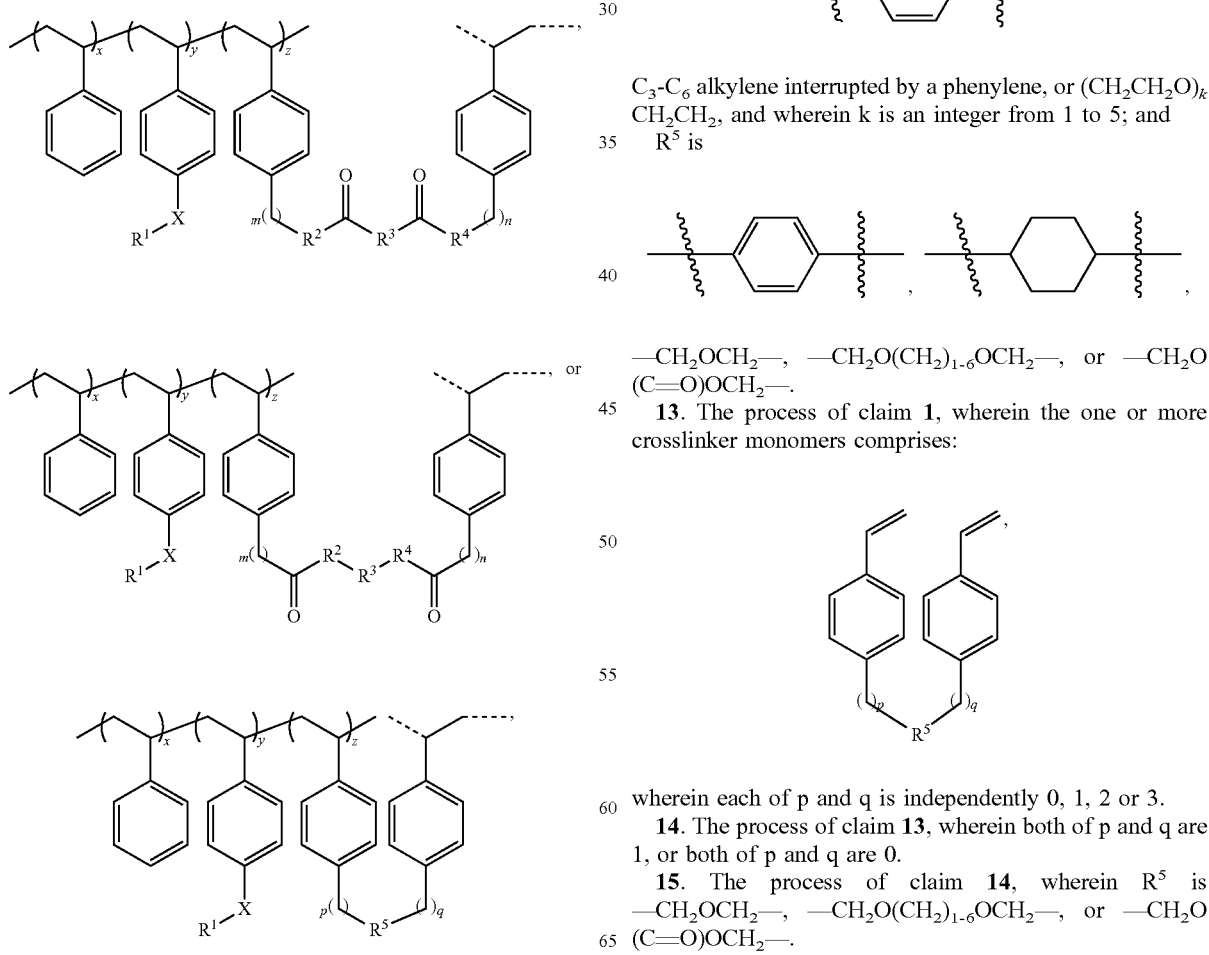

or combinations thereof,
wherein each of R² and R⁴ is O or NH;
each R³ is independently C₁-C₆ alkylene, $$\begin{array}{c}\xi\\\xi\end{array}\!\!-\!\!\!\!\begin{array}{c}\\\\\end{array}\!\!\!\!-\!\!\!\!\begin{array}{c}\xi\\\xi\end{array},$$

C₃-C₆ alkylene interrupted by a phenylene, or (CH₂CH₂O)ₖCH₂CH₂, and wherein k is an integer from 1 to 5; and
R⁵ is —CH₂OCH₂—, —CH₂O(CH₂)₁₋₆OCH₂—, or —CH₂O(C=O)OCH₂—.

13. The process of claim 1, wherein the one or more crosslinker monomers comprises:

wherein each of p and q is independently 0, 1, 2 or 3.

14. The process of claim 13, wherein both of p and q are 1, or both of p and q are 0.

15. The process of claim 14, wherein R⁵ is —CH₂OCH₂—, —CH₂O(CH₂)₁₋₆OCH₂—, or —CH₂O(C=O)OCH₂—.

16. The process of claim 13, wherein both of p and q are 0, and R⁵ is —CH₂OCH₂—.

17. The process of claim 1, wherein the porous beads have an average pore size ranging from about 10 nm to about 200 nm.

18. The process of claim 1, wherein the porous beads have an average pore size ranging from about 20 nm to about 175 nm.

19. The process of claim 1, wherein the porous beads having an average particle size greater than about 40 μm.

20. The process of claim 1, wherein the porous beads having an average particle size from about from about 50 μm to about 300 μm.

* * * * *

UNITED STATES PATENT AND TRADEMARK OFFICE
CERTIFICATE OF CORRECTION

PATENT NO.         : 12,065,516 B2
APPLICATION NO.    : 18/483423
DATED              : August 20, 2024
INVENTOR(S)        : Jingshe Song Page 1 of 3

It is certified that error appears in the above-identified patent and that said Letters Patent is hereby corrected as shown below:

In the Specification

Column 10, Line 40 (approx.), delete "pmol" and insert -- µmol --.

Column 11, Line 2, delete "cyclalkynyl" and insert -- cycloalkynyl --.

Column 20, Line 13, delete "p-toluensulfonic" and insert -- p-toluenesulfonic --.

Column 23 and 24, Lines 1-25 (approx.), delete

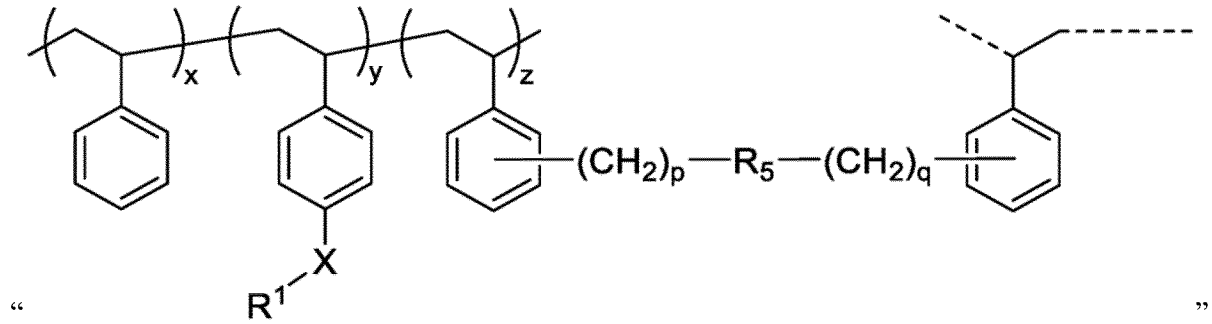

"                                                                                       "
and insert

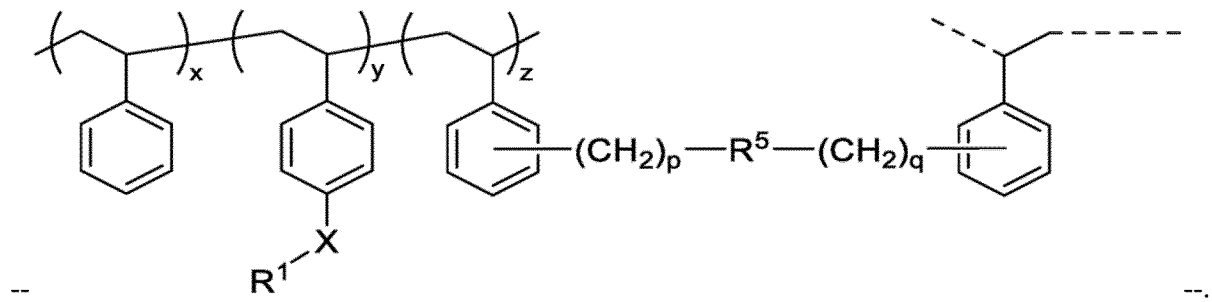

--                                                                                       --.

Column 23, Line 49, delete "0" and insert -- —O— --.

Signed and Sealed this
Twenty-ninth Day of April, 2025

Coke Morgan Stewart
*Acting Director of the United States Patent and Trademark Office*

CERTIFICATE OF CORRECTION (continued)
U.S. Pat. No. 12,065,516 B2

Page 2 of 3

Column 41, Lines 52-66 (approx.), delete " 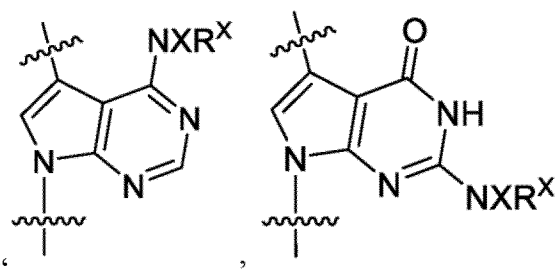 " and insert

-- 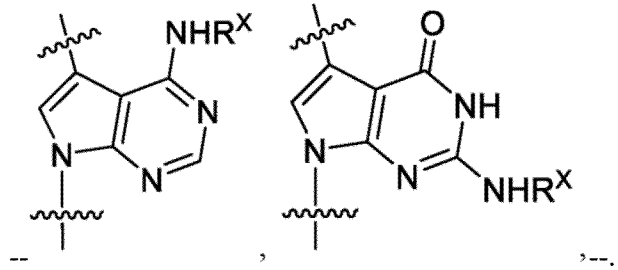 --.

Column 42, Lines 1-13 (approx.), delete " 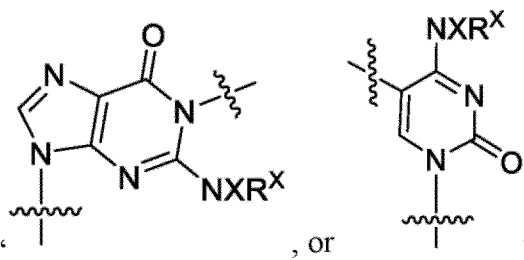 " and insert

-- 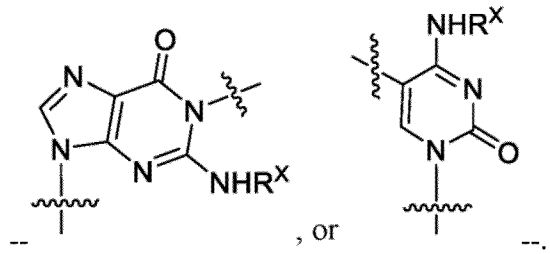 --.

Column 44, Lines 52-66, delete " 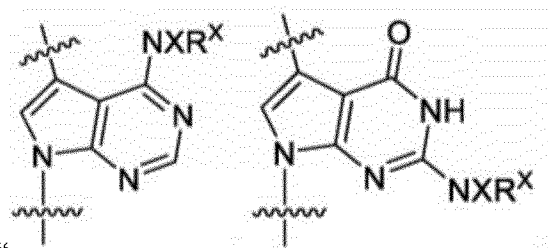 " and insert

-- 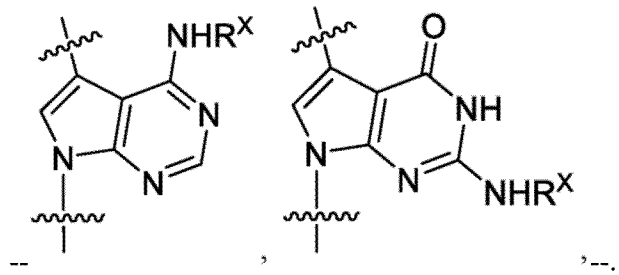 --.

CERTIFICATE OF CORRECTION (continued)
U.S. Pat. No. 12,065,516 B2

Column 45, Lines 1-13, delete " 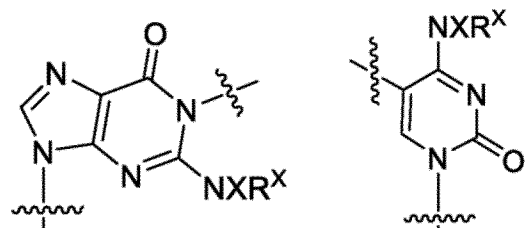 , or " and insert 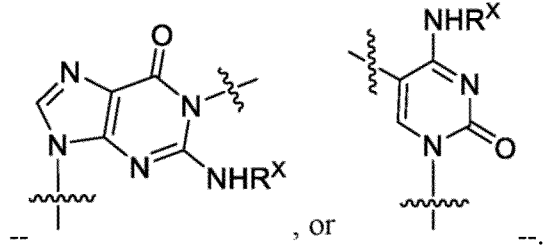 , or --.

Column 53, Line 13 (approx.), delete "dimetylformamide" and insert -- dimethylformamide --.

Column 53, Line 18 (approx.), delete "1,4-xylelenediamine" and insert -- 1,4-xylylenediamine --.

In the Claims

Column 71 and 72, Lines 1-22 (approx.), Claim 11, delete

" 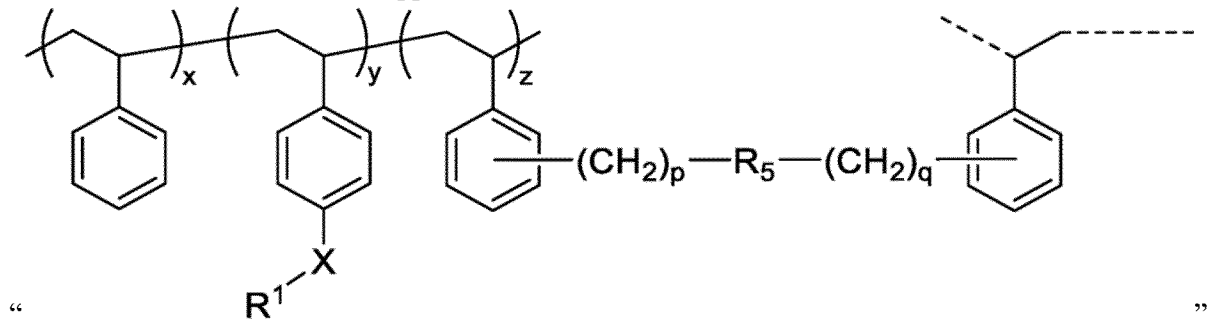 "

and insert

-- 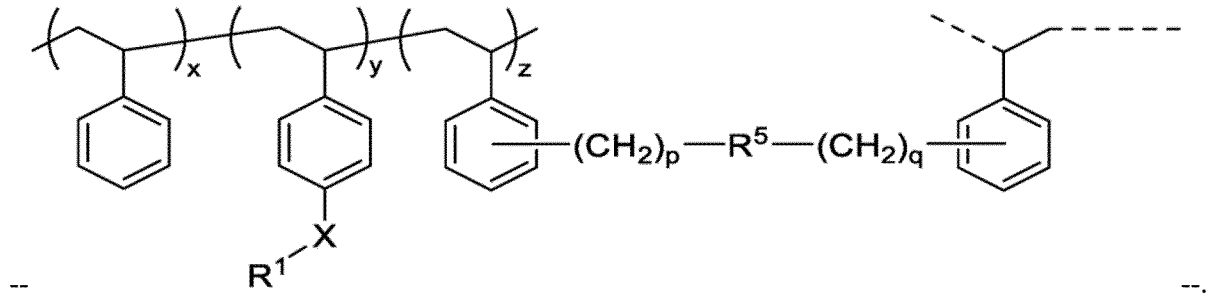 --.

Column 72, Lines 33-34, Claim 12, delete "$(CH_2CH_2O)_kCH_2CH_2$," and insert -- $—(CH_2CH_2O)_kCH_2CH_2—$, --.

Column 73, Line 10, Claim 20, delete "from about from about" and insert -- from about --.